(12) United States Patent
Sato et al.

(10) Patent No.: US 8,686,189 B2
(45) Date of Patent: Apr. 1, 2014

(54) OPTICALLY ACTIVE DIAMINE DERIVATIVE AND PROCESS FOR PRODUCING THE SAME

(75) Inventors: Koji Sato, Edogawa-ku (JP); Kotaro Kawanami, Edogawa-ku (JP); Tsutomu Yagi, Edogawa-ku (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 871 days.

(21) Appl. No.: 12/066,873

(22) PCT Filed: Sep. 15, 2006

(86) PCT No.: PCT/JP2006/318432
§ 371 (c)(1),
(2), (4) Date: Mar. 14, 2008

(87) PCT Pub. No.: WO2007/032498
PCT Pub. Date: Mar. 22, 2007

(65) Prior Publication Data
US 2009/0105491 A1 Apr. 23, 2009

(30) Foreign Application Priority Data
Sep. 16, 2005 (JP) .................................. 2005-269642

(51) Int. Cl.
*C07C 211/00* (2006.01)
*C07C 209/00* (2006.01)

(52) U.S. Cl.
USPC ............ 564/462; 564/336; 564/448; 564/461

(58) Field of Classification Search
None
See application file for complete search history.

(56) References Cited

U.S. PATENT DOCUMENTS

| | | | |
|---|---|---|---|
| 3,041,357 A | 6/1962 | Phillips et al. | |
| 2005/0119486 A1 | 6/2005 | Ohta et al. | |
| 2007/0135476 A1 | 6/2007 | Nagasawa et al. | |

FOREIGN PATENT DOCUMENTS

| | | |
|---|---|---|
| CN | 1438993 A | 8/2003 |
| EP | 0 364 708 A1 | 4/1990 |
| JP | 2 115151 | 4/1990 |
| JP | 2003 183286 | 7/2003 |
| JP | 2003 206266 | 7/2003 |
| WO | 01 74774 | 10/2001 |
| WO | 03 000657 | 1/2003 |
| WO | 03 000680 | 1/2003 |
| WO | 03 016302 | 2/2003 |
| WO | 2004 058715 | 7/2004 |

OTHER PUBLICATIONS

Scriven et al. Chem. Rev vol. 88(2), Mar./Apr. 1988, p. 298-368.*
Chinese Office Action issued Dec. 21, 2010, in Patent Application No. 200680033991.7 (with English-language translation).
Extended European Search Report issued Jun. 14, 2013 in Patent Application No. 06810224.3.
Alicia Maestro, et al., "Enzymatic resolution of (±)—trans-2-aminocyclohexanol and (±)—trans-2-aminocyclopentanol", Tetrahedron:Asymmetry, Pergamon Press Ltd, Oxford, GB, ISSN: 0957-4166, DOI: 10.1016/S0957-4166 (97) 00368-6, XP004090525, vol. 8, No. 18, Sep. 25, 1997, pp. 3153-3159.
Jiaxi Xu, et al., "A General Route to the Synthesis of N-Protected 1-Substituted and 1, 2-Disubstituted Taurines", Synthesis, ISSN: 0039-7881, DOI: 10.1055/s-2003-44382, XP55065306, No. 2, Jan. 2004, pp. 276-282.

* cited by examiner

*Primary Examiner* — Clinton Brooks
(74) *Attorney, Agent, or Firm* — Oblon, Spivak, McClelland, Maier & Neustadt, L.L.P.

(57) ABSTRACT

The invention is directed to a process for producing intermediates of a compound which exhibits an activated blood coagulation factor Xa inhibitory action and which is a useful preventive and a therapeutic agent for thrombotic diseases. The intermediate production process is represented by the following reaction scheme.

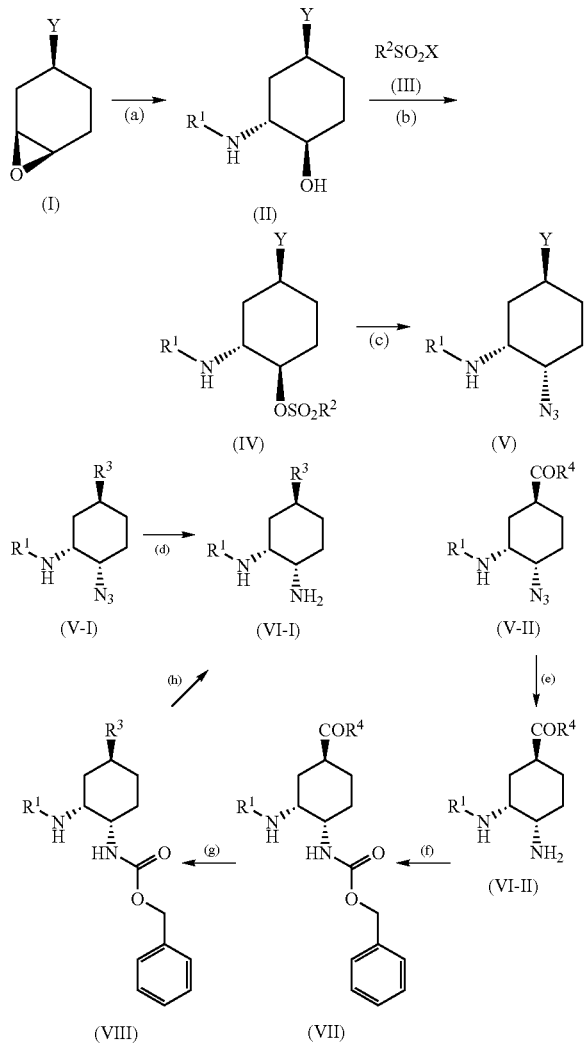

6 Claims, No Drawings

OPTICALLY ACTIVE DIAMINE DERIVATIVE AND PROCESS FOR PRODUCING THE SAME

TECHNICAL FIELD

The present invention relates to a process for producing intermediates of a compound which exhibits an activated blood coagulation factor Xa inhibitory action and which is a useful preventive and a therapeutic agent for thrombotic diseases.

BACKGROUND ART

As disclosed in, for example, Patent Document 1, the Compound (VI-I) mentioned hereinbelow is an important intermediate in the production of a compound which exhibits an activated blood coagulation factor X inhibitory action and which is a useful preventive and a therapeutic agent for thrombotic diseases. In the process for producing Compound (VI-I) as disclosed therein, highly toxic sodium azide is used in a step of producing Compound (II) from Compound (I) and the formed azide must be subjected to hydrogenolysis. Thus, this process is disadvantageous in the industry-scale production. Since the process employs dichloromethane as a solvent in the production of Compound (IV), it is not considered an environment-friendly production process from the viewpoint of so-called green chemistry. In addition, the process requires a production facility which allows an ultra-low-temperature (−30 to −78° C.) process, and being industrially disadvantageous. Moreover, the production yield of Compound (V) is considerably low (about 30 to 40%) in this process, and the yield must be enhanced from the industrial viewpoint. For producing Compound (VI-I), hydrogenolysis under pressurized hydrogen conditions must be performed, requiring a closable pressure apparatus such as an autoclave.
Patent Document 1: International Patent Publication WO01/74774, pamphlet

DISCLOSURE OF THE INVENTION

Problems to be Solved by the Invention

An object of the present invention is to solve the problems involved in the process disclosed in International Patent Publication WO01/74774, thereby providing an industrial process for producing Compound (VI-I).

Means for Solving the Problems

The present inventors have carried out extensive studies, and have found that treating Compound (I) with aqueous ammonia or a similar substance in a solvent results in regiospecific nucleophilic attack of amine, and that Compound (II) is produced through protection of the amine with dialkyl dicarbonate. The inventors have also found that treating Compound (II) with compound (III) in a solvent in the presence of a base effectively yields Compound (IV), which successfully achieving an environment-friendly production process from the viewpoint of green chemistry. The inventors have further found that Compound (V) can be produced at high yield and high selectivity through treatment with an azide in a solvent. The inventors have further found that reduction of Compound (V) proceeds through hydrogenolysis under normal pressure conditions in the presence of a hydrogen source and a metallic catalyst, whereby Compound (VI-I) can be efficiently produced in a simple manner by means of a conventional reactor.

Accordingly, the present invention provides a process for producing a compound represented by formula (II):

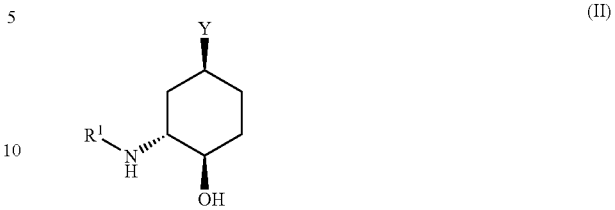

(II)

(wherein Y represents —COR, wherein R represents a C1-C8 alkoxy group, a C6-C14 aryloxy group, a C2-C8 alkenyloxy group, a C7-C26 aralkyloxy group, or a di(C1-C6 alkyl) amino group; and $R^1$ represents a C2-C7 alkoxycarbonyl group), which comprises treating a compound represented by formula (I):

(I)

(wherein Y has the same meaning as defined above) in a solvent with aqueous ammonia or a solution of ammonia in C1-C4 alcohol and, subsequently, with a di(C1-C6 alkyl) dicarbonate.

The present invention also provides a process for producing a compound represented by formula (IV):

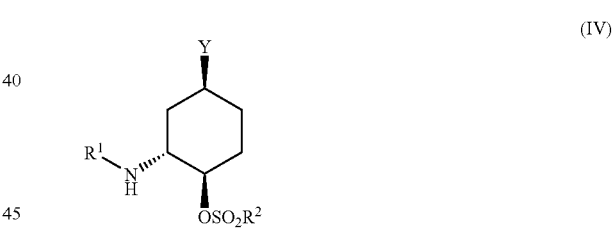

(IV)

(wherein Y and $R^1$ have the same meanings as defined above, and $R^2$ represents a C1-C6 alkyl group, a C1-C6 halogenoalkyl group, or a phenyl group which may have a halogen atom, a C1-C6 alkyl group, a C1-C6 halogenoalkyl group, a C1-C6 alkoxy group, a nitro group, a carbamoyl group, or a cyano group), which comprises reacting a compound represented by formula (II):

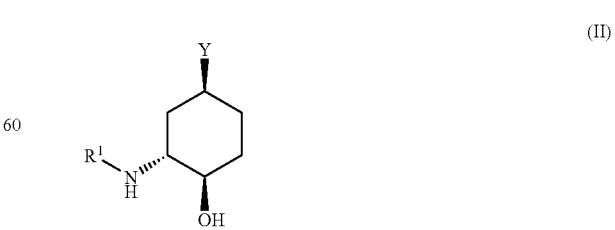

(II)

(wherein Y and $R^1$ have the same meanings as defined above) with a compound $R^2SO_2X$ (III) (wherein $R^2$ has the same meaning as defined above, and X represents a halogen atom) in a solvent in the presence of a base.

The present invention also provides a process for producing a compound represented by formula (V):

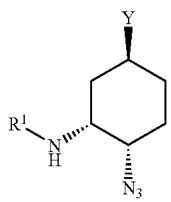

(V)

(wherein Y and $R^1$ have the same meanings as defined above), which comprises treating a compound represented by formula (IV):

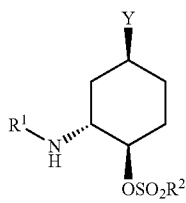

(IV)

(wherein Y, $R^1$, and $R^2$ have the same meanings as defined above) with an azide in a solvent in the presence or absence of a phase-transfer catalyst.

The present invention also provides a process for producing a compound represented by formula (VI-I):

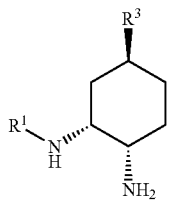

(VI-I)

(wherein $R^1$ has the same meaning as defined above, and $R^3$ represents a di(C1-C6 alkyl)carbamoyl group or an oxadiazolyl group) or a salt thereof, which comprises subjecting a compound represented by formula (V-I):

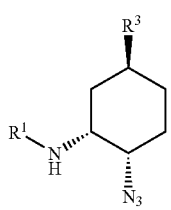

(V-I)

(wherein $R^1$ and $R^3$ have the same meanings as defined above) to hydrogenolysis in a solvent in the presence of a metallic catalyst and a hydrogen source.

The present invention also provides a process for producing a compound represented by formula (VI-II):

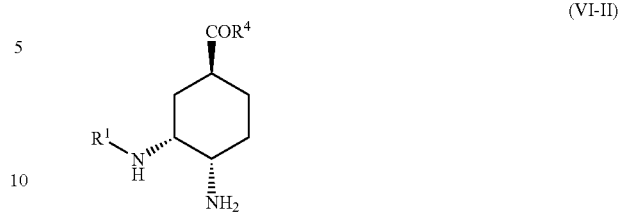

(VI-II)

(wherein $R^4$ represents a C1-C8 alkoxy group, a C6-C14 aryloxy group, a C2-C8 alkenyloxy group, or a C7-C26 aralkyloxy group, and $R^1$ has the same meaning as defined above) or a salt thereof, which comprises subjecting a compound represented by formula (V-II):

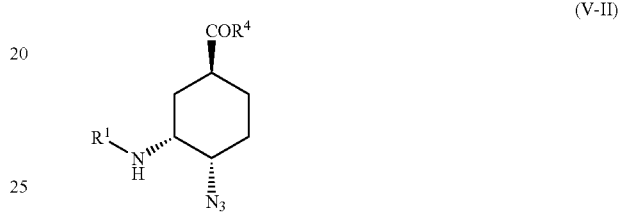

(V-II)

(wherein $R^1$ and $R^4$ have the same meanings as defined above) to hydrogenolysis in a solvent in the presence of a metallic catalyst and a hydrogen source.

The present invention also provides a process for producing a compound represented by formula (VII):

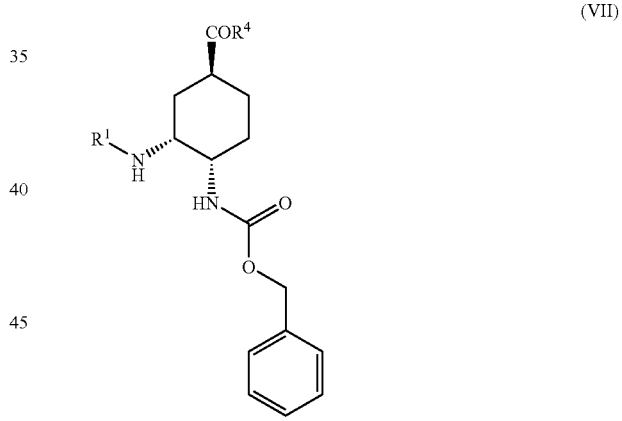

(VII)

(wherein $R^1$ and $R^4$ have the same meanings as defined above), which comprises treating a compound represented by formula (VI-II):

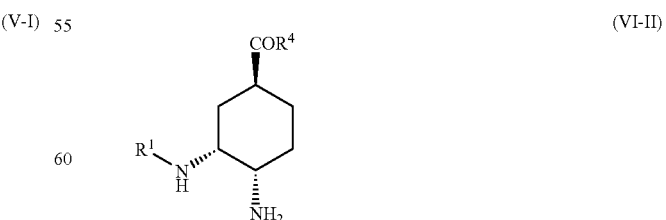

(VI-II)

(wherein $R^1$ and $R^4$ have the same meanings as defined above) or a salt thereof with a benzyloxycarbonyl halide in a solvent in the presence of a base.

The present invention also provides a process for producing a compound represented by formula (VIII):

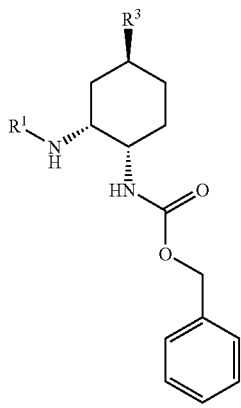

(VIII)

(wherein $R^1$ and $R^3$ have the same meanings as defined above), which comprises treating a compound represented by formula (VII):

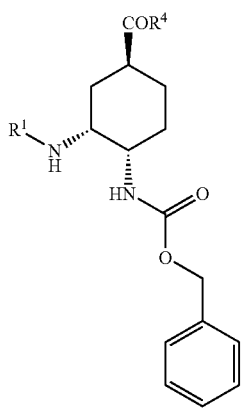

(VII)

(wherein $R^1$ and $R^4$ have the same meanings as defined above) with a base and, subsequently, (1) condensing the resultant product with a di(C1-C6 alkyl)amine; (2) condensing the resultant product with hydrazine to form a carbohydrazide, transforming the carbohydrazide to a corresponding acyl equivalent by use of an acylating agent in the presence or absence of an acid, and treating the acyl equivalent in the presence or absence of a dehydrating agent; or (3) condensing the resultant product with ammonia to form a carbamide, treating the carbamide with a dehydrating agent to form a nitrile derivative, treating the nitrile derivative with hydroxylamine to form an amidoxime, and treating the amidoxime with an acylating agent in the presence or absence of a dehydrating agent or an acid.

The present invention also provides a process for producing a compound represented by formula (VI-I):

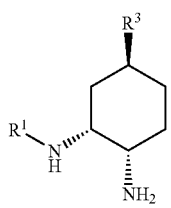

(VI-I)

(wherein $R^1$ and $R^3$ have the same meanings as defined above) or a salt thereof, which comprises subjecting a compound represented by formula (VIII):

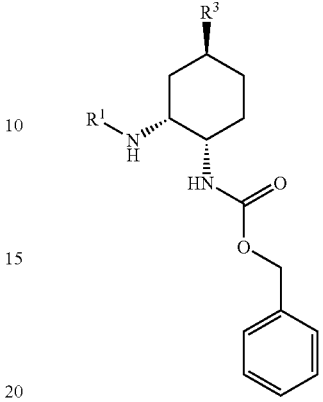

(VIII)

(wherein $R^1$ and $R^3$ have the same meanings as defined above) to hydrogenolysis in a solvent in the presence of a metallic catalyst and a hydrogen source.

The present invention provides a compound represented by formula (I'):

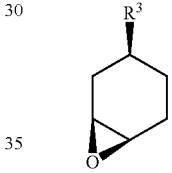

(I')

(wherein $R^3$ has the same meaning as defined above).

The present invention provides a compound represented by formula (II'):

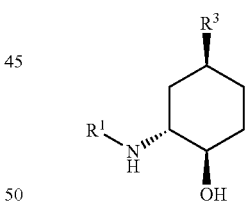

(II')

(wherein $R^1$ and $R^3$ have the same meanings as defined above).

The present invention provides a compound represented by formula (IV'):

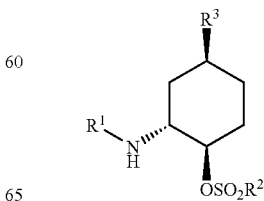

(IV')

(wherein $R^1$ to $R^3$ have the same meanings as defined above).

The present invention provides a compound represented by formula (V'):

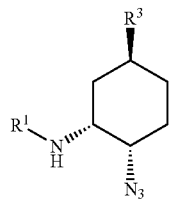

(V')

(wherein $R^1$ and $R^3$ have the same meanings as defined above).

Effects of the Invention

According to the present invention, t-butyl {(1R,2S,5S)-2-amino-5-[(dimethylamino)carbonyl]cyclohexyl}carbamate can be produced at high yield and high selectivity. The production process of the present invention realizes reduction of the amount of a toxic reagent, as compared with the process disclosed in International Patent Publication WO01/74774, and does not employ a halogen-base solvent. Thus, the process of the invention enhances production yield and is industrially applicable. Therefore, the process of the present invention is an industrially useful process for producing t-butyl {(1R,2S,5S)-2-amino-5-[(dimethylamino)carbonyl]cyclohexyl}carbamate, which is a starting material for a compound which exhibits an activated blood coagulation factor X inhibitory action and which is a useful preventive and a therapeutic agent for thrombotic diseases.

BEST MODES FOR CARRYING OUT THE INVENTION

The steps included in the production process of the present invention are shown in the following scheme. These steps will hereinafter be described in detail.

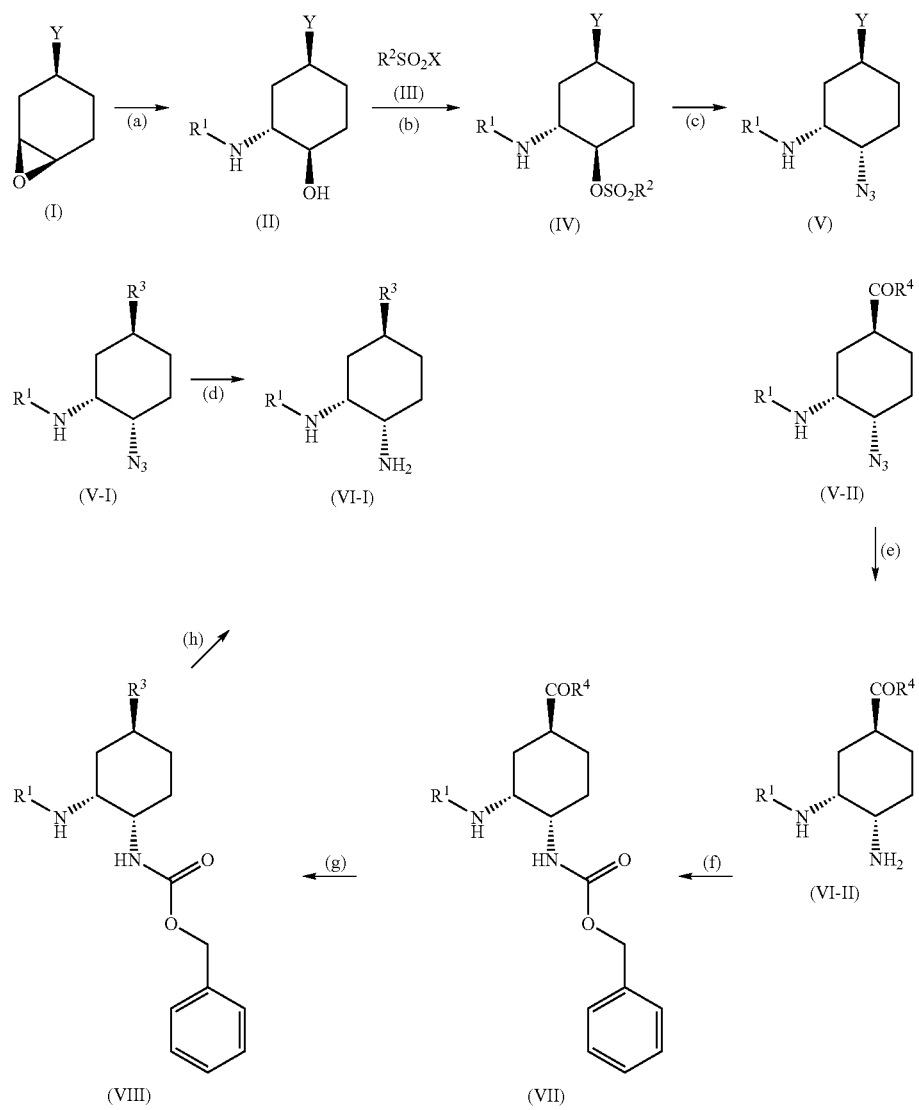

In the above scheme, Y represents —COR (wherein R represents a C1-C8 alkoxy group, a C6-C14 aryloxy group, a C2-C8 alkenyloxy group, a C7-C26 aralkyloxy group, or a di(C1-C6 alkyl)amino group); $R^1$ represents a C2-C7 alkoxycarbonyl group; $R^2$ represents a C1-C6 alkyl group, a C1-C6 halogenoalkyl group, or a phenyl group having, as a substituent, a halogen atom, a C1-C6 alkyl group, a C1-C6 halogenoalkyl group, a C1-C6 alkoxy group, a nitro group, a carbamoyl group, or a cyano group; $R^3$ represents di(C1-C6 alkyl)carbamoyl group or an oxadiazolyl group; $R^4$ represents a C1-C8 alkoxy group, a C6-C14 aryloxy group, a C2-C8 alkenyloxy group, or a C7-C26 aralkyloxy group; and X represents a halogen atom.

The substituents referred in the reaction steps will next be described.

Y represents —COR, and R is a linear, branched, or cyclic C1-C8 alkoxy group such as a methoxy group, an ethoxy group, a n-propoxy group, an isopropoxy group, or a cyclopropyloxy group; a C6-C14 aryloxy group such as a phenoxy group or a naphthoxy group; a linear or branched C2-C8 alkenyloxy group such as a vinyloxy group, an allyloxy group, or a propenyloxy group; a C7-C26 aralkyloxy group (e.g., benzyloxy) in which a C1-C12 alkoxy group is substituted by a C6-C14 aryl group; or a di(C1-C6 alkyl)amino group (e.g., ethylmethylamino or dimethylamino) in which an amino group is substituted by linear, branched, or cyclic C1-C6 alkyl groups, which are identical to or different from one another.

Examples of the linear, branched, or cyclic C1-C6 alkyl group include methyl, ethyl, n-propyl, isopropyl, n-butyl, sec-butyl, tert-butyl, n-pentyl, isopentyl, n-hexyl, and isohexyl.

In the present invention, R is preferably a C1-C8 alkoxy group or a di(C1-C6 alkyl)amino group. The alkoxy group is preferably a C1-C6 alkoxy group, with ethoxy being particularly preferred. The di(C1-C6 alkyl)amino group is preferably a di(C1-C4 alkyl)amino group, with dimethylamino being particularly preferred.

$R^1$ is a linear, branched, or cyclic C2-C7 alkoxycarbonyl group such as methoxycarbonyl group, ethoxycarbonyl, or tert-butoxycarbonyl group. In the present invention, $R^1$ is preferably a C2-C5 alkoxycarbonyl group, with tert-butoxycarbonyl being particularly preferred.

$R^2$ is a linear, branched, or cyclic C1-C6 alkyl group as mentioned in relation to R; a C1-C6 halogenoalkyl group (e.g., chloromethyl or trifluoroethyl) in which a C1-C6 alkyl group is substituted by 1 to 3 halogen (e.g., fluorine, chlorine, bromine, or iodine) atoms; or a phenyl group which may have a halogen atom, a C1-C6 alkyl group, a C1-C6 halogenoalkyl group, a C1-C6 alkoxy group, a nitro group, a carbamoyl group, or a cyano group. In the present invention, $R^2$ is preferably a C1-C6 alkyl group, with methyl being particularly preferred.

$R^3$ is a di(C1-C6 alkyl)carbamoyl group or an oxadiazolyl group. The C1-C6 alkyl groups represented by $R^3$ may be the same groups as mentioned in relation to R and may be identical to or different from one another. In the present invention, when $R^3$ is an oxadiazolyl group, a 1,3,4-oxadiazol-2-yl group or a 1,2,4-oxadiazol-3-yl group is preferred, with 1,3,4-oxadiazol-2-yl being particularly preferred. When $R^3$ is a di(C1-C6 alkyl)carbamoyl group, a di(C1-C4 alkyl)amino group is preferred, with dimethylamino being particularly preferred.

$R^4$ is a C1-C8 alkoxy group, a C6-C14 aryloxy group, a C2-C8 alkenyloxy group, or a C7-C26 aralkyloxy group, which are the same as mentioned in relation to R. In the present invention, $R^4$ is preferably a C1-C8 alkoxy group, more preferably a C1-C6 alkoxy group, with ethoxy being particularly preferred.

X is a halogen atom. In the present invention, X is preferably a chlorine atom, a bromine atom, or an iodine atom, with chlorine being particularly preferred.

Hereinafter, the steps included in the production process according to the present invention will be described in detail.
<Step (a)>

In Step (a), Compound (II) is produced. Compound (II) can be produced through treating Compound (I) in a solvent with aqueous ammonia or a solution of ammonia in C1-C4 alcohol and, subsequently, with a di(C1-C6 alkyl)dicarbonate.

A variety of solvents may be employed. For example, hydrocarbon solvent, alcoholic solvent, ether solvent, amide solvent, cyclic urea solvent, and halohydrocarbon solvent may be employed. Examples of the hydrocarbon solvent include n-hexane, n-pentane, benzene, toluene, and xylene. Examples of the alcoholic solvent include C1-C4 alcohols such as methanol, ethanol, propanol, isopropanol (IPA), n-butanol, and t-butanol. Examples of the ether solvent include diethyl ether, diisopropyl ether (IPE), methyl t-butyl ether (MTBE), tetrahydrofuran (THF), cyclopentyl methyl ether, dimethoxyethane, and 1,4-dioxane. Examples of the amide solvent include dimethylformamide (DMF), dimethylacetamide (DMAc), and N-methyl-2-pyrrolidone (NMP). Examples of the cyclic urea solvent include 1,3-dimethyl-2-imidazolidinone (DMI) and 1,3-dimethyl-3,4,5,6-tetrahydro-2(1H)-pyrimidinone (DMPU). Examples of the halohydrocarbon solvent include chloroform, methylene chloride, and 1,2-dichloroethane (EDC). Other than these solvents, water, dimethylsulfoxide (DMSO), sulfolane, acetonitrile, (C1-C4 alkyl)acetate esters such as ethyl acetate, and acetone may be used. These solvent may be used alone or in combination of two or more species.

Among these solvents, C1-C4 alcohol solvents such as methanol, ethanol, propanol, isopropanol (IPA), n-butanol, and t-butanol are preferred, with ethanol being particularly preferred.

Among the aqueous ammonia and a solution of ammonia in C1-C4 alcohol employed in the treatment, the solution of ammonia in C1-C4 alcohol may be prepared through inducing ammonia into C1-C4 alcohol. Alternatively, a commercial product thereof may also be employed.

The reaction temperature, which varies in accordance with the type of the employed solvent, is −78° C. to the boiling point of the solvent, preferably room temperature to 75° C. The reaction time is generally 12 to 96 hours, preferably 24 to 72 hours.

Examples of the di(C1-C6 alkyl)dicarbonate employed in Step (a) include dimethyl dicarbonate, diethyl dicarbonate, diisopropyl dicarbonate, and di-tert-butyl dicarbonate, with di-tert-butyl dicarbonate being particularly preferred. Generally, the di(C1-C6 alkyl)dicarbonate is preferably used in an amount of 1 to 5 mol, particularly preferably 1 to 2 mol, with respect to 1 mol of Compound (I).
<Step (b)>

In Step (b), Compound (IV) is produced. Compound (IV) may be produced through reacting Compound (II) with Compound (III) in a solvent in the presence of a base.

A variety of solvents may be employed. For example, hydrocarbon solvent, alcoholic solvent, ether solvent, amide solvent, cyclic urea solvent, and halohydrocarbon solvent may be employed. Examples of the hydrocarbon solvent include n-hexane, n-pentane, benzene, toluene, and xylene. Examples of the alcoholic solvent include C1-C4 alcohols such as methanol, ethanol, propanol, isopropanol (IPA), n-butanol, and t-butanol. Examples of the ether solvent include diethyl ether, diisopropyl ether (IPE), methyl t-butyl ether (MTBE), tetrahydrofuran (THF), cyclopentyl methyl ether, dimethoxyethane, and 1,4-dioxane. Examples of the amide solvent include dimethylformamide (DMF), dimethylacetamide (DMAc), and N-methyl-2-pyrrolidone (NMP). Examples of the cyclic urea solvent include 1,3-dimethyl-2-imidazolidinone (DMI) and 1,3-dimethyl-3,4,5,6-tetrahydro-2(1H)-pyrimidinone (DMPU). Examples of the halohydrocarbon solvent include chloroform, methylene chloride, and 1,2-dichloroethane (EDC). Other than these solvents, water, dimethylsulfoxide (DMSO), sulfolane, acetonitrile, 4-methyl-2-pentanone (MIBK), (C1-C4 alkyl)acetate esters such as ethyl acetate, and acetone may be used. These solvent may be used alone or in combination of two or more species.

Among these solvents, hydrocarbon solvents, 4-methyl-2-pentanone (MIBK), and (C1-C4 alkyl)acetate esters are preferred, with 4-methyl-2-pentanone (MIBK) and ethyl acetate being particularly preferred.

The reaction temperature, which varies in accordance with the type of the employed solvent, is −78° C. to the boiling point of the solvent, preferably 0° C. to 30° C. Generally, the reaction time is 30 minutes to 5 hours, preferably 1 hour to 3 hours.

The base may be an organic base or an inorganic base. Examples of the base which may be employed in Step (b) include hydroxides, carbonates, hydrogencarbonates, and alkoxides of an alkali metal or an alkaline earth metal (e.g., sodium, potassium, lithium, magnesium, or calcium); metal hydrides such as sodium hydride, potassium hydride, lithium hydride; alkyllithium reagents such as n-butyllithium, methyllithium, and lithium diisopropylamide; tertiary amines such as triethylamine and N,N-diisopropylethylamine; and heterocyclic compound such as 1,8-diazabicyclo[5.4.0]undec-7-ene (DBU), 1,8-diazabicyclo[4.3.0]non-5-ene (DBN), dimethylaniline, and N-methylmorpholine. In order to promote the reaction, the reaction may be performed in the presence of, for example, a quaternary ammonium salt such as tetrabutylammonium bromide or benzyltriethylammonium chloride; an alkali metal or alkaline earth metal iodide such as potassium iodide or sodium iodide; or crown ether.

In the present invention, among these bases, tertiary amines such as triethylamine and N,N-diisopropylethylamine are preferred, with triethylamine being particularly preferred.

Generally, the base is used in an amount of 0.1 to 15 mol, preferably about 1 to about 5 mol, with respect to 1 mol of Compound (II).

Compound (III) is preferably methanesulfonyl chloride or p-toluenesulfonyl chloride, with methanesulfonyl chloride being particularly preferred.

Generally, Compound (III) is used in an amount of 1 to 15 mol, preferably about 1 to about 5 mol, with respect to 1 mol of Compound (II).

<Step (c)>

In Step (c), Compound (V) is produced. Compound (V) may be produced through reacting Compound (IV) with an azide in a solvent in the presence or absence of a phase-transfer catalyst.

A variety of solvents may be employed. For example, hydrocarbon solvent, alcoholic solvent, ether solvent, amide solvent, cyclic urea solvent, and halohydrocarbon solvent may be employed. Examples of the hydrocarbon solvent include n-hexane, n-pentane, benzene, toluene, and xylene. Examples of the alcoholic solvent include C1-C4 alcohols such as methanol, ethanol, propanol, isopropanol (IPA), n-butanol, and t-butanol. Examples of the ether solvent include diethyl ether, diisopropyl ether (IPE), methyl t-butyl ether (MTBE), tetrahydrofuran (THF), cyclopentyl methyl ether, dimethoxyethane, and 1,4-dioxane. Examples of the amide solvent include dimethylformamide (DMF), dimethylacetamide (DMAc), and N-methyl-2-pyrrolidone (NMP). Examples of the cyclic urea solvent include 1,3-dimethyl-2-imidazolidinone (DMI) and 1,3-dimethyl-3,4,5,6-tetrahydro-2(1H)-pyrimidinone (DMPU). Examples of the halohydrocarbon solvent include chloroform, methylene chloride, and 1,2-dichloroethane (EDC). Other than these solvents, water, dimethylsulfoxide (DMSO), sulfolane, acetonitrile, (C1-C4 alkyl)acetate esters such as ethyl acetate, and acetone may be used. These solvent may be used alone or in combination of two or more species.

Among these solvents, amide solvents such as N-methyl-2-pyrrolidone (NMP) and dimethylacetamide (DMAc); cyclic urea solvents such as 1,3-dimethyl-2-imidazolidinone (DMI) and 1,3-dimethyl-3,4,5,6-tetrahydro-2(1H)-pyrimidinone (DMPU); dimethylsulfoxide; and ethyl acetate are preferred, with amide solvents such as N-methyl-2-pyrrolidone (NMP) and dimethylacetamide (DMAc) being particularly preferred.

The reaction temperature, which varies in accordance with the type of the employed solvent, is −78° C. to the boiling point of the solvent, preferably 50° to 90° C. Generally, the reaction time is 24 hours to 96 hours, preferably 60 to 75 hours.

Examples of the phase-transfer catalyst include quaternary ammonium salts such as tetramethylammonium chloride, tetraethylammonium chloride, tetrabutylammonium bromide, tetrabutylammonium chloride, tetrabutylammonium iodide, tetrabutylammonium sulfate, and trioctylmethylammonium chloride; quaternary phosphonium salts such as tetrabutylphosphonium chloride; pyridinium compounds such as dodecylpyridinium chloride; and crown ether. Of these, trioctylmethylammonium chloride, tetrabutylammonium chloride, tetrahexylammonium chloride, tetramethylammonium chloride, tetraethylammonium chloride, and dodecylpyridinium chloride are preferred, with tetrabutylammonium chloride and dodecylpyridinium chloride being particularly preferred. Generally, the catalyst is used in an amount of 0.05 to 3 mol, preferably 0.1 to 0.5 mol, with respect to 1 mol of Compound (IV).

Examples of the azide include alkali metal (e.g., sodium or potassium)azides; alkaline earth metal (e.g., calcium or magnesium)azides, and quaternary ammonium (e.g., tetrabutylammonium)azides. Of these, alkali metal azides and quaternary ammonium azides are preferred, with sodium azide being particularly preferred. Generally, the azide is used in an amount of 1 to 10 mol, preferably 1 to 3 mol, with respect to 1 mol of Compound (IV).

<Step (d)>

In Step (d), Compound (VI-I) is produced. Compound (VII) may be produced through subjecting Compound (V-I) to hydrogenolysis in a solvent in the presence of a metallic catalyst and a hydrogen source.

A variety of solvents may be employed. For example, hydrocarbon solvent, alcoholic solvent, ether solvent, amide solvent, cyclic urea solvent, and halohydrocarbon solvent may be employed. Examples of the hydrocarbon solvent include n-hexane, n-pentane, benzene, toluene, and xylene. Examples of the alcoholic solvent include C1-C4 alcohols such as methanol, ethanol, propanol, isopropanol (IPA), n-butanol, and t-butanol. Examples of the ether solvent include diethyl ether, diisopropyl ether (IPE), methyl t-butyl ether (MTBE), tetrahydrofuran (THF), cyclopentyl methyl ether, dimethoxyethane, and 1,4-dioxane. Examples of the amide solvent include dimethylformamide (DMF), dimethylacetamide (DMAc), and N-methyl-2-pyrrolidone (NMP). Examples of the cyclic urea solvent include 1,3-dimethyl-2-imidazolidinone (DMI) and 1,3-dimethyl-3,4,5,6-tetrahydro-2(1H)-pyrimidinone (DMPU). Examples of the halohydrocarbon solvent include chloroform, methylene chloride, and 1,2-dichloroethane (EDC). Other than these solvents, water, dimethylsulfoxide (DMSO), sulfolane, acetonitrile, (C1-C4 alkyl)acetate esters such as ethyl acetate, and acetone may be used. These solvent may be used alone or in combination of two or more species.

Among these solvents, C1-C4 alcoholic solvents such as methanol, ethanol, propanol, isopropanol (IPA), n-butanol, and t-butanol are preferred, with methanol and ethanol being particularly preferred.

The reaction temperature, which varies in accordance with the type of the employed solvent, is −78° C. to the boiling point of the solvent, preferably room temperature to 70° C.

Examples of the hydrogen source employed in production Step (d) include hydrazine, hydrazine hydrate, formic acid, formate salts such as sodium formate and ammonium formate, cyclohexene, and tetrahydronaphthalene. Of these, formic acid and formate salts are preferred, with ammonium formate being particularly preferred. Ammonium formate may be used in an amount of about 5 to about 10 mol with respect to 1 mol of Compound (V-I).

The catalyst which may be employed in Step (d) may be a metallic catalyst which is generally employed in such hydrogenolysis. Examples include palladium-carbon, Raney nickel, and Raney cobalt, with palladium-carbon being preferred.

Compound (VI-I) may form a salt with an acid. The acid may be an organic or inorganic acid. Examples include inorganic acids such as hydrochloric acid and sulfuric acid; carboxylic acids such as formic acid, acetic acid, oxalic acid, maleic acid, fumaric acid, malonic acid, benzoic acid, and malic acid; and sulfonic acids such as tosylic acid. Of these, maleic acid, fumaric acid, oxalic acid, and tosylic acid are preferred, with oxalic acid being particularly preferred.

A variety of solvents may be employed in the formation of the salt with an acid. For example, hydrocarbon solvent, alcoholic solvent, ether solvent, amide solvent, cyclic urea solvent, and halohydrocarbon solvent may be employed. Examples of the hydrocarbon solvent include n-hexane, n-pentane, benzene, toluene, and xylene. Examples of the alcoholic solvent include C1-C4 alcohols such as methanol, ethanol, propanol, isopropanol (IPA), n-butanol, and t-butanol. Examples of the ether solvent include diethyl ether, diisopropyl ether (IPE), methyl t-butyl ether (MTBE), tetrahydrofuran (THF), cyclopentyl methyl ether, dimethoxyethane, and 1,4-dioxane. Examples of the amide solvent include dimethylformamide (DMF), dimethylacetamide (DMAc), and N-methyl-2-pyrrolidone (NMP). Examples of the cyclic urea solvent include 1,3-dimethyl-2-imidazolidinone (DMI) and 1,3-dimethyl-3,4,5,6-tetrahydro-2(1H)-pyrimidinone (DMPU). Examples of the halohydrocarbon solvent include chloroform, methylene chloride, and 1,2-dichloroethane (EDC). Other than these solvents, water, dimethylsulfoxide (DMSO), sulfolane, acetonitrile, (C1-C6 alkyl)acetate esters, and acetone may be used. These solvent may be used alone or in combination of two or more species.

Among these solvents, acetonitrile and ethyl acetate are preferred, with acetonitrile being particularly preferred.

The salt formation temperature, which varies in accordance with the type of the employed solvent, is −78° C. to the boiling point of the solvent, preferably 10° to 50° C.

The acid may be used in an amount of about 1 to about 3 mol with respect to 1 mol of Compound (VI-I).

<Step (e)>

In Step (e), Compound (VI-II) is produced. Compound (VI-II) may be produced through subjecting compound (V-II) to hydrogenolysis in a solvent in the presence of a metallic catalyst and a hydrogen source.

A variety of solvents may be employed. For example, hydrocarbon solvent, alcoholic solvent, ether solvent, amide solvent, cyclic urea solvent, and halohydrocarbon solvent may be employed. Examples of the hydrocarbon solvent include n-hexane, n-pentane, benzene, toluene, and xylene. Examples of the alcoholic solvent include C1-C4 alcohols such as methanol, ethanol, propanol, isopropanol (IPA), n-butanol, and t-butanol. Examples of the ether solvent include diethyl ether, diisopropyl ether (IPE), methyl t-butyl ether (MTBE), tetrahydrofuran (THF), cyclopentyl methyl ether, dimethoxyethane, and 1,4-dioxane. Examples of the amide solvent include dimethylformamide (DMF), dimethylacetamide (DMAc), and N-methyl-2-pyrrolidone (NMP). Examples of the cyclic urea solvent include 1,3-dimethyl-2-imidazolidinone (DMI) and 1,3-dimethyl-3,4,5,6-tetrahydro-2(1H)-pyrimidinone (DMPU). Examples of the halohydrocarbon solvent include chloroform, methylene chloride, and 1,2-dichloroethane (EDC). Other than these solvents, water, dimethylsulfoxide (DMSO), sulfolane, acetonitrile, (C1-C4 alkyl)acetate esters such as ethyl acetate, and acetone may be used. These solvent may be used alone or in combination of two or more species.

Among these solvents, C1-C4 alcoholic solvents such as methanol, ethanol, propanol, isopropanol (IPA), n-butanol, and t-butanol are preferred, with ethanol being particularly preferred.

The reaction temperature, which varies in accordance with the type of the employed solvent, is −78° C. to the boiling point of the solvent, preferably room temperature to 70° C.

Examples of the hydrogen source employed in production Step (e) include hydrazine, hydrazine hydrate, formic acid, formate salts such as sodium formate and ammonium formate, cyclohexene, and tetrahydronaphthalene. Of these, formic acid and formate salts are preferred, with ammonium formate being particularly preferred. Ammonium formate may be used in an amount of about 5 to about 10 mol with respect to 1 mol of Compound (V-I).

The catalyst which may be employed in Step (e) may be a metallic catalyst which is generally employed in such hydrogenolysis. Examples include palladium-carbon, Raney nickel, and Raney cobalt, with palladium-carbon being preferred.

Compound (VI-II) may form a salt with an acid. The acid may be an organic or inorganic acid. Examples include inorganic acids such as hydrochloric acid and sulfuric acid; carboxylic acids such as formic acid, acetic acid, oxalic acid, maleic acid, fumaric acid, malonic acid, benzoic acid, and malic acid; and sulfonic acids such as tosylic acid. Of these maleic acid, fumaric acid, oxalic acid, and tosylic acid are preferred, with oxalic acid being particularly preferred.

A variety of solvents may be employed in the formation of the salt with an acid. For example, hydrocarbon solvent, alcoholic solvent, ether solvent, amide solvent, cyclic urea solvent, and halohydrocarbon solvent may be employed. Examples of the hydrocarbon solvent include n-hexane, n-pentane, benzene, toluene, and xylene. Examples of the alcoholic solvent include C1-C4 alcohols such as methanol, ethanol, propanol, isopropanol (IPA), n-butanol, and t-butanol. Examples of the ether solvent include diethyl ether, diisopropyl ether (IPE), methyl t-butyl ether (MTBE), tetrahydrofuran (THF), cyclopentyl methyl ether, dimethoxyethane, and 1,4-dioxane. Examples of the amide solvent include dimethylformamide (DMF), dimethylacetamide (DMAc), and N-methyl-2-pyrrolidone (NMP). Examples of the cyclic urea solvent include 1,3-dimethyl-2-imidazolidinone (DMI) and 1,3-dimethyl-3,4,5,6-tetrahydro-2(1H)-pyrimidinone (DMPU). Examples of the halohydrocarbon solvent include chloroform, methylene chloride, and 1,2-dichloroethane (EDC). Other than these solvents, water, dimethylsulfoxide (DMSO), sulfolane, acetonitrile, (C1-C4 alkyl)acetate esters, and acetone may be used. These solvent may be used alone or in combination of two or more species.

Among these solvents, acetonitrile and ethyl acetate are preferred, with ethyl acetate being particularly preferred.

The salt formation temperature, which varies in accordance with the type of the employed solvent, is −78° C. to the boiling point of the solvent, preferably 10° to 50° C.

The acid may be used in an amount of about 1 to about 3 mol with respect to 1 mol of Compound (VI-II).

<Step (f)>

In Step (f), Compound (VII) is produced. Compound (VII) may be produced through treating Compound (VI-II) or a salt thereof with benzyloxycarbonyl halide in a solvent in the presence of a base.

A variety of solvents may be employed. For example, hydrocarbon solvent, alcoholic solvent, ether solvent, amide solvent, cyclic urea solvent, and halohydrocarbon solvent may be employed. Examples of the hydrocarbon solvent include n-hexane, n-pentane, benzene, toluene, and xylene. Examples of the alcoholic solvent include C1-C4 alcohols such as methanol, ethanol, propanol, isopropanol (IPA), n-butanol, and t-butanol. Examples of the ether solvent include diethyl ether, diisopropyl ether (IPE), methyl t-butyl ether (MTBE), tetrahydrofuran (THF), cyclopentyl methyl ether, dimethoxyethane, and 1,4-dioxane. Examples of the amide solvent include dimethylformamide (DMF), dimethylacetamide (DMAc), and N-methyl-2-pyrrolidone (NMP). Examples of the cyclic urea solvent include 1,3-dimethyl-2-imidazolidinone (DMI) and 1,3-dimethyl-3,4,5,6-tetrahydro-2(1H)-pyrimidinone (DMPU). Examples of the halohydrocarbon solvent include chloroform, methylene chloride, and 1,2-dichloroethane (EDC). Other than these solvents, water, dimethylsulfoxide (DMSO), sulfolane, acetonitrile, (C1-C4 alkyl)acetate esters such as ethyl acetate, and acetone may be used. These solvent may be used alone or in combination of two or more species.

Among these solvents, C1-C4 alcohol solvents such as methanol, ethanol, propanol, isopropanol (IPA), n-butanol, and t-butanol; tetrahydrofuran; and ethyl acetate are preferred, with tetrahydrofuran and ethyl acetate being particularly preferred.

The reaction temperature, which varies in accordance with the type of the employed solvent, is −78° C. to the boiling point of the solvent, preferably 0° C. to room temperature. The reaction time is 15 minutes to 24 hours, preferably 30 minutes to 3 hours.

The base may be an organic base or an inorganic base. Examples of the base which may be employed in Step (f) include hydroxides, carbonates, hydrogencarbonates, and alkoxides of an alkali metal or an alkaline earth metal (e.g., sodium, potassium, lithium, magnesium, or calcium); metal hydrides such as sodium hydride, potassium hydride, lithium hydride; alkyllithium reagents such as n-butyllithium, methyllithium, and lithium diisopropylamide; tertiary amines such as triethylamine and N,N-diisopropylethylamine; and heterocyclic compound such as 1,8-diazabicyclo[5.4.0]undec-7-ene (DBU), 1,8-diazabicyclo[4.3.0]non-5-ene (DBN), dimethylaniline, and N-methylmorpholine.

Among these bases, alkali metal or alkaline earth metal hydrogencarbonates (e.g., sodium hydrogencarbonate), alkali metal or alkaline earth metal carbonates (e.g., potassium carbonate), and alkali metal or alkaline earth metal hydroxides (e.g., potassium hydroxide), are preferred. These bases may be used in the form of aqueous solution.

Generally, the base is used in an amount of 1 to 30 mol, preferably about 1 to about 5 mol, with respect to 1 mol of Compound (VI-II) or a salt thereof.

The benzyloxycarbonyl halide is preferably benzyloxycarbonyl chloride. Generally, benzyloxycarbonyl halide is preferably used in an amount of 1 to 10 mol, particularly preferably 1 to 2 mol, with respect to 1 mol of Compound (VI-II) or a salt thereof.

<Step (g)>

In Step (g), Compound (VIII) is produced. Compound (VIII) may be produced through treating Compound (VII) with a base in a solvent and, subsequently, (1) condensing the resultant product with a di(C1-C6 alkyl)amine; (2) condensing the resultant product with hydrazine to form a carbohydrazide, transforming the carbohydrazide to a corresponding acyl equivalent by use of an acylating agent in the presence or absence of an acid, and treating the acyl equivalent in the presence or absence of a dehydrating agent; or (3) condensing the resultant product with ammonia to form a carbamide, treating the carbamide with a dehydrating agent to form a nitrile derivative, treating the derivative with hydroxylamine to form an amidoxime, and treating the amidoxime with an acylating agent in the presence or absence of a dehydrating agent or an acid.

A variety of solvents may be employed in the condensation with dimethylamine, hydrazine, or ammonia. For example, hydrocarbon solvent, alcoholic solvent, ether solvent, amide solvent, cyclic urea solvent, and halohydrocarbon solvent may be employed. Examples of the hydrocarbon solvent include n-hexane, n-pentane, benzene, toluene, and xylene. Examples of the alcoholic solvent include C1-C4 alcohols such as methanol, ethanol, propanol, isopropanol (IPA), n-butanol, and t-butanol. Examples of the ether solvent include diethyl ether, diisopropyl ether (IPE), methyl t-butyl ether (MTBE), tetrahydrofuran (THF), cyclopentyl methyl ether, dimethoxyethane, and 1,4-dioxane. Examples of the amide solvent include dimethylformamide (DMF), dimethylacetamide (DMAc), and N-methyl-2-pyrrolidone (NMP). Examples of the cyclic urea solvent include 1,3-dimethyl-2-imidazolidinone (DMI) and 1,3-dimethyl-3,4,5,6-tetrahydro-2(1H)-pyrimidinone (DMPU). Examples of the halohydrocarbon solvent include chloroform, methylene chloride, and 1,2-dichloroethane (EDC). Other than these solvents, water, dimethylsulfoxide (DMSO), sulfolane, acetonitrile, (C1-C4 alkyl)acetate esters such as ethyl acetate, and acetone may be used. These solvent may be used alone or in combination of two or more species.

Among these solvents, C1-C4 alcohol solvents such as methanol, ethanol, propanol, isopropanol (IPA), n-butanol, and t-butanol; amide solvents such as dimethylformamide (DMF), dimethylacetamide (DMAc), and N-methyl-2-pyrrolidone (NMP); and acetonitrile are preferred, with isopropanol and dimethylacetamide being particularly preferred.

In the transformation of the carbohydrazide to the acyl equivalent, a variety of solvents may be employed. Examples of the solvents include hydrocarbon solvents, alcoholic solvents, ether solvents, amide solvents, cyclic urea solvents, and halohydrocarbon solvents as described in the above. Other than these solvents, water, dimethylsulfoxide (DMSO), sulfolane, acetonitrile, (C1-C4 alkyl)acetate esters such as ethyl acetate, and acetone may be used. These solvent may be used alone or in combination of two or more species. No solvent may be used.

Among these solvents, dimethylformamide (DMF) is particularly preferred. Use of no solvent is also particularly preferred.

In the transformation of the acyl equivalent to oxadiazole, the transformation of the carbamide to the nitrile; or the transformation of amidoxime to oxadiazole, a variety of solvents may be employed. Examples of the solvents include hydrocarbon solvents, alcoholic solvents, ether solvents, amide solvents, cyclic urea solvents, and halohydrocarbon solvents as described in the above. Other than these solvents, water, dimethylsulfoxide (DMSO), sulfolane, acetonitrile, (C1-C4 alkyl)acetate esters such as ethyl acetate, and acetone may be used. These solvent may be used alone or in combination of two or more species. No solvent may be used.

Among these solvents, hydrocarbon solvents such as benzene, toluene, and xylene; and amide solvents such as dimethylformamide (DMF), dimethylacetamide (DMAc), and N-methyl-2-pyrrolidone (NMP) are preferred. Use of no solvent is also preferred. Toluene, xylene, and dimethylformamide (DMF), and no solvent are particularly preferred.

In the transformation of the nitrile to the amidoxime, a variety of solvents may be employed. Examples of the solvents include hydrocarbon solvents, alcoholic solvents, ether solvents, amide solvents, cyclic urea solvents, and halohydrocarbon solvents as described in the above. Other than these solvents, water, dimethylsulfoxide (DMSO), sulfolane, acetonitrile, (C1-C4 alkyl)acetate esters such as ethyl acetate, and acetone may be used. These solvent may be used alone or in combination of two or more species.

Among these solvents, C1-C4 alcoholic solvents such as methanol, ethanol, propanol, isopropanol (IPA), n-butanol, and t-butanol are preferred, with methanol and ethanol being particularly preferred.

In the condensation with dimethylamine, hydrazine, or aqueous ammonia, or the transformation of the carbamide to the nitrile or of the nitrile to the amidoxime, the reaction temperature, which varies in accordance with the type of the employed solvent, is −78° C. to the boiling point of the solvent, preferably 0° C. to room temperature. In the transformation of the carbohydrazide to the acyl equivalent, of the acyl equivalent to oxadiazole, or of the amidoxime to oxadiazole, the reaction temperature, which varies in accordance with the type of the employed solvent, is −78° C. to the boiling point of the solvent, preferably 100° C. to the boiling point of the solvent. The reaction time is 15 minutes to 48 hours, preferably 30 minutes to 24 hours.

The base may be an organic base or an inorganic base. Examples of the base which may be employed in Step (f) include hydroxides, carbonates, hydrogencarbonates, and alkoxides of an alkali metal or an alkaline earth metal (e.g., sodium, potassium, lithium, magnesium, or calcium); metal hydrides such as sodium hydride, potassium hydride, lithium hydride; alkyllithium reagents such as n-butyllithium, methyllithium, and lithium diisopropylamide; tertiary amines such as triethylamine and N,N-diisopropylethylamine; and heterocyclic compound such as 1,8-diazabicyclo[5.4.0]undec-7-ene (DBU), 1,8-diazabicyclo[4.3.0]non-5-ene (DBN), dimethylaniline, and N-methylmorpholine.

Among these bases, metal hydrides such as lithium hydride are preferred. These bases may be used in the form of aqueous solution. Generally, the base is used in an amount of 1 to 10 mol, preferably about 1 to about 3 mol, with respect to 1 mol of Compound (VII).

Examples of the condensing agent include 1,3-dicyclohexylcarbodiimide, isobutyl chloroformate, pyvalyl chloride, isovaleryl chloride, 1-ethyl-3-(3-dimethylaminopropyl)carbodiimide, 1-cyclohexyl-3-morpholinoethylcarbodiimide, 1-cyclohexyl-3-(4-diethylaminocyclohexyl)carbodiimide, N,N'-carbonyldiimidazole, 2-chloro-1,3-dimethylimidazolinium chloride, and isobutyl chloroformate. Of these, 1-ethyl-3-(3-dimethylaminopropyl)carbodiimide, 1-cyclohexyl-3-morpholinoethylcarbodiimide, and 1-cyclohexyl-3-(4-diethylaminocyclohexyl)carbodiimide are preferred, with 1-ethyl-3-(3-dimethylaminopropyl)carbodiimide hydrochloride being particularly preferred.

In the condensation reactions, use of an additive with the condensing agent is preferred for promoting reaction and enhancing production yield. Examples of the additive include p-nitrophenol, hydroxysuccinimide, hydroxyphthalimide, 1-hydroxybenzotriazole, 3-hydroxy-4-oxo-3,4-dihydro-1,2,3-benzotriazine, N-hydroxy-5-norbornene-2,3-dicarboximide, and 2-hydroxyimino-2-cyanoethyl acetate. Of these, hydroxysuccinimide, and 1-hydroxy-1,2,3-benzotriazole are preferred, with 1-hydroxybenzotriazole being particularly preferred. Generally, the additive(s) is used in an amount of 0.1 to 3 mol, preferably about 0.2 to about 2 mol, with respect to 1 mol of Compound (VII). The additive may be in the form of hydrate.

When dimethylamine hydrochloride is employed, a basic additive is preferably used so as to remove the formed hydrogen chloride to promote reaction. The basic additive may be used in combination with the above-mentioned additive. Examples of the basic additive include triethylamine, diisopropylethylamine, and N-methylmorpholine. Of these, triethylamine is particularly preferred.

The acid may be an organic or inorganic acid. Examples of the acid which may be used include inorganic acids such as hydrochloric acid and sulfuric acid; carboxylic acids such as formic acid, acetic acid, oxalic acid, maleic acid, fumaric acid, malonic acid, benzoic acid, and malic acid; sulfonic acids such as tosylic acid; and Lewis acids such as halides of a metal selected from among magnesium, aluminum, silane, boron, scandium, titanium(IV), chromium(II, III, or IV), manganese, iron(II or III), cobalt, nickel, copper(I or II), zinc, gallium, germanium, yttrium, zirconium, silver, cadmium, indium, tin(II or IV), antimony(III or IV), hafnium, lead, bismuth, lanthanum, cerium, and ytterbium, and trifluoromethanesulfonate (triflate) esters thereof. Of these, acetic acid, tosylic acid, zinc chloride, magnesium chloride, aluminum chloride, and boron trifluoride are preferred, with tosylic acid and boron trifluoride being particularly preferred. These acids may be in the form of hydrate and may form a complex with solvent.

Examples of the acylating agent include methyl orthoformate, ethyl orthoformate, methyl orthoacetate, ethyl orthoacetate, formic acid, dimethylformamide, dimethylformamide dimethylacetal, dimethylformamide diethylacetal, acetyl formate, and acetic anhydride. Of these, methyl orthoformate, ethyl orthoformate, formic acid, and dimethylformamide are particularly preferred. Generally, the acylating agent is used in an amount of 1 to 100 mol, preferably about 1.2 to about 10 mol, with respect to 1 mol of Compound (VII).

Examples of the dehydrating agent include diphosphorus pentoxide, phosphorus oxychloride, thionyl chloride, and trifluoroacetic anhydride. Of these, phosphorus oxychloride and thionyl chloride are particularly preferred. Generally, the dehydrating agent is used in an amount of 1 to 10 mol, preferably about 1.2 to about 3 mol, with respect to 1 mol of Compound (VII).

Examples of the di(C1-C6 alkyl)amine employed in Step (g) include dimethylamine and diethylamine. Of these, dimethylamine is particularly preferred. Generally, di(C1-C6 alkyl)amine is preferably used in an amount of 1 to 10 mol, particularly preferably 1 to 2 mol, with respect to 1 mol of Compound (VII).

<Step (h)>

In Step (h), Compound (VI-I) is produced. Compound (VI-I) may be produced through subjecting Compound (VIII) to hydrogenolysis in a solvent in the presence of a metallic catalyst.

A variety of solvents may be employed. For example, hydrocarbon solvent, alcoholic solvent, ether solvent, amide solvent, cyclic urea solvent, and halohydrocarbon solvent may be employed. Examples of the hydrocarbon solvent include n-hexane, n-pentane, benzene, toluene, and xylene. Examples of the alcoholic solvent include C1-C4 alcohols such as methanol, ethanol, propanol, isopropanol (IPA), n-butanol, and t-butanol. Examples of the ether solvent include diethyl ether, diisopropyl ether (IPE), methyl t-butyl ether (MTBE), tetrahydrofuran (THF), cyclopentyl methyl ether, dimethoxyethane, and 1,4-dioxane. Examples of the amide solvent include dimethylformamide (DMF), dimethylacetamide (DMAc), and N-methyl-2-pyrrolidone (NMP). Examples of the cyclic urea solvent include 1,3-dimethyl-2-imidazolidinone (DMI) and 1,3-dimethyl-3,4,5,6-tetrahydro-2(1H)-pyrimidinone (DMPU). Examples of the halohydrocarbon solvent include chloroform, methylene chloride, and 1,2-dichloroethane (EDC). Other than these solvents, water, dimethylsulfoxide (DMSO), sulfolane, acetonitrile, (C1-C4 alkyl)acetate esters such as ethyl acetate, and acetone may be used. These solvent may be used alone or in combination of two or more species.

Among these solvents, C1-C4 alcohol solvents such as methanol, ethanol, propanol, isopropanol (IPA), n-butanol, and t-butanol are preferred, with isopropanol being particularly preferred.

The reaction temperature, which varies in accordance with the type of the employed solvent, is −78° C. to the boiling point of the solvent, preferably room temperature to 70° C.

Examples of the hydrogen source employed in the step include hydrogen gas, hydrazine, hydrazine hydrate, formic acid, formate salts such as sodium formate and ammonium formate, cyclohexene, and tetrahydronaphthalene. Of these, hydrogen gas is preferred. The pressure of hydrogen gas may be 1 to 50 atm, with 1 to 10 atm being preferred.

The catalyst which may be employed in Step (h) may be a metallic catalyst which is generally employed in such hydrogenolysis. Examples include palladium-carbon, Raney nickel, and Raney cobalt, with palladium-carbon being preferred.

Compound (VI-I) may form a salt with an acid. The acid may be an organic or inorganic acid. Examples include inorganic acids such as hydrochloric acid and sulfuric acid; carboxylic acids such as formic acid, acetic acid, oxalic acid, maleic acid, fumaric acid, malonic acid, benzoic acid, and malic acid; and sulfonic acids such as tosylic acid. Of these maleic acid, fumaric acid, oxalic acid, and tosylic acid are preferred, with oxalic acid being particularly preferred.

A variety of solvents may be employed in the formation of the salt with an acid. For example, hydrocarbon solvent, alcoholic solvent, ether solvent, amide solvent, cyclic urea solvent, and halohydrocarbon solvent may be employed. Examples of the hydrocarbon solvent include n-hexane, n-pentane, benzene, toluene, and xylene. Examples of the alcoholic solvent include C1-C4 alcohols such as methanol, ethanol, propanol, isopropanol (IPA), n-butanol, and t-butanol. Examples of the ether solvent include diethyl ether, diisopropyl ether (IPE), methyl t-butyl ether (MTBE), tetrahydrofuran (THF), cyclopentyl methyl ether, dimethoxyethane, and 1,4-dioxane. Examples of the amide solvent include dimethylformamide (DMF), dimethylacetamide (DMAc), and N-methyl-2-pyrrolidone (NMP). Examples of the cyclic urea solvent include 1,3-dimethyl-2-imidazolidinone (DMI) and 1,3-dimethyl-3,4,5,6-tetrahydro-2(1H)-pyrimidinone (DMPU). Examples of the halohydrocarbon solvent include chloroform, methylene chloride, and 1,2-dichloroethane (EDC). Other than these solvents, water, dimethylsulfoxide (DMSO), sulfolane, acetonitrile, (C1-C4 alkyl)acetate esters, and acetone may be used. These solvent may be used alone or in combination of two or more species.

Among these solvents, acetonitrile and ethyl acetate are preferred, with acetonitrile being particularly preferred.

The salt formation temperature, which varies in accordance with the type of the employed solvent, is −78° C. to the boiling point of the solvent, preferably 10° to 50° C.

The acid may be used in an amount of about 1 to about 3 mol with respect to 1 mol of Compound (VI-I).

Compound (A) as disclosed in, for example, Patent Document 1, which exhibits an activated blood coagulation factor X inhibitory action and which is a useful preventive and therapeutic agent for thrombotic diseases, may be produced from Compound (VI-I) of the present invention as an intermediate, through the following process in accordance with a process as described in, for example, WO2004/058715.

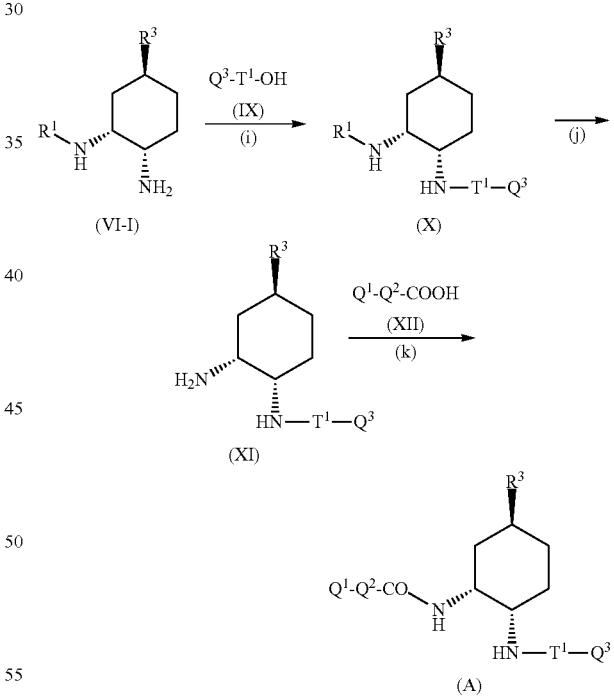

In the above scheme, $Q^1$ represents a saturated or unsaturated, 5- or 6-membered cyclic hydrocarbon group which may be substituted, a saturated or unsaturated, 5- to 7-membered heterocyclic group which may be substituted, a saturated or unsaturated, bicyclic or tricyclic condensed hydrocarbon group which may be substituted, or a saturated or unsaturated, bicyclic or tricyclic condensed heterocyclic group which may be substituted;

$Q^2$ represents a single bond, a linear or branched C1-C6 alkylene group, a linear or branched C2-C6 alkenylene group, a linear or branched C2-C6 alkynylene group, a saturated or unsaturated, 5- or 6-membered divalent cyclic hydrocarbon group which may be substituted, a saturated or unsaturated, 5- to 7-membered divalent heterocyclic group which may be substituted, a saturated or unsaturated, divalent bicyclic or tricyclic condensed hydrocarbon group which may be substituted, or a saturated or unsaturated, divalent bicyclic or tricyclic condensed heterocyclic group which may be substituted;

$Q^3$ represents an aryl group which may be substituted, an arylalkenyl group which may be substituted, an arylalkynyl group which may be substituted, a heteroaryl group which may be substituted, a heteroarylalkenyl group which may be substituted, a saturated or unsaturated, bicyclic or tricyclic condensed hydrocarbon group which may be substituted, or a saturated or unsaturated, bicyclic or tricyclic condensed heterocyclic group which may be substituted;

$T^1$ represents a carbonyl group, sulfonyl group, group —C(=O)—C(=O)—N(R')—, group —C(=S)—C(=O)—N(R')—, group —C(=O)—C(=S)—N(R')—, group —C(=S)—C(=S)—N(R')— (wherein R' represents a hydrogen atom, hydroxyl group, alkyl group or alkoxy group), group —C(=O)-$A^1$-N(R")— (wherein $A^1$ represents a C1-C5 alkylene group which may be substituted, and R" represents a hydrogen atom, hydroxyl group, alkyl group or alkoxy group), group —C(=O)—NH—, group —C(=S)—NH—, group —C(=O)—NH—NH—, group —C(=O)-$A^2$-C(=O) (wherein $A^2$ represents a single bond or C1-C5 alkylene group), group —C(=O)-$A^3$-C(=O)—NH— (wherein $A^3$ represents a C1-C5 alkylene group), group —C(=O)—C(=NOR$^a$)—N(R$^b$)—, group —C(=S)—C(=NOR$^a$)—N(R$^b$) (wherein R$^a$ represents a hydrogen atom, alkyl group, or alkanoyl group, and R$^b$ represents a hydrogen atom, hydroxyl group, alkyl group, or alkoxy group), group —C(=O)—N=N—, group —C(=S)—N=N—, group —C(=NOR$^c$)—C(=O)—N(R$^d$)— (wherein R$^c$ represents a hydrogen atom, alkyl group, alkanoyl group, aryl group, or aralkyl group, and R$^d$ represents a hydrogen atom, hydroxyl group, alkyl group or alkoxy group), group —C(=N—N(R$^e$)(R$^f$))—C(=O)—N(R$^g$)— (wherein R$^e$ and R$^f$ each independently represent a hydrogen atom, alkyl group, alkanoyl group or alkyl(thiocarbonyl) group, and R$^g$ represents a hydrogen atom, hydroxyl group, alkyl group or alkoxy group), group —C(=O)—NH—C(=O)—, group —C(=S)—NH—C(=O)—, group —C(=O)—NH—C(=S)—, group —C(=S)—NHC(=S)—, group —C(=O)—NH—SO$_2$—, group —SO$_2$—NH—, group —C(=NCN)—NH—C(=O)—, group —C(=S)—C(=O)—, or thiocarbonyl group; and $R^1$ and $R^3$ have the same meanings as defined above.

That is, the intermediate compound (VI-I) is reacted with Compound (IX) or a salt thereof, and the protective group of the formed Compound (X) is removed. Subsequently, the deprotected compound is reacted with a carboxylic acid (XII) or a salt thereof under the same conditions, to thereby produce Compound (A).

The substituents involved in the above reaction steps will next be described.

In the group $Q^3$, the aryl group may include C6-C14 aryl groups, for example, phenyl, naphthyl, anthryl and phenanthryl groups. The arylalkenyl group means a group formed by a C6-C14 aryl group and a C2-C6 alkenylene group, and examples thereof may include a styryl group. The arylalkynyl group means a group formed by a C6-C14 aryl group and a C2-C6 alkynylene group, and examples thereof may include a phenylethynyl group.

The heteroaryl group means a monovalent aromatic group having at least one hetero atom selected from oxygen, sulfur and nitrogen atoms, and examples thereof may include 5- or 6-membered heteroaryl groups, for example, pyridyl, pyridazinyl, pyrazinyl, furyl, thienyl, pyrrolyl, thiazolyl, oxazolyl, pyrimidinyl and tetrazolyl groups. The heteroarylalkenyl group means a group formed by the above-described heteroaryl group and a C2-C6 alkenylene group, and examples thereof may include thienylethenyl and pyridylethenyl groups.

The saturated or unsaturated, bicyclic or tricyclic condensed hydrocarbon group means a monovalent group derived from a saturated or unsaturated, bicyclic or tricyclic condensed hydrocarbon. The saturated or unsaturated, bicyclic or tricyclic condensed hydrocarbon denotes a bicyclic or tricyclic condensed hydrocarbon formed by condensing 2 or 3 saturated or unsaturated, 5- or 6-membered cyclic hydrocarbons which are the same or different from each other. In this case, examples of the saturated or unsaturated, 5- or 6-membered cyclic hydrocarbons may include cyclopentane, cyclopentene, cyclohexane, cyclohexene, cyclohexadiene and benzene. Specific examples of the saturated or unsaturated, bicyclic or tricyclic condensed hydrocarbon group may include indenyl, indanyl, tetrahydronaphthyl and naphthyl groups. Incidentally, the position of the saturated or unsaturated, bicyclic or tricyclic condensed hydrocarbon group bonded to $T^1$ is not particularly limited.

The saturated or unsaturated, bicyclic or tricyclic condensed heterocyclic group means a monovalent group derived from a saturated or unsaturated, bicyclic or tricyclic condensed heterocyclic ring. The saturated or unsaturated, bicyclic or tricyclic condensed heterocyclic ring denotes the following heterocyclic ring 1), 2), or 3):

1) a bicyclic or tricyclic condensed heterocyclic ring formed by condensing 2 or 3 saturated or unsaturated, 5- to 7-membered heterocyclic rings which are the same or different from one another;

2) a bicyclic or tricyclic condensed heterocyclic ring formed by condensing one saturated or unsaturated, 5- to 7-membered heterocyclic ring with 1 or 2 saturated or unsaturated, 5- or 6-membered cyclic hydrocarbons; or 3) a tricyclic condensed heterocyclic ring formed by condensing two saturated or unsaturated, 5- to 7-membered heterocyclic rings with a saturated or unsaturated, 5- or 6-membered cyclic hydrocarbon.

The position of the saturated or unsaturated, bicyclic or tricyclic condensed heterocyclic group bonded to $T^1$ is not particularly limited.

The saturated or unsaturated, 5- to 7-membered heterocyclic ring denotes a heterocyclic ring having at least one hetero atom selected from oxygen, sulfur and nitrogen atoms, and specific examples thereof may include furan, pyrrole, thiophene, pyrazole, imidazole, oxazole, oxazolidine, thiazole, thiadiazole, furazane, pyrane, pyridine, pyrimidine, pyridazine, pyrrolidine, piperazine, piperidine, oxazine, oxadiazine, morpholine, thiazine, thiadiazine, thiomorpholine, tetrazole, triazole, triazine, thiadiazine, oxadiazine, azepine, diazepine, triazepine, thiazepine and oxazepine. The saturated or unsaturated, 5- or 6-membered cyclic hydrocarbon denotes the same saturated or unsaturated, 5- or 6-membered cyclic hydrocarbon as shown in the description of the saturated or unsaturated, bicyclic or tricyclic condensed hydrocarbon group. Specific examples of the saturated or unsaturated, bicyclic or tricyclic condensed heterocyclic group may include benzofuryl, isobenzofuryl, benzothienyl, indolyl, indolinyl, isoindolyl, isoindolinyl, indazolyl, quinolyl, dihydroquinolyl, 4-oxodihydroquinolyl (dihydroquinolin-4-on), tetrahydroquinolyl, isoquinolyl, tetrahydro-isoquinolyl, chromenyl, chromanyl, isochromanyl, 4H-4-oxobenzopyranyl, 3,4-dihydro-4H-4-oxobenzopyranyl, 4H-quinolizinyl, quinazolinyl, dihydroquinazolinyl, tetrahydroquinazolinyl, quinoxalinyl, tetrahydroquinoxalinyl, cinnolinyl, tetrahydrocinnolinyl, indolizinyl, tetrahydroindolizinyl, benzothiazolyl, tetrahydrobenzothiazolyl, benzoxazolyl, benzisothiazolyl, benzisoxazolyl, benzimidazolyl, naphthyridinyl, tetrahydronaphthyridinyl, thienopyridyl, tetrahydrothienopyridyl, thiazolopyridyl, tetrahydrothiazolopyridyl, thiazolopyridazinyl, tetrahydrothiazolopyridazinyl, pyrrolopyridyl, dihydropyrrolopyridyl, tetrahydropyrrolopyridyl, pyrrolopyrimidinyl, dihydropyrrolopyrimidinyl, pyridoquinazolinyl, dihydropyridoquinazolinyl, pyridopyrimidinyl, tetrahydropyridopyrimidinyl, pyranothiazolyl, dihydropyranothiazolyl, furopyridyl, tetrahydro-furopyridyl, oxazolopyridyl, tetrahydroxazolopyridyl, oxazolopyridazinyl, tetrahydroxazolopyridazinyl, pyrrolothiazolyl, dihydropyrrolothiazolyl, pyrrolooxazolyl, dihydropyrrolooxazolyl, thienopyrrolyl, thiazolopyrimidinyl, 4-oxotetrahydrocinnolinyl, 1,2,4-benzothiadiazinyl, 1,1-dioxy-2H-1,2,4-benzothiadiazinyl, 1,2,4-benzoxadiazinyl, cyclopentapyranyl, thienofuranyl, furopyranyl, pyridoxazinyl, pyrazoloxazolyl, imidazothiazolyl, imidazopyridyl, tetrahydroimidazo-pyridyl, pyrazinopyridazinyl, benzisoquinolyl, furocinnolyl, pyrazolothiazolopyridazinyl, tetrahydropyrazolothiazolopyridazinyl, hexahydrothiazolopyridazinopyridazinyl, imidazotriazinyl, oxazolopyridyl, benzoxepinyl, benzazepinyl, tetrahydrobenzazepinyl, benzodiazepinyl, benzotriazepinyl, thienoazepinyl, tetrahydrothienoazepinyl, thienodiazepinyl, thienotriazepinyl, thiazoloazepinyl, tetrahydrothiazoloazepinyl, 4,5,6,7-tetrahydro-5,6-tetramethylenethiazolopyridazinyl and 5,6-trimethylene-4,5,6,7-tetrahydrothiazolopyridazinyl groups.

No particular limitation is imposed on the condensing form of the condensed heterocyclic group. For example, the naphthyridinyl group may be any of 1,5-, 1,6-, 1,7-, 1,8-, 2,6- and 2,7-naphthyridinyl groups, the thienopyridyl group may be any of thieno[2,3-b]pyridyl, thieno[2,3-c]pyridyl, thieno[3,2-b]pyridyl, thieno[3,2-c]pyridyl, thieno[3,4-b]pyridyl and thieno[3,4-c]pyridyl groups, the thienopyrrolyl group may be any of thieno[2,3-b]pyrrolyl and thieno[2,3-b]pyrrolyl groups, the thiazolopyridyl group may be any of thiazolo[4,5-b]pyridyl, thiazolo[4,5-c]pyridyl, thiazolo[5,4-b]pyridyl, thiazolo[5,4-c]pyridyl, thiazolo[3,4-a]pyridyl and thiazolo[3,2-a]pyridyl groups, the thiazolopyridazinyl group may be any of thiazolo[4,5-c]pyridazinyl, thiazolo[4,5-d]pyridazinyl, thiazolo[5,4-c]pyridazinyl and thiazolo[3,2-b]pyridazinyl groups, the pyrrolopyridyl group may be any of pyrrolo[2,3-b]pyridyl, pyrrolo[2,3-c]pyridyl, pyrrolo[3,2-b]pyridyl, pyrrolo[3,2-c]pyridyl, pyrrolo[3,4-b]pyridyl and pyrrolo[3,4-c]pyridyl group, the pyridopyrimidinyl group may be any of pyrido[2,3-d]pyrimidinyl, pyrido[3,2-d]pyrimidinyl, pyrido[3,4-d]pyrimidinyl, pyrido[4,3-d]pyrimidinyl, pyrido[1,2-c]pyrimidinyl and pyrido[1,2-a]pyrimidinyl groups, the pyranothiazolyl group may be any of pyrano[2,3-d]thiazolyl, pyrano[4,3-d]thiazolyl, pyrano[3,4-d]thiazolyl and pyrano[3,2-d]thiazolyl groups, the furopyridyl group may be any of furo[2,3-b]pyridyl, furo[2,3-c]pyridyl, furo[3,2-b]pyridyl, furo[3,2-c]pyridyl, furo[3,4-b]pyridyl and furo[3,4-c]pyridyl groups, the oxazolopyridyl group may be any of oxazolo[4,5-b]pyridyl, oxazolo[4,5-c]pyridyl, oxazolo[5,4-b]pyridyl, oxazolo[5,4-c]pyridyl, oxazolo[3,4-a]pyridyl and oxazolo[3,2-a]pyridyl groups, the oxazolopyridazinyl group may be any of oxazolo[4,5-c]pyridazinyl, oxazolo[4,5-d]pyridazinyl, oxazolo[5,4-c]pyridazinyl and oxazolo[3,4-b]pyridazinyl groups, the pyrrolothiazolyl group may be any of pyrrolo[2,1-b]thiazolyl, pyrrolo[1,2-c]thiazolyl, pyrrolo[2,3-d]thiazolyl, pyrrolo[3,2-d]thiazolyl and pyrrolo[3,4-d]thiazolyl groups, the pyrrolooxazolyl group may be any of pyrrolo[2,1-b]oxazolyl, pyrrolo[1,2-c]oxazolyl, pyrrolo[2,3-d]oxazolyl, pyrrolo[3,2-d]oxazolyl and pyrrolo[3,4-d]oxazolyl groups, the benzazepinyl group may be any of 1H-1-benzazepinyl, 1H-2-benzazepinyl and 1H-3-benzazepinyl groups, or may be a dihydro-oxo derivative type benzazepinyl group such as 4,5-dihydro-1-oxo-1H-2-benzazepinyl group, the benzodiazepinyl group may be any of 1H-1,3-benzodiazepinyl, 1H-1,4-benzodiazepinyl and 1H-1,5-benzodiazepinyl groups, or may be a dihydro-oxo derivative type benzodiazepinyl group such as 4,5-dihydro-4-oxo-1H-1,3-benzodiazepinyl group, the benzotriazepinyl group may be any of 1H-1,3,4-benzotriazepinyl and 1H-1,3,5-benzotriazepinyl groups, or may be a dihydro-oxo derivative type benzotriazepinyl group such as 4,5-dihydro-5-oxo-1H-1,3,4-benzotriazepinyl group, and the thienoazepinyl group may be any of thieno[2,3-b]azepinyl, thieno[2,3-c]azepinyl, thieno[2,3-d]azepinyl, thieno[3,2-c]azepinyl and thieno[3,2-b]azepinyl groups, or may be a dihydro-oxo derivative type thienoazepinyl group such as 5,6,7,8-tetrahydro-4-oxo-4H-thieno[3,2-c]azepinyl group. Thienodiazepinyl and thienotriazepinyl groups may also be any condensing forms, or may be those of the dihydro-oxo derivative type. The benzothiazepinyl group may be any of 1H-1-benzothiazepinyl, 1H-2-benzothiazepinyl and 1H-3-benzothiazepinyl groups, or may be a dihydro-oxo derivative type benzothiazepinyl group such as 4,5-dihydro-1-oxo-1H-2-benzothiazepinyl group, and the benzoxazepinyl group may be any of 1H-1-benzoxazepinyl, 1H-2-benzoxazepinyl and 1H-3-benzoxazepinyl groups, or may be a dihydro-oxo derivative type benzoxazepinyl group such as 4,5-dihydro-1-oxo-1H-2-benzoxazepinyl group. Other condensing forms than these may be allowed.

The above-described aryl groups, heteroaryl groups, arylalkenyl group, heteroarylalkenyl groups, saturated or unsaturated, bicyclic or tricyclic condensed hydrocarbon groups and saturated or unsaturated, bicyclic or tricyclic condensed heterocyclic groups may each have 1 to 3 substituents. Examples of the substituents may include a hydroxyl group, halogen atoms such as fluorine atom, chlorine atom, bromine atom and iodine atom, C1-C6 halogenoalkyl groups substituted by 1 to 3 halogen atoms, an amino group, a cyano group, aminoalkyl groups, a nitro group, hydroxyalkyl groups (for example, hydroxymethyl group, 2-hydroxyethyl group, etc.), alkoxyalkyl groups (for example, methoxymethyl group, 2-methoxyethyl group, etc.), a carboxyl group, carboxyalkyl groups (for example, carboxymethyl group, 2-carboxyethyl group, etc.), alkoxycarbonylalkyl groups (for example, methoxycarbonylmethyl group, ethoxycarbonylmethyl group, etc.), acyl groups (for example, alkanoyl groups such as formyl group, acetyl group and propionyl group), an amidino group, a hydroxyamidino group (amino(hydroxyimino)methyl group), linear, branched or cyclic C1-C6 alkyl groups (for example, methyl group, ethyl group, etc.), linear, branched or cyclic C1-C6 alkoxy groups (for example, methoxy group, ethoxy group, etc.), amidino groups substituted by a linear, branched or cyclic C1-C6 alkyl group (for example, imino(methylamino)methyl group), amidino groups substituted by a linear, branched or cyclic C1-C6 alkoxy group (for example, amino(methoxyimino)methyl group), amidino groups substituted by a linear, branched or cyclic C2-C7 alkoxycarbonyl group (for example, amino(methoxycarbonylimino)methyl group and amino(ethoxycarbonylimino)methyl group), linear, branched or cyclic C2-C6 alkenyl groups (for example, vinyl group, allyl group, etc.), linear or branched C2-C6 alkynyl groups (for example, ethynyl group, propynyl group, etc.), linear, branched or cyclic C2-C6 alkoxycarbonyl groups (for example, methoxycarbonyl group, ethoxycarbonyl group, etc.), a carbamoyl group, mono- or di-alkylcarbamoyl groups substituted by a linear, branched or cyclic C1-C6 alkyl group on the nitrogen atom(s) (for example, methylcarbamoyl group, ethylcarbamoyl group, dimethylcarbamoyl group, ethylmethylcarbamoyl group, etc.), mono- or di-alkylamino groups substituted by a linear, branched or cyclic C1-C6 alkyl group (for example, ethylamino, dimethylamino and methylethylamino groups), and 5- or 6-membered nitrogen-containing heterocyclic groups (for example, pyrrolidino group, piperidino group, piperazino group, morpholino group, etc.).

As the group $Q^3$, are preferred the following 12 groups (a) to (l) among the above-described groups. Namely,

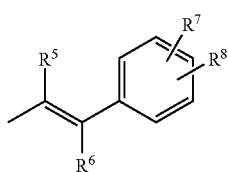
(a)

(wherein $R^5$ and $R^6$ each independently represent a hydrogen atom, cyano group, halogen atom, alkyl group, hydroxyalkyl group, alkoxy group, alkoxyalkyl group, carboxyl group, carboxyalkyl group, acyl group, alkoxycarbonyl group, alkoxycarbonylalkyl group, or phenyl group which may be substituted by a cyano group, hydroxyl group, halogen atom, alkyl group or alkoxy group, and $R^7$ and $R^8$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group);

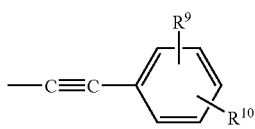
(b)

(wherein $R^9$ and $R^{10}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group);

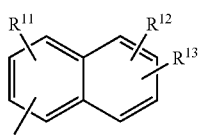
(c)

(wherein $R^{11}$, $R^{12}$ and $R^{13}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group);

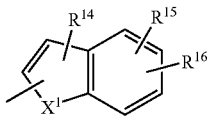
(d)

(wherein $X^1$ represents $CH_2$, CH, NH, NOH, N, O or S, and $R^{14}$, $R^{15}$ and $R^{16}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group);

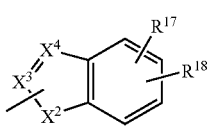
(e)

(wherein $X^2$ represents NH, N, O or S, $X^3$ represents N, C or CH, $X^4$ represents N, C or CH, and $R^{17}$ and $R^{18}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group, excluding the cases where $X^3$ and $X^4$ are combinations of C and CH, and are both C or CH);

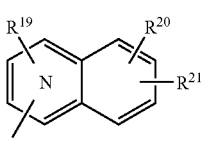
(f)

(wherein N indicates that 1 or 2 carbon atoms of the ring substituted by $R^{19}$ have been substituted by a nitrogen atom, and $R^{19}$, $R^{20}$ and $R^{21}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group);

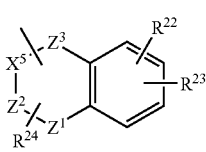
(g)

(wherein $X^5$ represents $CH_2$, CH, N or NH, $Z^1$ represents N, NH or O, $Z^2$ represents $CH_2$, CH, C or N, $Z^3$ represents $CH_2$, CH, S, $SO_2$ or C=O, $X^5$—$Z^2$ indicates that $X^5$ and $Z^2$ are bonded to each other by a single bond or double bond, $R^{22}$ and $R^{23}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group, and $R^{24}$ represents a hydrogen atom or alkyl group);

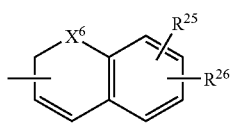

(h)

(wherein $X^6$ represents O or S, and $R^{25}$ and $R^{26}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group);

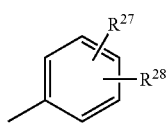

(i)

(wherein $R^{27}$ and $R^{28}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group);

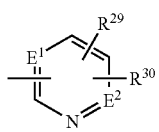

(j)

(wherein $E^1$ and $E^2$ each independently represent N or CH, and $R^{29}$ and $R^{30}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group);

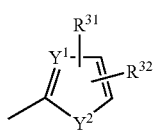

(k)

(wherein $Y^1$ represents CH or N, $Y^2$ represents —N($R^{33}$)— (in which $R^{33}$ represents a hydrogen atom or C1-C6 alkyl group), O or S, and $R^{31}$ and $R^{32}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group); and the following group

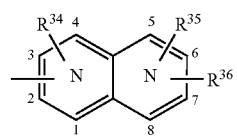

(1)

(wherein numerals 1 to 8 indicate locants, each N indicates that any one of carbon atoms of positions 1 to 4 and any one of carbon atoms of positions 5 to 8 has been substituted by a nitrogen atom, and $R^{34}$, $R^{35}$ and $R^{36}$ each independently represent a hydrogen atom, hydroxyl group, nitro group, amino group, cyano group, halogen atom, alkyl group, alkenyl group, alkynyl group, halogenoalkyl group, hydroxyalkyl group, alkoxy group, alkoxyalkyl group, carboxyl group, carboxyalkyl group, acyl group, carbamoyl group, N-alkylcarbamoyl group, N,N-dialkylcarbamoyl group, alkoxycarbonyl group, amidino group or alkoxycarbonylalkyl group).

These groups will hereinafter be described.

In the description of $R^5$ to $R^{36}$, the halogen atom is a fluorine, chlorine, bromine or iodine atom, the alkyl group is a linear, branched or cyclic C1-C6 alkyl group, the alkenyl group is a linear, branched or cyclic C2-C6 alkenyl group, the alkynyl group is a linear or branched C2-C6 alkynyl group, the hydroxyalkyl group means the above-described C1-C6 alkyl group substituted by one hydroxyl group, the alkoxy group is a linear, branched or cyclic C1-C6 alkoxy group, the alkoxyalkyl group means the above-described C1-C6 alkyl group substituted by one C1-C6 alkoxy group mentioned above, the carboxyalkyl group means the above-described C1-C6 alkyl group substituted by one carboxyl group, the acyl group is a C1-C6 alkanoyl group (including formyl), an aroyl group such as a benzoyl or naphthoyl group, or an arylalkanoyl group with the above-described C6-C14 aryl group substituted on the above-described $C_1$-$C_6$ alkanoyl group, the N-alkylcarbamoyl group means a carbamoyl group with the above-described $C_1$-$C_6$ alkyl group substituted on the nitrogen atom, the N,N-dialkylcarbamoyl group means a carbamoyl group with two $C_1$-$C_6$ alkyl groups substituted on the nitrogen atom, the alkoxycarbonyl group is a group composed of the above-described $C_1$-$C_6$ alkoxy group and a carbonyl group, the alkoxycarbonylalkyl group means the above-described $C_1$-$C_6$ alkyl group substituted by one $C_1$-$C_6$ alkoxycarbonyl group, and the halogenoalkyl group means the above-described $C_1$-$C_6$ alkyl group substituted by 1 to 3 halogen atoms. Incidentally, in the above description, no particular limitation is imposed on the substituting position.

In the following group:
In the group:

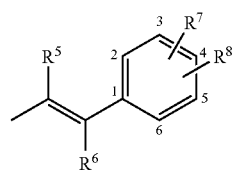

(a)

(wherein $R^5$, $R^6$, $R^7$ and $R^8$ have the same meanings as defined above, and numerals 1 to 6 indicate locants), $R^5$ and $R^6$ are each independently preferably a hydrogen atom, cyano group, halogen atom, alkyl group, alkenyl group, alkynyl group, or halogenoalkyl group. $R^5$ and $R^6$ are more preferably hydrogen atoms or alkyl groups. In the case of the alkyl group, a methyl group is preferred. It is preferable that one of $R^7$ and $R^8$ is a hydrogen atom, and the other is a hydrogen atom, cyano group, halogen atom, alkyl group, alkenyl group, alkynyl group, or halogenoalkyl group. Among others, it is particularly preferred that the other group be a hydrogen atom, halogen atom, alkyl group, or alkynyl group. In this case, the halogen atom is preferably a fluorine, chlorine or bromine atom. As the alkyl group, is preferred a methyl group. As the alkynyl group, is particularly preferred an ethynyl group. As specific preferable examples of the group represented by the above formula, may be mentioned chlorostyryl, fluorostyryl, bromostyryl, and ethynylstyryl groups. The position in the group substituted by the halogen atom, alkyl group, or alkynyl group is particularly preferably a 4-position in the above formula though it should not be particularly limited. As specific preferable examples thereof, may be mentioned 4-chlorostyryl, 4-fluorostyryl, 4-bromostyryl, and 4-ethynylstyryl groups.

In the following group:

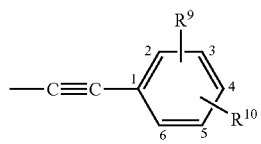

(b)

(wherein $R^9$ and $R^{10}$ have the same meanings as defined above, and numerals 1 to 6 indicate locants), $R^9$ and $R^{10}$ are each independently preferably a hydrogen atom, halogen atom, alkyl group, or alkynyl group. It is further preferable that $R^9$ is a hydrogen atom, and $R^{10}$ is a hydrogen atom, halogen atom, alkyl group, or alkynyl group. In this case, the halogen atom is preferably a fluorine, chlorine or bromine atom. As the alkyl group, is preferred a methyl group. As the alkynyl group, is particularly preferred an ethynyl group. As specific preferable examples of the group represented by the above formula, may be mentioned chlorophenylethynyl, fluorophenylethynyl, bromophenylethynyl, and ethynylphenylethynyl groups. The position in the group substituted by the halogen atom, alkyl group, or alkynyl group is particularly preferably a 4-position in the above formula though it should not be particularly limited. As specific preferable examples thereof, may be mentioned 4-chlorophenylethynyl, 4-fluorophenylethynyl, 4-bromophenylethynyl and 4-ethynylphenylethynyl groups.

In the following group:

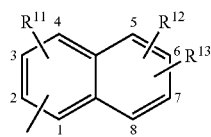

(c)

(wherein $R^{11}$, $R^{12}$ and $R^{13}$ have the same meanings as defined above, and numerals 1 to 8 indicate locants), $R^{11}$, $R^{12}$ and $R^{13}$ are each independently preferably a hydrogen atom, cyano group, halogen atom, alkyl group, alkenyl group, alkynyl group, or halogenoalkyl group. $R^{11}$ is preferably a hydrogen atom, alkyl group, halogen atom, or hydroxyl group, with a hydrogen atom being particularly preferred. It is preferable that one of $R^{12}$ and $R^{13}$ is a hydrogen atom, and the other is a hydrogen atom, cyano group, halogen atom, alkyl group, alkenyl group, alkynyl group, or halogenoalkyl group. Among others, it is particularly preferred that the other group be a hydrogen atom, halogen atom, alkyl group, or alkynyl group. In this case, the halogen atom is preferably a fluorine, chlorine, or bromine atom. As the alkyl group, is preferred a methyl group. As the alkynyl group, is preferred an ethynyl group. In the naphthyl group, a 2-naphthyl group is preferred to a 1-naphthyl group. In the case of the 2-naphthyl group, the position in the group substituted by a halogen atom, alkyl group, or alkynyl group is preferably a 6- or 7-position in the above formula though it should not be particularly limited, with a 6-position being most preferred. These naphthyl groups are more preferably substituted by a chlorine, fluorine, or bromine atom, an alkynyl group, or the like, with a group having a substituent such as a chlorine, fluorine or bromine atom, an alkynyl group, or the like being particularly preferred. As specific preferable examples thereof, may be mentioned 6-chloro-2-naphthyl, 6-fluoro-2-naphthyl, 6-bromo-2-naphthyl, 6-ethynyl-2-naphthyl, 7-chloro-2-naphthyl, 7-fluoro-2-naphthyl, 7-bromo-2-naphthyl, and 7-ethynyl-2-naphthyl groups.

In the following group:

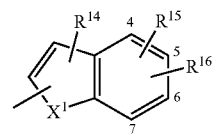

(d)

(wherein $X^1$, $R^{14}$, $R^{15}$ and $R^{16}$ have the same meanings as defined above, and numerals 4 to 7 indicate locants), $X^1$ is preferably NH, NOH, N, O, or S, with NH, O, or S being more preferred. $R^{14}$ is preferably a hydrogen atom, halogen atom, acyl group, N-alkylcarbamoyl group, N,N-dialkylcarbamoyl group, or alkyl group, and $R^{15}$ and $R^{16}$ are each independently preferably a hydrogen atom, cyano group, halogen atom, alkyl group, alkenyl group, alkynyl group, or halogenoalkyl group. It is preferable that one of $R^{15}$ and $R^{16}$ is a hydrogen or a halogen atom, preferably fluorine atom or chlorine atom, and the other is a hydrogen atom, cyano group, halogen atom, alkyl group, alkenyl group, alkynyl group, or halogenoalkyl group. Among others, it is particularly preferred that the other group be a hydrogen atom, halogen atom, alkyl group, or alkynyl group. In this case, the halogen atom is preferably a fluorine, chlorine or bromine atom. As the alkyl group, is preferred a methyl group. As the alkynyl group, is preferred an ethynyl group. The position in the group substituted by the halogen atom, alkyl group, or alkynyl group is preferably a 4-, 5-, or 6-position in the above formula though it should not be particularly limited. As specific preferable examples of the group represented by the above formula, may be mentioned 5-chloroindolyl, 5-fluoroindolyl, 5-bromoindolyl, 5-ethynylindolyl, 5-methylindolyl, 5-chloro-4-fluoroindolyl, 5-chloro-3-fluoroindolyl, 5-fluoro-3-chloroindolyl, 5-ethynyl-3-fluoroindolyl, 5-chloro-3-(N,N-dimethylcarbamoyl)indolyl, 5-fluoro-3-(N,N-dimethylcarbamoyl)indolyl, 5-chloro-3-formylimidolyl, 5-fluoro-3-formylindolyl, 6-chloroindolyl, 6-fluoroindolyl, 6-bromoindolyl, 6-ethynylindolyl, 6-methylindolyl, 5-chlorobenzothienyl, 5-fluorobenzothienyl, 5-bromobenzothienyl, 5-ethynylbenzothienyl, 5-methylbenzothienyl, 5-chloro-4-fluorobenzothienyl, 6-chlorobenzothienyl, 6-fluorobenzothienyl, 6-bromobenzothienyl, 6-ethynylbenzothienyl, 6-methylbenzothienyl, 5-chlorobenzofuryl, 5-fluorobenzofuryl, 5-bromobenzofuryl, 5-ethynylbenzofuryl, 5-methylbenzofuryl, 5-chloro-4-fluorobenzofuryl, 6-chlorobenzofuryl, 6-fluorobenzofuryl, 6-bromobenzofuryl, 6-ethynylbenzofuryl, and 6-methylbenzofuryl groups. The position of the above-described substituent group bonded to $T^1$ is not particularly limited, but is preferably a 2-position or 3-position in the formula (d). Specifically, more preferred are 5-chloroindol-2-yl, 5-fluoroindol-2-yl, 5-bromoindol-2-yl, 5-ethynylindol-2-yl, 5-methylindol-2-yl, 5-chloro-4-fluoroindol-2-yl, 5-chloro-3-fluoroindol-2-yl, 3-bromo-5-chloroindol-2-yl, 3-chloro-5-fluoroindol-2-yl, 3-bromo-5-fluoroindol-2-yl, 5-bromo-3-chloroindol-2-yl, 5-bromo-3-fluoroindol-2-yl, 5-chloro-3-formylindol-2-yl, 5-fluoro-3-formylindol-2-yl, 5-bromo-3-formylindol-2-yl, 5-ethynyl-3-formylindol-2-yl, 5-chloro-3-(N,N-dimethylcarbamoyl)indol-2-yl, 5-fluoro-3-(N,N-dimethylcarbamoyl)indol-2-yl, 5-bromo-3-(N,N-dimethylcarbamoyl)indol-2-yl, 5-ethynyl-3-(N,N-dimethylcarbamoyl)indol-2-yl, 6-chloroindol-2-yl, 6-fluoroindol-2-yl, 6-bromoindol-2-yl, 6-ethynylindol-2-yl, 6-methylindol-2-yl, 5-chloroindol-3-yl, 5-fluoroindol-3-yl, 5-bromoindol-3-yl, 5-ethynylindol-3-yl, 5-methylindol-3-yl, 5-chloro-4-fluoroindol-3-yl, 6-chloroindol-3-yl, 6-fluoroindol-3-yl, 6-bromoindol-3-yl, 6-ethynylindol-3-yl, 6-methylindol-3-yl, 5-chlorobenzothiophen-2-yl, 5-fluorobenzothiophen-2-yl, 5-bromobenzothiophen-2-yl, 5-ethynylbenzothiophen-2-yl, 5-methylbenzothiophen-2-yl, 5-chloro-4-fluorobenzothiophen-2-yl, 6-chlorobenzothiophen-2-yl, 6-fluorobenzothiophen-2-yl, 6-bromobenzothiophen-2-yl, 6-ethynylbenzothiophen-2-yl, 6-methylbenzothiophen-2-yl, 5-chlorobenzothiophen-3-yl, 5-fluorobenzothiophen-3-yl, 5-bromobenzothiophen-3-yl, 5-ethynylbenzothiophen-3-yl, 5-methylbenzothiophen-3-yl, 5-chloro-4-fluorobenzothiophen-3-yl, 6-chlorobenzothiophen-3-yl, 6-fluorobenzothiophen-3-yl, 6-bromobenzothiophen-3-yl, 6-ethynylbenzothiophen-3-yl, 6-methylbenzothiophen-3-yl, 5-chlorobenzofuran-2-yl, 5-fluorobenzofuran-2-yl, 5-bromobenzofuran-2-yl, 5-ethynylbenzofuran-2-yl, 5-methylbenzofuran-2-yl, 5-chloro-4-fluorobenzofuran-2-yl, 6-chlorobenzofuran-2-yl, 6-fluorobenzofuran-2-yl, 6-bromobenzofuran-2-yl, 6-ethynylbenzofuran-2-yl, 6-methylbenzofuran-2-yl, 5-chlorobenzofuran-3-yl, 5-fluorobenzofuran-3-yl, 5-bromobenzofuran-3-yl, 5-ethynylbenzofuran-3-yl, 5-methylbenzofuran-3-yl, 5-chloro-4-fluorobenzofuran-3-yl, 6-chlorobenzofuran-3-yl, 6-fluorobenzofuran-3-yl, 6-bromobenzofuran-3-yl, 6-ethynylbenzofuran-3-yl, and 6-methylbenzofuran-3-yl groups, with 5-chloroindol-2-yl, 5-fluoroindol-2-yl, 5-bromoindol-2-yl, 5-ethynylindol-2-yl, 5-methylindol-2-yl, 5-chloro-4-fluoroindol-2-yl, 6-chloroindol-2-yl, 6-fluoroindol-2-yl, 6-bromoindol-2-yl, 6-ethynylindol-2-yl, 6-methylindol-2-yl, 5-chloro-3-fluoroindol-2-yl, 3-bromo-5-chloroindol-2-yl, 3-chloro-5-fluoroindol-2-yl, 3-bromo-5-fluoroindol-2-yl, 5-bromo-3-chloroindol-2-yl, 5-bromo-3-fluoroindol-2-yl, 5-chloro-3-formylindol-2-yl, 5-fluoro-3-formylindol-2-yl, 5-bromo-3-formylindol-2-yl, 5-ethynyl-3-formylindol-2-yl, 5-chloro-3-(N,N-dimethylcarbamoyl)indol-2-yl, 5-fluoro-3-(N,N-dimethylcarbamoyl)indol-2-yl, 5-bromo-3-(N,N-dimethylcarbamoyl)indol-2-yl, 5-ethynyl-3-(N,N-dimethylcarbamoyl)indol-2-yl, 5-chlorobenzothiophen-2-yl, 5-fluorobenzothiophen-2-yl, 5-bromobenzothiophen-2-yl, 5-ethynylbenzothiophen-2-yl, 5-methylbenzothiophen-2-yl, 5-chloro-4-fluorobenzothiophen-2-yl, 6-chlorobenzothiophen-2-yl, 6-fluorobenzothiophen-2-yl, 6-bromobenzothiophen-2-yl, 6-ethynylbenzothiophen-2-yl, 6-methylbenzothiophen-2-yl, 5-chlorobenzofuran-2-yl, 5-fluorobenzofuran-2-yl, 5-bromobenzofuran-2-yl, 5-ethynylbenzofuran-2-yl, 5-methylbenzofuran-2-yl, 5-chloro-4-fluorobenzofuran-2-yl, 6-chlorobenzofuran-2-yl, 6-fluorobenzofuran-2-yl, 6-bromobenzofuran-2-yl, 6-ethynylbenzofuran-2-yl, and 6-methylbenzofuran-2-yl groups being particularly preferred.

In the following group:

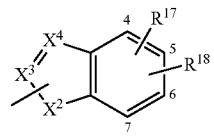

(e)

(wherein $X^2$, $X^3$, $X^4$, $R^{17}$ and $R^{18}$ have the same meanings as defined above, and numerals 4 to 7 indicate locants), $X^2$ is preferably NH, O, or S, any one of $X^3$ and $X^4$ is preferably CH or C, particularly preferably C. $R^{17}$ and $R^{18}$ are each independently preferably a hydrogen atom, cyano group, halogen atom, alkyl group, alkenyl group, alkynyl group or halogenoalkyl group. It is preferable that one of $R^{17}$ and $R^{18}$ is a hydrogen atom, and the other is a hydrogen atom, cyano group, halogen atom, alkyl group, alkenyl group, alkynyl group, or halogenoalkyl group. Among others, it is particularly preferred that the other group be a hydrogen atom, halogen atom, alkyl group, or alkynyl group. In this case, the halogen atom is preferably a fluorine, chlorine, or bromine atom. As the alkyl group, is preferred a methyl group. As the alkynyl group, is preferred an ethynyl group. The position substituted by the halogen atom, alkyl group, or alkynyl group is preferably a 5- or 6-position in the above formula though it should not be particularly limited. As specific preferable examples of the group represented by the above formula, may be mentioned 5-chloroindazolyl, 5-fluoroindazolyl, 5-bromoindazolyl, 5-ethynylindazolyl, 6-chloroindazolyl, 6-fluoroindazolyl, 6-bromoindazolyl, 6-ethynylindazolyl, 5-chlorobenzimidazolyl, 5-fluorobenzimidazolyl, 5-bromobenzimidazolyl, 5-ethynylbenzimidazolyl, 6-chlorobenzimidazolyl, 6-fluorobenzimidazolyl, 6-bromobenzimidazolyl, 6-ethynylbenzimidazolyl, 5-chlorobenzothiazolyl, 5-fluorobenzothiazolyl, 5-bromobenzothiazolyl, 5-ethynylbenzothiazolyl, 6-chlorobenzothiazolyl, 6-fluorobenzothiazolyl, 6-bromobenzothiazolyl, 6-ethynylbenzothiazolyl, 5-chlorobenzoxazolyl, 5-fluorobenzoxazolyl, 5-bromobenzoxazolyl, 5-ethynylbenzoxazolyl, 6-chlorobenzoxazolyl, 6-fluorobenzoxazolyl, 6-bromobenzoxazolyl, 6-ethynylbenzoxazolyl, 5-chlorobenzisothiazolyl, 5-fluorobenzisothiazolyl, 5-bromobenzisothiazolyl, 5-ethynylbenzisothiazolyl, 6-chlorobenzisothiazolyl, 6-fluorobenzisothiazolyl, 6-bromobenzisothiazolyl, 6-ethynylbenzisothiazolyl, 5-chlorobenzisoxazolyl, 5-fluorobenzisoxazolyl, 5-bromobenzisoxazolyl, 5-ethynylbenzisoxazolyl, 6-chlorobenzisoxazolyl, 6-fluorobenzisoxazolyl, 6-bromobenzisoxazolyl, and 6-ethynylbenzisoxazolyl groups. The position of the above-described substituent group bonded to $T^1$ is not particularly limited. More preferred are 5-chloroindazol-3-yl, 5-fluoroindazol-3-yl, 5-bromoindazol-3-yl, 5-ethynylindazol-3-yl, 6-chloroindazol-3-yl, 6-fluoroindazol-3-yl, 6-bromoindazol-3-yl, 6-ethynylindazol-3-yl, 5-chlorobenzimidazol-2-yl, 5-fluorobenzimidazol-2-yl, 5-bromobenzimidazol-2-yl, 5-ethynylbenzimidazol-2-yl, 6-chlorobenzimidazol-2-yl, 6-fluorobenzimidazol-2-yl, 6-bromobenzimidazol-2-yl, 6-ethynylbenzimidazol-2-yl, 5-chlorobenzothiazol-2-yl, 5-fluorobenzothiazol-2-yl, 5-bromobenzothiazol-2-yl, 5-ethynylbenzothiazol-2-yl, 6-chlorobenzothiazol-2-yl, 6-fluorobenzothiazol-2-yl, 6-bromobenzothiazol-2-yl, 6-ethynylbenzothiazol-2-yl, 5-chlorobenzoxazol-2-yl, 5-fluorobenzoxazol-2-yl, 5-bromobenzoxazol-2-yl, 5-ethynylbenzoxazol-2-yl, 6-chlorobenzoxazol-2-yl, 6-fluorobenzoxazol-2-yl, 6-bromobenzoxazol-2-yl, 6-ethynylbenzoxazol-2-yl, 5-chlorobenzisothiazol-3-yl, 5-fluorobenzisothiazol-3-yl, 5-bromobenzisothiazol-3-yl, 5-ethynylbenzisothiazol-3-yl, 6-chlorobenzisothiazol-3-yl, 6-fluorobenzisothiazol-3-yl, 6-bromobenzisothiazol-3-yl, 6-ethynylbenzisothiazol-3-yl, 5-chlorobenzisoxazol-3-yl, 5-fluorobenzisoxazol-3-yl, 5-bromobenzisoxazol-3-yl, 5-ethynylbenzisoxazol-3-yl, 6-chlorobenzisoxazol-3-yl, 6-fluorobenzisoxazol-3-yl, 6-bromobenzisoxazol-3-yl, and 6-ethynylbenzisoxazol-3-yl groups, with 5-chlorobenzimidazol-2-yl, 5-fluorobenzimidazol-2-yl, 5-bromobenzimidazol-2-yl, 5-ethynylbenzimidazol-2-yl, 6-chlorobenzimidazol-2-yl, 6-fluorobenzimidazol-2-yl, 6-bromobenzimidazol-2-yl, 6-ethynylbenzimidazol-2-yl, 5-chlorobenzothiazol-2-yl, 5-fluorobenzothiazol-2-yl, 5-bromobenzothiazol-2-yl, 5-ethynylbenzothiazol-2-yl, 6-chlorobenzothiazol-2-yl, 6-fluorobenzothiazol-2-yl, 6-bromobenzothiazol-2-yl, 6-ethynylbenzothiazol-2-yl, 5-chlorobenzoxazol-2-yl, 5-fluorobenzoxazol-2-yl, 5-bromobenzoxazol-2-yl, 5-ethynylbenzoxazol-2-yl, 6-chlorobenzoxazol-2-yl, 6-fluorobenzoxazol-2-yl, 6-bromobenzoxazol-2-yl, and 6-ethynylbenzoxazol-2-yl groups being particularly preferred. Among these, 5-chlorobenzimidazol-2-yl, 5-fluorobenzimidazol-2-yl, 5-bromobenzimidazol-2-yl and 5-ethynylbenzimidazol-2-yl groups are further preferred.

In the following group:

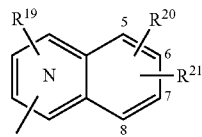

(f)

(wherein N indicates that 1 or 2 carbon atoms of the ring substituted by $R^{19}$ have been substituted by a nitrogen atom, $R^{19}$, $R^{20}$, and $R^{21}$ have the same meanings as defined above, and numerals 5 to 8 indicate locants), $R^{19}$, $R^{20}$, and $R^{21}$ are each independently preferably a hydrogen atom, cyano group, halogen atom, alkyl group, alkenyl group, alkynyl group, or halogenoalkyl group. $R^{19}$ is particularly preferably a hydrogen atom. It is preferable that one of $R^{20}$ and $R^{21}$ is a hydrogen atom, and the other is a hydrogen atom, cyano group, halogen atom, alkyl group, alkenyl group, alkynyl group, or halogenoalkyl group. Among others, it is particularly preferred that the other group be a hydrogen atom, halogen atom, alkyl group, or alkynyl group. In this case, the halogen atom is preferably a fluorine, chlorine, or bromine atom. As the alkyl group, is preferred a methyl group. As the alkynyl group, is preferred an ethynyl group. The position substituted by the halogen atom, alkyl group, or alkynyl group is preferably a 6- or 7-position in the above formula though it should not be particularly limited. As specific preferable examples thereof, may be mentioned quinolinyl, isoquinolinyl, and cinnolinyl groups. More preferred are 6-chloroquinolinyl, 6-fluoroquinolinyl, 6-bromoquinolinyl, 6-ethynylquinolinyl, 6-chloroisoquinolinyl, 6-fluoroisoquinolinyl, 6-bromoisoquinolinyl, 6-ethynylisoquinolinyl, 7-chlorocinnolinyl, 7-fluorocinnolinyl, 7-bromocinnolinyl, and 7-ethynylcinnolinyl groups, with 6-chloroquinolin-2-yl, 6-fluoroquinolin-2-yl, 6-bromoquinolin-2-yl, 6-ethynylquinolin-2-yl, 6-chloroquinolin-3-yl, 6-fluoroquinolin-3-yl, 6-bromoquinolin-3-yl, 6-ethynylquinolin-3-yl, 7-chloroquinolin-2-yl, 7-fluoroquinolin-2-yl, 7-bromoquinolin-2-yl, 7-ethynylquinolin-2-yl, 7-chloroquinolin-3-yl, 7-fluoroquinolin-3-yl, 7-bromoquinolin-3-yl, 7-ethynylquinolin-3-yl, 6-chloroisoquinolin-3-yl, 6-fluoroisoquinolin-3-yl, 6-bromoisoquinolin-3-yl, 6-ethynylisoquinolin-3-yl, 7-chloroisoquinolin-3-yl, 7-fluoroisoquinolin-3-yl, 7-bromoisoquinolin-3-yl, 7-ethynylisoquinolin-3-yl, 7-chlorocinnolin-3-yl, 7-fluorocinnolin-3-yl, 7-bromocinnolin-3-yl, and 7-ethynylcinnolin-3-yl groups being particularly preferred. Among these, 6-chloroquinolin-2-yl, 6-fluoroquinolin-2-yl, 6-bromoquinolin-2-yl, 6-ethynylquinolin-2-yl, 7-chloroquinolin-3-yl, 7-fluoroquinolin-3-yl, 7-bromoquinolin-3-yl, 7-ethynylquinolin-3-yl, 7-chloroisoquinolin-3-yl, 7-fluoroisoquinolin-3-yl, 7-bromoisoquinolin-3-yl, 7-ethynylisoquinolin-3-yl, 7-chlorocinnolin-3-yl, 7-fluorocinnolin-3-yl, 7-bromocinnolin-3-yl, and 7-ethynylcinnolin-3-yl groups are further preferred.

In the following group:

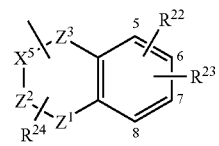

(g)

(wherein numerals 5 to 8 indicate locants, $X^5$ represents $CH_2$, CH, N or NH, $Z^1$ represents N, NH or O, $Z^2$ represents $CH_2$, CH, C or N, $Z^3$ represents $CH_2$, CH, S, $SO_2$ or C=O, $X^5$—$Z^2$ indicates that $X^5$ and $Z^2$ are bonded to each other by a single bond or double bond, and $R^{22}$, $R^{23}$ and $R^{24}$ have the same meanings as defined above), $R^{22}$ and $R^{23}$ are each independently preferably a hydrogen atom, cyano group, halogen atom, alkyl group, alkenyl group, alkynyl group or halogenoalkyl group. It is preferable that one of $R^{22}$ and $R^{23}$ is a hydrogen atom, and the other is a hydrogen atom, cyano group, halogen atom, alkyl group, alkenyl group, alkynyl group or halogenoalkyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is preferred an ethynyl group. The position substituted by the halogen atom, alkyl group or alkynyl group is preferably a 6- or 7-position in the above formula though it should not be particularly limited. $R^{24}$ is preferably a hydrogen atom or alkyl group, and a methyl group is preferred as the alkyl group. As $R^{24}$, is particularly preferred a hydrogen atom. As specific preferred groups represented by the above formula, may be mentioned 4-oxodihydroquinolinyl, tetrahydroquinolinyl, 4-oxodihydroquinazolin-2-yl, 4-oxotetrahydrocinnolinyl, 4-oxobenzopyranyl, 4-oxobenzothiadiazinyl, 1,1-dioxy-4-oxobenzothiadiazinyl and benzoxadiazinyl groups. As specific preferable examples thereof, may be mentioned 6-chloro-4-oxodihydroquinolinyl, 6-fluoro-4-oxodihydroquinolinyl, 6-bromo-4-oxodihydroquinolinyl, 6-ethynyl-4-oxodihydroquinolinyl, 7-chloro-4-oxodihydroquinolinyl, 7-fluoro-4-oxodihydroquinolinyl, 7-bromo-4-oxodihydroquinolinyl, 7-ethynyl-4-oxodihydroquinolinyl, 6-chloro-4-oxo-1,4-dihydroquinazolinyl, 6-fluoro-4-oxo-1,4-dihydroquinazolinyl, 6-bromo-4-oxo-1,4-dihydroquinazolinyl, 6-ethynyl-4-oxo-1,4-dihydroquinazolinyl, 7-chloro-4-oxo-1,4-dihydroquinazolinyl, 7-fluoro-4-oxo-1,4-dihydroquinazolinyl, 7-bromo-4-oxo-1,4-dihydroquinazolinyl, 7-ethynyl-4-oxo-1,4-dihydroquinazolinyl, 6-chloro-1,2,3,4-tetrahydroquinolinyl, 6-fluoro-1,2,3,4-tetrahydroquinolinyl, 6-bromo-1,2,3,4-tetrahydroquinolinyl, 6-ethynyl-1,2,3,4-tetrahydroquinolinyl, 7-chloro-1,2,3,4-tetrahydroquinolinyl, 7-fluoro-1,2,3,4-tetrahydroquinolinyl, 7-bromo-1,2,3,4-tetrahydroquinolinyl, 7-ethynyl-1,2,3,4-tetrahydroquinolinyl, 6-chloro-1,2,3,4-tetrahydro-4-oxocinnolinyl, 6-fluoro-1,2,3,4-tetrahydro-4-oxocinnolinyl, 6-bromo-1,2,3,4-tetrahydro-4-oxocinnolinyl, 6-ethynyl-1,2,3,4-tetrahydro-4-oxocinnolinyl, 7-chloro-1,2,3,4-tetrahydro-4-oxocinnolinyl, 7-fluoro-1,2,3,4-tetrahydro-4-oxocinnolinyl, 7-bromo-1,2,3,4-tetrahydro-4-oxocinnolinyl, 7-ethynyl-1,2,3,4-tetrahydro-4-oxocinnolinyl, 6-chloro-4H-4-oxobenzopyranyl, 6-fluoro-4H-4-oxobenzopyranyl, 6-bromo-4H-4-oxobenzopyranyl, 6-ethynyl-4H-4-oxobenzopyranyl, 7-chloro-4H-4-oxobenzopyranyl, 7-fluoro-4H-4-oxobenzopyranyl, 7-bromo-4H-4-oxobenzopyranyl, 7-ethynyl-4H-4-oxobenzopyranyl, 6-chloro-1,1-dioxy-2H-1,2,4-benzothiadiazinyl, 6-fluoro-1,1-dioxy-2H-1,2,4-benzothiadiazinyl, 6-bromo-1,1-dioxy-2H-1,2,4-benzothiadiazinyl, 6-ethynyl-1,1-dioxy-2H-1,2,4-benzothiadiazinyl, 7-chloro-1,1-dioxy-2H-1,2,4-benzothiadiazinyl, 7-fluoro-1,1-dioxy-2H-1,2,4-benzothiadiazinyl, 7-bromo-1,1-dioxy-2H-1,2,4-benzothiadiazinyl, 7-ethynyl-1,1-dioxy-2H-1,2,4-benzothiadiazinyl, 6-chloro-2H-1,2,4-benzoxadiazinyl, 6-fluoro-2H-1,2,4-benzoxadiazinyl, 6-bromo-2H-1,2,4-benzoxadiazinyl, 6-ethynyl-2H-1,2,4-benzoxadiazinyl, 7-chloro-2H-1,2,4-benzoxadiazinyl, 7-fluoro-2H-1,2,4-benzoxadiazinyl, 7-bromo-2H-1,2,4-benzoxadiazinyl and 7-ethynyl-2H-1,2,4-benzoxadiazinyl groups; with 6-chloro-4-oxo-1,4-dihydroquinolin-2-yl, 6-fluoro-4-oxo-1,4-dihydroquinolin-2-yl, 6-bromo-4-oxo-1,4-dihydroquinolin-2-yl, 6-ethynyl-4-oxo-1,4-dihydroquinolin-2-yl, 7-chloro-4-oxo-1,4-dihydroquinolin-2-yl, 7-fluoro-4-oxo-1,4-dihydroquinolin-2-yl, 7-bromo-4-oxo-1,4-dihydroquinolin-2-yl, 7-ethynyl-4-oxo-1,4-dihydroquinolin-2-yl, 6-chloro-4-oxo-1,4-dihydroquinazolin-2-yl, 6-fluoro-4-oxo-1,4-dihydroquinazolin-2-yl, 6-bromo-4-oxo-1,4-dihydroquinazolin-2-yl, 6-ethynyl-4-oxo-1,4-dihydroquinazolin-2-yl, 7-chloro-4-oxo-1,4-dihydroquinazolin-2-yl, 7-fluoro-4-oxo-1,4-dihydroquinazolin-2-yl, 7-bromo-4-oxo-1,4-dihydroquinazolin-2-yl, 7-ethynyl-4-oxo-1,4-dihydroquinazolin-2-yl, 6-chloro-1,2,3,4-tetrahydroquinolin-2-yl, 6-fluoro-1,2,3,4-tetrahydroquinolin-2-yl, 6-bromo-1,2,3,4-tetrahydroquinolin-2-yl, 6-ethynyl-1,2,3,4-tetrahydroquinolin-2-yl, 6-chloro-1,2,3,4-tetrahydro-4-oxocinnolin-2-yl, 6-fluoro-1,2,3,4-tetrahydro-4-oxocinnolin-2-yl, 6-bromo-1,2,3,4-tetrahydro-4-oxocinnolin-2-yl, 6-ethynyl-1,2,3,4-tetrahydro-4-oxocinnolin-2-yl, 7-chloro-1,2,3,4-tetrahydro-4-oxocinnolin-2-yl, 7-fluoro-1,2,3,4-tetrahydro-4-oxocinnolin-2-yl, 7-bromo-1,2,3,4-tetrahydro-4-oxocinnolin-2-yl, 7-ethynyl-1,2,3,4-tetrahydro-4-oxocinnolin-2-yl, 6-chloro-4H-4-oxobenzopyran-2-yl, 6-fluoro-4H-4-oxobenzopyran-2-yl, 6-bromo-4H-4-oxobenzopyran-2-yl, 6-ethynyl-4H-4-oxobenzopyran-2-yl, 7-chloro-4H-4-oxobenzopyran-2-yl, 7-fluoro-4H-4-oxobenzopyran-2-yl, 7-bromo-4H-4-oxobenzopyran-2-yl, 7-ethynyl-4H-4-oxobenzopyran-2-yl, 6-chloro-1,1-dioxy-2H-1,2,4-benzothiadiazin-3-yl, 6-fluoro-1,1-dioxy-2H-1,2,4-benzothiadiazin-3-yl, 6-bromo-1,1-dioxy-2H-1,2,4-benzothiadiazin-3-yl, 6-ethynyl-1,1-dioxy-2H-1,2,4-benzothiadiazin-3-yl, 7-chloro-1,1-dioxy-2H-1,2,4-benzothiadiazin-3-yl, 7-fluoro-1,1-dioxy-2H-1,2,4-benzothiadiazin-3-yl, 7-bromo-1,1-dioxy-2H-1,2,4-benzothiadiazin-3-yl, 7-ethynyl-1,1-dioxy-2H-1,2,4-benzothiadiazin-3-yl, 6-chloro-2H-1,2,4-benzoxadiazin-3-yl, 6-fluoro-2H-1,2,4-benzoxadiazin-3-yl, 6-bromo-2H-1,2,4-benzoxadiazin-3-yl, 6-ethynyl-2H-1,2,4-benzoxadiazin-3-yl, 7-chloro-2H-1,2,4-benzoxadiazin-3-yl, 7-fluoro-2H-1,2,4-benzoxadiazin-3-yl, 7-bromo-2H-1,2,4-benzoxadiazin-3-yl and 7-ethynyl-2H-1,2,4-benzoxadiazin-3-yl groups being particularly preferred. Among these, 6-chloro-4-oxo-1,4-dihydroquinolin-2-yl, 6-fluoro-4-oxo-1,4-dihydroquinolin-2-yl, 6-bromo-4-oxo-1,4-dihydroquinolin-2-yl, 6-ethynyl-4-oxo-1,4-dihydroquinolin-2-yl, 6-chloro-4-oxo-1,4-dihydroquinazolin-2-yl, 6-fluoro-4-oxo-1,4-dihydroquinazolin-2-yl, 6-bromo-4-oxo-1,4-dihydroquinazolin-2-yl and 6-ethynyl-4-oxo-1,4-dihydroquinazolin-2-yl are more particularly preferred.

In the following group:

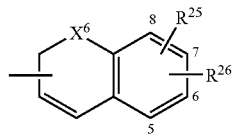

(h)

(wherein $X^6$ represents O or S, $R^{25}$ and $R^{26}$ have the same meanings as defined above, and numerals 5 to 8 indicate locants), $X^6$ is preferably O, and $R^{25}$ and $R^{26}$ are each independently preferably a hydrogen atom, cyano group, halogen atom, alkyl group, alkenyl group, alkynyl group or halogenoalkyl group. It is preferable that one of $R^{25}$ and $R^{26}$ is a hydrogen atom, and the other is a hydrogen atom, cyano group, halogen atom, alkyl group, alkenyl group, alkynyl group, or halogenoalkyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is preferred an ethynyl group. The position substituted by the halogen atom, alkyl group or alkynyl group is preferably a 6- or 7-position in the above formula though it should not be particularly limited. As specific examples of preferred ones, may be mentioned 6-chloro-2H-chromen-3-yl, 6-fluoro-2H-chromen-3-yl, 6-bromo-2H-chromen-3-yl, 6-ethynyl-2H-chromen-3-yl, 7-chloro-2H-chromen-3-yl, 7-fluoro-2H-chromen-3-yl, 7-bromo-2H-chromen-3-yl and 7-ethynyl-2H-chromen-3-yl groups, with 7-chloro-2H-chromen-3-yl, 7-fluoro-2H-chromen-3-yl, 7-bromo-2H-chromen-3-yl and 7-ethynyl-2H-chromen-3-yl groups being particularly preferred.

In the following group:

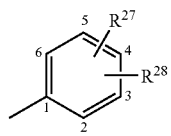

(i)

(wherein $R^{27}$ and $R^{28}$ have the same meanings as defined above, and numerals 1 to 6 indicate locants), it is preferable that one of $R^{27}$ and $R^{28}$ is a hydrogen atom or halogen atom, and the other is a hydrogen atom, cyano group, nitro group, amino group, halogen atom, alkyl group, alkenyl group, alkynyl group, halogenoalkyl group or N,N-dialkylcarbamoyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is particularly preferred an ethynyl group. As specific examples of preferred groups represented by the above formula, may be mentioned phenyl, chlorophenyl, fluorophenyl, bromophenyl, ethynylphenyl and chlorofluorophenyl groups. The position substituted by the halogen atom, alkyl group or alkynyl group in these groups is particularly preferably a 3- or 4-position in the above formula in the case of one substituent, or a combination of a 4-position and a 2- or 3-position in the above formula in the case of two substituents, though it should not be particularly limited. As specific examples of preferred ones, may be mentioned phenyl, 4-chlorophenyl, 4-fluorophenyl, 4-bromophenyl, 4-ethynylphenyl, 3-chlorophenyl, 3-fluorophenyl, 3-bromophenyl, 3-ethynylphenyl, 3-chloro-4-fluorophenyl, 4-chloro-3-fluorophenyl, 4-chloro-2-fluorophenyl, 2-chloro-4-fluorophenyl, 4-bromo-2-fluorophenyl, 2-bromo-4-fluorophenyl, 2,4-dichlorophenyl, 2,4-difluorophenyl, 2,4-dibromophenyl, 4-chloro-3-methylphenyl, 4-fluoro-3-methylphenyl, 4-bromo-3-methylphenyl, 4-chloro-2-methylphenyl, 4-fluoro-2-methylphenyl, 4-bromo-2-methylphenyl, 3,4-dichlorophenyl, 3,4-difluorophenyl and 3,4-dibromophenyl groups.

In the following group:

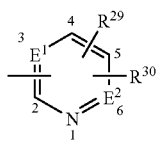

(j)

(wherein $E^1$, $E^2$, $R^{29}$ and $R^{30}$ have the same meanings as defined above, and numerals 1 to 6 indicate locants), it is preferable that one of $R^{29}$ and $R^{30}$ is a hydrogen atom or halogen atom, and the other is a hydrogen atom, cyano group, halogen atom, alkyl group, alkenyl group, alkynyl group or halogenoalkyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is particularly preferred an ethynyl group. As specific examples of the group represented by the above formula, may be mentioned pyridyl, pyrimidyl and pyridazinyl groups. The position substituted by the halogen atom, alkyl group or alkynyl group in these groups is particularly preferably a 4- or 5-position in the above formula in the case where its bonding to the group $T^1$ is at a 2-position in the above formula, though it should not be particularly limited. As specific examples of preferred ones, may be mentioned 2-pyridyl, 3-pyridyl, 4-pyridyl, 4-chloro-2-pyridyl, 4-fluoro-2-pyridyl, 4-bromo-2-pyridyl, 4-ethynyl-2-pyridyl, 4-chloro-3-pyridyl, 4-fluoro-3-pyridyl, 4-bromo-3-pyridyl, 4-ethynyl-3-pyridyl, 5-chloro-2-pyridyl, 5-fluoro-2-pyridyl, 5-bromo-2-pyridyl, 5-ethynyl-2-pyridyl, 4-chloro-5-fluoro-2-pyridyl, 5-chloro-4-fluoro-2-pyridyl, 5-chloro-3-pyridyl, 5-fluoro-3-pyridyl, 5-bromo-3-pyridyl, 5-ethynyl-3-pyridyl, 5-chloro-2-pyrimidyl, 5-fluoro-2-pyrimidyl, 5-bromo-2-pyrimidyl, 5-ethynyl-2-pyrimidyl, 4-chloro-3-pyridazinyl, 4-fluoro-3-pyridazinyl, 4-bromo-3-pyridazinyl, 4-ethynyl-3-pyridazinyl, 6-chloro-3-pyridazinyl, 6-fluoro-3-pyridazinyl, 6-bromo-3-pyridazinyl and 6-ethynyl-3-pyridazinyl groups. Particularly preferred are 2-pyridyl, 3-pyridyl, 4-pyridyl, 4-chloro-2-pyridyl, 4-fluoro-2-pyridyl, 4-bromo-2-pyridyl, 4-ethynyl-2-pyridyl, 4-chloro-3-pyridyl, 4-fluoro-3-pyridyl, 4-bromo-3-pyridyl, 4-ethynyl-3-pyridyl, 5-chloro-2-pyridyl, 5-fluoro-2-pyridyl, 5-bromo-2-pyridyl, 5-ethynyl-2-pyridyl, 4-chloro-5-fluoro-2-pyridyl, 5-chloro-4-fluoro-2-pyridyl, 5-chloro-3-pyridyl, 5-fluoro-3-pyridyl, 5-bromo-3-pyridyl, 5-ethynyl-3-pyridyl, 6-chloro-3-pyridazinyl, 6-fluoro-3-pyridazinyl, 6-bromo-3-pyridazinyl, 6-ethynyl-3-pyridazinyl, 4-chloro-3-pyridazinyl, 4-fluoro-3-pyridazinyl, 4-bromo-3-pyridazinyl and 4-ethynyl-3-pyridazinyl groups. Among these, 2-pyridyl, 3-pyridyl, 4-pyridyl, 5-chloro-2-pyridyl, 5-fluoro-2-pyridyl, 5-bromo-2-pyridyl, 5-ethynyl-2-pyridyl, 5-chloro-4-fluoro-2-pyridyl, 4-chloro-5-fluoro-2-pyridyl, 4-chloro-3-pyridazinyl, 4-fluoro-3-pyridazinyl, 4-bromo-3-pyridazinyl and 4-ethynyl-3-pyridazinyl groups are further preferred.

In the following group:

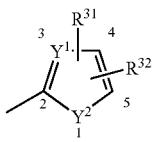

(k)

(wherein $Y^1$, $Y^2$, $R^{31}$ and $R^{32}$ have the same meanings as defined above, and numerals 1 to 5 indicate locants), it is preferable that one of $R^{31}$ and $R^{32}$ is a hydrogen atom or halogen atom, and the other is a hydrogen atom, cyano group, halogen atom, alkyl group, alkenyl group, alkynyl group or halogenoalkyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is particularly preferred an ethynyl group. As specific examples of the group represented by the above formula, may be mentioned thienyl, pyrrolyl, furyl, oxazolyl and thiazolyl groups. The position substituted by the halogen atom, alkyl group or alkynyl group in these groups is particularly preferably a 4- or 5-position in the above formula though it should not be particularly limited. As specific examples of preferred ones, may be mentioned 4-chloro-2-thienyl, 4-fluoro-2-thienyl, 4-bromo-2-thienyl, 4-ethynyl-2-thienyl, 4-chloro-2-pyrrolyl, 4-fluoro-2-pyrrolyl, 4-bromo-2-pyrrolyl, 4-ethynyl-2-pyrrolyl, 4-chloro-2-furyl, 4-fluoro-2-furyl, 4-bromo-2-furyl, 4-ethynyl-2-furyl, 5-chloro-2-thienyl, 5-fluoro-2-thienyl, 5-bromo-2-thienyl, 5-ethynyl-2-thienyl, 5-chloro-2-thiazolyl, 5-fluoro-2-thiazolyl, 5-bromo-2-thiazolyl, 5-ethynyl-2-thiazolyl, 5-chloro-2-oxazolyl, 5-fluoro-2-oxazolyl, 5-bromo-2-oxazolyl and 5-ethynyl-2-oxazolyl groups. Particularly preferred are 5-chloro-2-thiazolyl, 5-fluoro-2-thiazolyl, 5-bromo-2-thiazolyl and 5-ethynyl-2-thiazolyl groups.

In the following group:

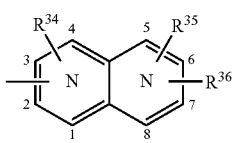

(l)

(wherein numerals 1 to 8 indicate locants, each N indicates that any one of four carbon atoms at positions 1 to 4 and any one of four carbon atoms at positions 5 to 8 have been substituted by a nitrogen atom, and $R^{34}$ to $R^{36}$ have the same meanings as defined above), the position of each nitrogen atom may be in any positional relation, and $R^{34}$ is preferably a hydrogen atom or halogen atom. It is preferable that one of $R^{35}$ and $R^{36}$ is a hydrogen atom or halogen atom, and the other is a hydrogen atom, cyano group, halogen atom, alkyl group, alkenyl group, alkynyl group, or halogenoalkyl group. Among others, it is particularly preferred that the other group be a hydrogen atom, halogen atom, alkyl group or alkynyl group. In this case, the halogen atom is preferably a fluorine, chlorine or bromine atom. As the alkyl group, is preferred a methyl group. As the alkynyl group, is particularly preferred an ethynyl group. The position substituted by the halogen atom, alkyl group or alkynyl group should not be particularly limited. As specific examples of preferred groups represented by the above formula, may be mentioned 6-chloro-1,5-naphthyridin-2-yl, 6-fluoro-1,5-naphthyridin-2-yl, 6-bromo-1,5-naphthyridin-2-yl, 6-ethynyl-1,5-naphthyridin-2-yl, 7-chloro-1,5-naphthyridin-2-yl, 7-fluoro-1,5-naphthyridin-2-yl, 7-bromo-1,5-naphthyridin-2-yl, 7-ethynyl-1,5-naphthyridin-2-yl, 6-chloro-1,5-naphthyridin-3-yl, 6-fluoro-1,5-naphthyridin-3-yl, 6-bromo-1,5-naphthyridin-3-yl, 6-ethynyl-1,5-naphthyridin-3-yl, 7-chloro-1,5-naphthyridin-3-yl, 7-fluoro-1,5-naphthyridin-3-yl, 7-bromo-1,5-naphthyridin-3-yl, 7-ethynyl-1,5-naphthyridin-3-yl, 6-chloro-1,7-naphthyridin-2-yl, 6-fluoro-1,7-naphthyridin-2-yl, 6-bromo-1,7-naphthyridin-2-yl, 6-ethynyl-1,7-naphthyridin-2-yl, 6-chloro-1,7-naphthyridin-3-yl, 6-fluoro-1,7-naphthyridin-3-yl, 6-bromo-1,7-naphthyridin-3-yl, 6-ethynyl-1,7-naphthyridin-3-yl, 6-chloro-1,8-naphthyridin-2-yl, 6-fluoro-1,8-naphthyridin-2-yl, 6-bromo-1,8-naphthyridin-2-yl, 6-ethynyl-1,8-naphthyridin-2-yl, 7-chloro-1,8-naphthyridin-2-yl, 7-fluoro-1,8-naphthyridin-2-yl, 7-bromo-1,8-naphthyridin-2-yl, 7-ethynyl-1,8-naphthyridin-2-yl, 6-chloro-1,8-naphthyridin-3-yl, 6-fluoro-1,8-naphthyridin-3-yl, 6-bromo-1,8-naphthyridin-3-yl, 6-ethynyl-1,8-naphthyridin-3-yl, 7-chloro-1,8-naphthyridin-3-yl, 7-fluoro-1,8-naphthyridin-3-yl, 7-bromo-1,8-naphthyridin-3-yl, 7-ethynyl-1,8-naphthyridin-3-yl, 6-chloro-2,5-naphthyridin-3-yl, 6-fluoro-2,5-naphthyridin-3-yl, 6-bromo-2,5-naphthyridin-3-yl, 6-ethynyl-2,5-naphthyridin-3-yl, 7-chloro-2,5-naphthyridin-3-yl, 7-fluoro-2,5-naphthyridin-3-yl, 7-bromo-2,5-naphthyridin-3-yl, 7-ethynyl-2,5-naphthyridin-3-yl, 7-chloro-2,6-naphthyridin-3-yl, 7-fluoro-2,6-naphthyridin-3-yl, 7-bromo-2,6-naphthyridin-3-yl, 7-ethynyl-2,6-naphthyridin-3-yl, 6-chloro-2,8-naphthyridin-3-yl, 6-fluoro-2,8-naphthyridin-3-yl, 6-bromo-2,8-naphthyridin-3-yl, 6-ethynyl-2,8-naphthyridin-3-yl, 7-chloro-2,8-naphthyridin-3-yl, 7-fluoro-2,8-naphthyridin-3-yl, 7-bromo-2,8-naphthyridin-3-yl and 7-ethynyl-2,8-naphthyridin-3-yl groups. Particularly preferable examples thereof include 7-chloro-2,5-naphthyridin-3-yl, 7-fluoro-2,5-naphthyridin-3-yl, 7-bromo-2,5-naphthyridin-3-yl and 7-ethynyl-2,5-naphthyridin-3-yl groups.

In addition to the above-mentioned 12 groups (a) to (l), a thienopyrrolyl group which may be substituted is preferred. This group may have 1 to 3 substituents, and examples of the substituents include a hydroxyl group, a nitro group, an amino group, a cyano group, halogen atoms, alkyl groups, alkenyl groups, alkynyl groups, halogenoalkyl groups, hydroxyalkyl groups, alkoxy groups, alkoxyalkyl groups, a carboxyl group, carboxyalkyl groups, acyl groups, a carbamoyl group, N-alkylcarbamoyl groups, N,N-dialkylcarbamoyl groups, alkoxycarbonyl groups, an amidino group and alkoxycarbonylalkyl groups. Among these, a cyano group, halogen atoms, alkyl groups, alkenyl groups, alkynyl groups and halogenoalkyl groups are preferred. As specific preferable examples thereof, may be mentioned 2-chlorothieno[2, 3-b]pyrrol-5-yl, 2-fluorothieno[2,3-b]pyrrol-5-yl, 2-bromothieno[2,3-b]pyrrol-5-yl, and 2-ethynylthieno[2,3-b]pyrrol-5-yl groups.

As examples of the saturated or unsaturated, 5- or 6-membered cyclic hydrocarbon group denoted by $Q^1$, may be mentioned cyclopentyl, cyclopentenyl, cyclohexyl, cyclohexenyl and phenyl groups. Cyclopentyl, cyclohexyl and phenyl groups are preferred, with a phenyl group being more preferred.

The saturated or unsaturated, 5- to 7-membered heterocyclic group denoted by $Q^1$ means a monovalent heterocyclic group having at least one hetero atom selected from among oxygen, sulfur and nitrogen atoms, and examples thereof may include furyl, pyrrolyl, thienyl, pyrazolyl, imidazolyl, pyrazolinyl, oxazolyl, oxazolinyl, thiazolyl, thiazolinyl, thiadiazolyl, furazanyl, pyranyl, pyridyl, pyrimidyl, pyridazinyl, pyrrolidinyl, piperazinyl, piperidinyl, oxazinyl, oxadiazinyl, morpholinyl, thiazinyl, thiadiazinyl, thiomorpholinyl, tetrazolyl, triazolyl, triazinyl, azepinyl, diazepinyl and triazepinyl groups. Of these, thienyl, pyrazolyl, imidazolyl, oxazolyl, thiazolyl, thiadiazolyl, furazanyl, pyridyl, pyrimidyl, pyridazinyl, pyrrolidinyl, piperazinyl, piperidinyl, morpholinyl, thiadiazinyl and triazolyl groups are preferred, with thienyl, thiazolyl, pyrazolyl, imidazolyl, pyridyl, pyrimidyl, pyridazinyl, pyrrolidinyl, piperazinyl and piperidinyl groups being more preferred. Of these heterocyclic groups, the nitrogen-containing heterocyclic groups may be in the form of an N-oxide.

The saturated or unsaturated, bicyclic or tricyclic condensed hydrocarbon group denoted by $Q^1$ means the same saturated or unsaturated, bicyclic or tricyclic condensed hydrocarbon group as described in the description of $Q^3$. As specific examples thereof, may be mentioned indenyl, indanyl, naphthyl, tetrahydronaphthyl, anthryl and phenanthryl groups, with indenyl, indanyl, naphthyl and tetrahydronaphthyl groups being preferred.

The saturated or unsaturated, bicyclic or tricyclic condensed heterocyclic group denoted by $Q^1$ means the same saturated or unsaturated, bicyclic or tricyclic condensed heterocyclic group as described in the description of $Q^3$. As specific examples thereof, may be mentioned benzofuryl, isobenzofuryl, benzothienyl, indolyl, indolinyl, isoindolyl, isoindolinyl, indazolyl, quinolyl, dihydroquinolyl, 4-oxodihydroquinolyl (dihydroquinolin-4-one), tetrahydroquinolyl, isoquinolyl, tetrahydroisoquinolyl, chromenyl, chromanyl, isochromanyl, 4H-4-oxobenzopyranyl, 3,4-dihydro-4H-4-oxobenzopyranyl, 4H-quinolizinyl, quinazolinyl, dihydroquinazolinyl, tetrahydroquinazolinyl, quinoxalinyl, tetrahydroquinoxalinyl, cinnolinyl, tetrahydrocinnolinyl, indolizinyl, tetrahydroindolizinyl, benzothiazolyl, tetrahydrobenzothiazolyl, benzoxazolyl, benzisothiazolyl, benzisoxazolyl, benzimidazolyl, naphthyridinyl, tetrahydronaphthyridinyl, thienopyridyl, tetrahydrothienopyridyl, thiazolopyridyl, tetrahydrothiazolopyridyl, thiazolopyridazinyl, tetrahydrothiazolopyridazinyl, pyrrolopyridyl, dihydropyrrolopyridyl, tetrahydropyrrolopyridyl, pyrrolopyrimidinyl, dihydropyrrolopyrimidinyl, pyridoquinazolinyl, dihydropyridoquinazolinyl, pyridopyrimidinyl, tetrahydropyridopyrimidinyl, pyranothiazolyl, dihydropyranothiazolyl, furopyridyl, tetrahydrofuropyridyl, oxazolopyridyl, tetrahydroxazolopyridyl, oxazolopyridazinyl, tetrahydroxazolopyridazinyl, pyrrolothiazolyl, dihydropyrrolothiazolyl, pyrrolooxazolyl, dihydropyrrolooxazolyl, thienopyrrolyl, thiazolopyrimidinyl, dihydrothiazolopyrimidinyl, 4-oxo-tetrahydrocinnolinyl, 1,2,4-benzothiadiazinyl, 1,1-dioxy-2H-1,2,4-benzothiadiazinyl, 1,2,4-benzoxadiazinyl, cyclopentapyranyl, thienofuranyl, furopyranyl, pyridoxazinyl, pyrazoloxazolyl, imidazothiazolyl, imidazopyridyl, tetrahydroimidazopyridyl, pyrazinopyridazinyl, benzisoquinolyl, furocinnolyl, pyrazolothiazolopyridazinyl, tetrahydropyrazolothiazolopyridazinyl, hexahydrothiazolopyridazinopyridazinyl, imidazotriazinyl, oxazolopyridyl, benzoxepinyl, benzazepinyl, tetrahydrobenzazepinyl, benzodiazepinyl, benzotriazepinyl, thienoazepinyl, tetrahydrothienoazepinyl, thienodiazepinyl, thienotriazepinyl, thiazoloazepinyl, tetrahydrothiazoloazepinyl, 4,5,6,7-tetrahydro-5,6-tetramethylenethiazolopyridazinyl and 5,6-trimethylene-4,5,6,7-tetrahydrothiazolopyridazinyl groups. Among them, preferred are benzothiazolyl, tetrahydrobenzothiazolyl, thienopyridyl, tetrahydrothienopyridyl, thienopyrrolyl, thiazolopyridyl, tetrahydrothiazolopyridyl, thiazolopyridazinyl, tetrahydrothiazolopyridazinyl, pyrrolopyrimidinyl, dihydropyrrolopyrimidinyl, pyranothiazolyl, dihydropyranothiazolyl, furopyridyl, tetrahydrofuropyridyl, oxazolopyridyl, tetrahydroxazolopyridyl, pyrrolopyridyl, dihydropyrrolopyridyl, tetrahydropyrrolopyridyl, oxazolopyridazinyl, tetrahydroxazolopyridazinyl, pyrrolothiazolyl, dihydropyrrolothiazolyl, pyrrolooxazolyl, dihydropyrrolooxazolyl, thiazolopyrimidinyl, dihydrothiazolopyrimidinyl, benzazepinyl, tetrahydrobenzazepinyl, thiazoloazepinyl, tetrahydrothiazoloazepinyl, thienoazepinyl, tetrahydrothienoazepinyl, 4,5,6,7-tetrahydro-5,6-tetramethylenethiazolopyridazinyl and 5,6-trimethylene-4,5,6,7-tetrahydrothiazolopyridazinyl groups, with tetrahydrobenzothiazolyl, tetrahydrothienopyridyl, tetrahydrothiazolopyridyl, tetrahydrothiazolopyridazinyl, dihydropyrrolopyrimidinyl, dihydropyranothiazolyl, tetrahydroxazolopyridyl, dihydropyrrolothiazolyl, 4,5,6,7-tetrahydro-5,6-tetramethylenethiazolopyridazinyl and 5,6-trimethylene-4,5,6,7-tetrahydrothiazolopyridazinyl groups being particularly preferred.

No particular limitation is imposed on the condensing form of the condensed heterocyclic groups. For example, thienopyridine may be any of thieno[2,3-b]pyridine, thieno[2,3-c]pyridine, thieno[3,2-b]pyridine, thieno[3,2-c]pyridine, thieno[3,4-b]pyridine and thieno[3,4-c]pyridine, with thieno[2,3-c]pyridine and thieno[3,2-c]-pyridine being preferred. Thienopyrrolyl may be any of thieno[2,3-b]pyrrolyl and thieno[3,2-b]-pyrrolyl. Thiazolopyridine may be any of thiazolo[4,5-b]pyridine, thiazolo[4,5-c]pyridine, thiazolo[5,4-b]pyridine, thiazolo[5,4-c]pyridine, thiazolo[3,4-a]pyridine and thiazolo[3,2-a]pyridine, with thiazolo[4,5-c]pyridine and thiazolo[5,4-c]pyridine being preferred. Thiazolopyridazine may be any of thiazolo[4,5-c]pyridazine, thiazolo[4,5-d]pyridazine, thiazolo[5,4-c]pyridazine and thiazolo[3,2-b]pyridazine, with thiazolo[4,5-d]pyridazine being preferred. Pyrrolopyridine may be any of pyrrolo[2,3-b]pyridine, pyrrolo[2,3-c]pyridine, pyrrolo[3,2-b]pyridine, pyrrolo[3,2-c]pyridine, pyrrolo[3,4-b]pyridine and pyrrolo[3,4-c]pyridine, with pyrrolo[2,3-c]pyridine and pyrrolo[3,2-c]pyridine being preferred. Pyrrolopyrimidine may be any of pyrrolo[3,4-d]pyrimidine, pyrrolo[3,2-d]pyrimidine and pyrrolo[2,3-d]pyrimidine, with pyrrolo[3,4-d]pyrimidine being preferred. Pyridopyrimidine may be any of pyrido[2,3-d]pyrimidine, pyrido[3,2-d]pyrimidine, pyrido[3,4-d]pyrimidine, pyrido[4,3-d]pyrimidine, pyrido[1,2-c]pyrimidine and pyrido[1,2-a]pyrimidine, with pyrido[3,4-d]pyrimidine and pyrido[4,3-d]pyrimidine being preferred. Pyranothiazole may be any of pyrano[2,3-d]thiazole, pyrano[4,3-d]thiazole, pyrano[3,4-d]thiazole and pyrano[3,2-d]thiazole, with pyrano[4,3-d]thiazole and pyrano[3,4-d]thiazole being preferred. Furopyridine may be any of furo[2,3-b]pyridine, furo[2,3-c]pyridine, furo[3,2-b]pyridine, furo[3,2-c]pyridine, furo[3,4-b]pyridine and furo[3,4-c]pyridine, with furo[2,3-c]pyridine and furo[3,2-c]pyridine being preferred. Oxazolopyridine may be any of oxazolo[4,5-b]pyridine, oxazolo[4,5-c]pyridine, oxazolo[5,4-b]pyridine, oxazolo[5,4-c]pyridine, oxazolo[3,4-a]pyridine and oxazolo[3,2-a]pyridine, with oxazolo[4,5-c]pyridine and oxazolo[5,4-c]pyridine being preferred. Oxazolopyridazine may be any of oxazolo[4,5-c]pyridazine, oxazolo[4,5-d]pyridazine, oxazolo[5,4-c]pyridazine and oxazolo[3,4-b]pyridazine, with oxazolo[4,5-d]pyridazine being preferred. Pyrrolothiazole may be any of pyrrolo[2,1-b]thiazole, pyrrolo[1,2-c]thiazole, pyrrolo[2,3-d]thiazole, pyrrolo[3,2-d]thiazole and pyrrolo[3,4-d]thiazole, with pyrrolo[3,4-d]thiazole being preferred. Pyrrolooxazole may be any of pyrrolo[2,1-b]oxazole, pyrrolo[1,2-c]oxazole, pyrrolo[2,3-d]oxazole, pyrrolo[3,2-d]oxazole, and pyrrolo[3,4-d]oxazole, with pyrrolo[3,4-d]oxazole being preferred. Benzazepine may be any of 1H-1-benzazepine, 1H-2-benzazepine and 1H-3-benzazepine, with 1H-3-benzazepine being preferred. Thiazolo[4,5-c]azepine may be any of 4H-thiazolo[4,5-c]-azepine, 4H-thiazolo[4,5-d]azepine and 4H-thiazolo[5,4-c]-azepine, with 4H-thiazolo[4,5-d]azepine being preferred. Thieno[2,3-c]azepine may be any of 4H-thieno[2,3-d]azepine and 4H-thieno[3,2-c]azepine, with 4H-thieno[2,3-d]azepine being preferred.

Of these heterocyclic groups, the nitrogen-containing heterocyclic groups may be in the form of an N-oxide. Incidentally, the position of the above substituent group bonded to $Q^2$ is not particularly limited.

The above-described saturated or unsaturated, 5- or 6-membered cyclic hydrocarbon groups, saturated or unsaturated, 5- to 7-membered heterocyclic groups, saturated or unsaturated, bicyclic or tricyclic condensed hydrocarbon groups, and saturated or unsaturated, bicyclic or tricyclic condensed heterocyclic groups may each have 1 to 3 substituents. Examples of the substituents may include a hydroxyl group; halogen atoms such as fluorine atom, chlorine atom, bromine atom and iodine atom; halogenoalkyl groups having 1 to 3 halogen atoms; an amino group; a cyano group; an amidino group; a hydroxyamidino group; linear, branched, or cyclic alkyl groups having 1 to 6 carbon atoms (hereinafter referred to as $C_1$-$C_6$ alkyl groups which mean linear, branched and cyclic alkyl groups; for example, linear or branched $C_1$-$C_6$ alkyl groups such as methyl group, ethyl group, isopropyl group and tert-butyl group; $C_3$-$C_6$ cycloalkyl groups such as cyclopropyl group, cyclobutyl group, cyclopentyl group and 1-methylcyclopropyl group; and $C_3$-$C_6$ cycloalkyl-$C_1$-$C_6$ alkyl groups such as cyclopropylmethyl group; hydroxy-$C_1$-$C_6$ alkyl groups such as hydroxyethyl and 1,1-dimethyl-2-hydroxyethyl groups; $C_1$-$C_6$ alkoxy groups (for example, methoxy group, ethoxy group and the like); $C_1$-$C_6$ alkoxy-$C_1$-$C_6$ alkyl groups; a carboxyl group; $C_2$-$C_6$ carboxyalkyl groups (for example, carboxymethyl group and the like); $C_2$-$C_6$ alkoxycarbonyl-$C_1$-$C_6$ alkyl groups (for example, methoxycarbonylmethyl group, tert-butoxycarbonylmethyl group and the like); amidino groups substituted by a $C_2$-$C_6$ alkoxycarbonyl group; $C_2$-$C_6$ alkenyl groups (for example, vinyl group, allyl group and the like); $C_2$-$C_6$ alkynyl groups (for example, ethynyl group, propynyl group and the like); $C_2$-$C_6$ alkoxycarbonyl groups (for example, methoxycarbonyl group, ethoxycarbonyl group, tert-butoxycarbonyl group and the like); amino $C_1$-$C_6$ alkyl groups (for example, aminomethyl group, aminoethyl group and the like); $C_1$-$C_6$ alkylamino-$C_1$-$C_6$ alkyl groups (for example, N-methylaminomethyl group, N-ethylaminomethyl group and the like); di($C_1$-$C_6$ alkyl)amino-$C_1$-$C_6$ alkyl groups (for example, N,N-dimethylaminomethyl group, N,N-diethylaminomethyl group, N-ethyl-N-methylaminomethyl group and the like); $C_2$-$C_6$ alkoxycarbonylamino-$C_1$-$C_6$ alkyl groups (for example, methoxycarbonylaminoethyl group, tert-butoxycarbonylaminoethyl group and the like); $C_1$-$C_6$ alkanoyl groups (for example, formyl group, acetyl group, methylpropionyl group, cyclopentanecarbonyl group and the like); $C_1$-$C_6$ alkanoylamino-$C_1$-$C_6$ alkyl groups (for example, acetylaminomethyl group and the like); $C_1$-$C_6$ alkylsulfonyl groups (for example, methanesulfonyl group and the like); $C_1$-$C_6$ alkylsulfonylamino-$C_1$-$C_6$ alkyl groups (for example, methanesulfonylaminomethyl group and the like); a carbamoyl group; $C_1$-$C_6$ alkylcarbamoyl groups (for example, methylcarbamoyl group, ethylcarbamoyl group, isopropylcarbamoyl group, tert-butylcarbamoyl group and the like); N,N-di($C_1$-$C_6$ alkyl)carbamoyl groups (for example, dimethylcarbamoyl group, diethylcarbamoyl group, methylethylcarbamoyl group and the like); $C_1$-$C_6$ alkylamino groups (for example, N-methylamino group, N-ethylamino group and the like); di($C_1$-$C_6$ alkyl)amino groups (for example, N,N-dimethylamino group, N,N-diethylamino group, N-ethyl-N-methylamino group and the like); an aminosulfonyl group; arylsulfonyl groups (for example, phenylsulfonyl group and the like); arylcarbonyl groups which may be substituted by, for example, a halogen atom (for example, benzoyl group, 4-fluoro-benzoyl group and the like); $C_2$-$C_6$ alkoxycarbonyl ($C_1$-$C_6$ alkyl)amino $C_1$-$C_6$ alkyl groups (for example, methoxycarbonyl(methyl)aminomethyl group, tert-butoxycarbonyl(methyl)aminomethyl group and the like); $C_1$-$C_6$ alkylsulfonyl $C_1$-$C_6$ alkyl groups (for example, methylsulfonylmethyl group and the like); 5- or 6-membered heterocyclic groups containing one of nitrogen, oxygen, and sulfur, or the same or different two atoms thereof (for example, pyrrolidinyl group, piperidinyl group, piperazinyl group, morpholinyl group, pyridyl group, pyrimidinyl group, tetrahydropyranyl group and the like); the above 5- or 6-membered heterocyclic-$C_1$-$C_4$ alkyl groups (for example, morpholinomethyl group and the like); the above 5- or 6-membered heterocyclic-carbonyl groups (for example, pyrrolidinocarbonyl group and the like); the above 5- or 6-membered heterocyclic-amino-$C_1$-$C_4$ alkyl groups (for example, N-(oxazol-2-yl)aminomethyl group and the like); the above 5- or 6-membered heterocyclic-amino groups (for example, pyridylamino group and the like); the above 5- or 6-membered heterocyclic-oxy groups (for example, 4-pyridinyloxy group, (1-methyliminopiperidin-4-yl)oxy group and the like); 3- to 6-membered heterocyclic-carbonyl-$C_1$-$C_4$ alkyl groups (for example, 4,4-dioxothiomorpholin-1-yl)carbonylmethyl group and the like); and the above 5- or 6-membered heterocyclic ($C_1$-$C_6$ alkyl)amino-$C_1$-$C_4$ alkyl groups (for example, N-(4,5-dihydro-1,3-oxazol-2-yl)-N-methylaminomethyl group and the like).

As specific examples of $Q^1$, may be mentioned 5- or 6-membered cyclic hydrocarbon groups such as 2-aminosulfonylphenyl group; bicyclic heterocyclic groups such as 5-methyl-4,5,6,7-tetrahydrothiazolo[5,4-c]pyridin-2-yl, 4,5,6,7-tetrahydrothiazolo[5,4-c]pyridin-2-yl, 5-cyclopropyl-4,5,6,7-tetrahydrothiazolo[5,4-c]pyridin-2-yl, 5-carboxymethyl-4,5,6,7-tetrahydrothiazolo[5,4-c]pyridin-2-yl, 5-butyl-4,5,6,7-tetrahydrothiazolo[5,4-c]pyridin-2-yl, 5-(4-pyridyl)-4,5,6,7-tetrahydrothiazolo[5,4-c]-pyridin-2-yl, 5-methyl-4,5,6,7-tetrahydrothiazolo[4,5-c]pyridin-2-yl, 6-methyl-4,5,6,7-tetrahydrothieno[2,3-c]pyridin-2-yl, 5-methyl-4,5,6,7-tetrahydroxazolo[5,4-c]pyridin-2-yl, 5-methyl-4,6-dihydro-5H-pyrrolo[3,4-d]thiazol-2-yl, 5,7-dihydro-6-methylpyrrolo[3,4-d]pyrimidin-2-yl, 5,6-dimethyl-4,5,6,7-tetrahydrothiazolo[4,5-d]pyridazin-2-yl, 5,6-dimethyl-4,5,6,7-tetrahydroxazolo[4,5-d]pyridazin-2-yl, 5-dimethylamino-4,5,6,7-tetrahydrobenzo[d]thiazol-2-yl, 5-(4-pyridyl)-4,5,6,7-tetrahydrothiazolo[5,4-c]pyridin-2-yl and 6,7-dihydro-4H-pyrano[4,3-d]thiazol-2-yl groups; and 5- or 6-membered heterocyclic groups such as pyridyl groups such as 4-pyridyl and 2-pyridyl; dihydroxazolyl groups such as 4,5-dihydroxazol-2-yl; 4-[N-(4,5-dihydroxazol-2-yl)-N-methylaminomethyl]thiophen-2-yl, 4-[N-(4,5-dihydroxazol-2-yl)-N-methylaminomethyl]-3-chlorothiophen-2-yl, 5-(N-methylaminomethyl)thiazol-2-yl, 5-(N-methylaminomethyl)thiophen-2-yl, 5-(N,N-dimethylaminomethyl)thiazol-2-yl, 5-(N,N-dimethylaminomethyl)thiophen-2-yl and 5-(N,N-dimethylaminomethyl)pyridin-2-yl groups.

Next will be described $Q^2$. Examples of the linear or branched alkylene group having 1 to 6 carbon atoms include methylene, ethylene, trimethylene, propylene, tetramethylene, pentamethylene and hexamethylene groups.

Examples of the linear or branched alkenylene group having 2 to 6 carbon atoms include vinylene, propenylene, butenylene and pentenylene groups. No particular limitation is imposed on the position of a carbon-carbon double bond.

Examples of the linear or branched alkynylene group having 2 to 6 carbon atoms include ethynylene, propynylene, butynylene, pentynylene and hexynylene groups. No particular limitation is imposed on the position of a carbon-carbon triple bond.

The saturated or unsaturated, 5- or 6-membered divalent cyclic hydrocarbon group means a divalent group derived from the saturated or unsaturated, 5- or 6-membered cyclic hydrocarbon described in the description of $Q^3$. As specific examples thereof, may be mentioned cyclohexylene, cyclohexenylene and phenylene groups, with cyclohexylene and phenylene groups being preferred.

The saturated or unsaturated, 5- to 7-membered divalent heterocyclic group means a divalent group derived from the saturated or unsaturated, 5- to 7-membered heterocyclic ring described in the description of $Q^3$. As specific examples thereof, may be mentioned divalent groups derived from furan, pyrrole, thiophene, pyrazole, imidazole, oxazole, oxazolidine, thiazole, thiadiazole, furazane, pyrane, pyridine, pyrimidine, pyridazine, pyrrolidine, piperazine, piperidine, oxazine, oxadiazine, morpholine, thiazine, thiadiazine, thiomorpholine, tetrazole, triazole, triazine, azepine, diazepine and triazepine. Among these, preferable examples thereof include divalent groups derived from pyrazole, imidazole, oxazole, thiazole, thiadiazole, furazane, pyridine, pyrimidine, pyridazine, pyrrolidine, piperazine, piperidine, triazole, triazine, azepine, diazepine and triazepine.

The saturated or unsaturated, divalent bicyclic or tricyclic condensed hydrocarbon means a divalent group derived from the saturated or unsaturated, bicyclic or tricyclic condensed hydrocarbon group described in the description of $Q^3$ in formula (1). As specific examples thereof, may be mentioned divalent groups derived from indene, indane, naphthalene, tetrahydronaphthalene, anthracene, phenanthrene and the like. As preferable examples thereof, may be mentioned divalent groups derived from indane and naphthalene.

The saturated or unsaturated, divalent bicyclic or tricyclic condensed heterocyclic group means a divalent group derived from the saturated or unsaturated, bicyclic or tricyclic condensed heterocyclic ring described in the description of $Q^3$ in formula (1). As specific examples thereof, may be mentioned divalent groups derived from benzofuran, benzothiophene, indole, isoindole, indazole, quinoline, tetrahydroquinoline, isoquinoline, tetrahydroisoquinoline, quinazoline, dihydroquinazoline, tetrahydroquinazoline, quinoxaline, tetrahydroquinoxaline, cinnoline, tetrahydrocinnoline, indolizine, tetrahydroindolizine, benzothiazole, tetrahydrobenzothiazole, naphthyridine, tetrahydronaphthyridine, thienopyridine, tetrahydrothienopyridine, thiazolopyridine, tetrahydrothiazolopyridine, thiazolopyridazine, tetrahydrothiazolopyridazine, pyrrolopyridine, dihydropyrrolopyridine, tetrahydropyrrolopyridine, pyrrolopyrimidine, dihydropyrrolopyrimidine, dihydropyridoquinazoline, pyranothiazole, dihydropyranothiazole, furopyridine, tetrahydrofuropyridine, oxazolopyridine, tetrahydroxazolopyridine, oxazolopyridazine, tetrahydroxazolopyridazine, pyrrolothiazole, dihydropyrrolothiazole, pyrrolooxazole, dihydropyrrolooxazole and benzazepine. As preferable examples thereof, may be mentioned divalent groups derived from benzofuran, benzothiophene, indole, indazole, quinoline, isoquinoline, tetrahydroisoquinoline, benzothiazole, naphthyridine, thienopyridine, thiazolopyridine, tetrahydrothiazolopyridine, thiazolopyridazine, pyrrolopyridine, tetrahydropyrrolopyridine, pyridopyrimidine, pyranothiazole, dihydropyranothiazole, furopyridine, oxazolopyridine, oxazolopyridazine, pyrrolothiazole, dihydropyrrolothiazole, pyrrolooxazole and dihydropyrrolooxazole. No particular limitation is imposed on the condensing form of the condensed heterocyclic group. For example, naphthyridine may be any of 1,5-, 1,6-, 1,7-, 1,8-, 2,6-, and 2,7-naphthyridine; thienopyridine may be any of thieno[2,3-b]pyridine, thieno[2,3-c]pyridine, thieno[3,2-b]pyridine, thieno[3,2-c]pyridine, thieno[3,4-b]pyridine, and thieno[3,4-c]pyridine; thiazolopyridine may be any of thiazolo[4,5-b]pyridine, thiazolo[4,5-c]pyridine, thiazolo[5,4-b] pyridine, thiazolo[5,4-c]pyridine, thiazolo[3,4-a]pyridine and thiazolo[3,2-a]pyridine, thiazolopyridazine may be any of thiazolo[4,5-c]pyridazine, thiazolo[4,5-d]pyridazine, thiazolo[5,4-c]pyridazine and thiazolo[3,2-b]pyridazine, pyrrolopyridine may be any of pyrrolo[2,3-b]pyridine, pyrrolo[2,3-c]pyridine, pyrrolo[3,2-b]pyridine, pyrrolo[3,2-c]pyridine, pyrrolo[3,4-b]pyridine and pyrrolo[3,4-c]pyridine, pyrrolopyrimidine may be any of pyrrolo[3,4-d]pyrimidine, pyrrolo[3,2-d]pyrimidine, and pyrrolo[2,3-d]pyrimidine; pyridopyrimidine may be any of pyrido[2,3-d]pyrimidine, pyrido[3,2-d]pyrimidine, and pyrido[3,4-d]pyrimidine; pyranothiazole may be any of pyrano[2,3-d]thiazole, pyrano[4,3-d]thiazole, pyrano[3,4-d]thiazole, and pyrano[3,2-d]thiazole; furopyridine may be any of furo[2,3-b]pyridine, furo[2,3-c]pyridine, furo[3,2-b]pyridine, furo[3,2-c]pyridine, furo[3,4-b]pyridine, and furo[3,4-c]pyridine; oxazolopyridine may be any of oxazolo[4,5-b]pyridine, oxazolo[4,5-c]pyridine, oxazolo[5,4-b]pyridine, oxazolo[5,4-c]pyridine, oxazolo[3,4-a]pyridine, and oxazolo[3,2-a]pyridine; oxazolopyridazine may be any of oxazolo[4,5-c]pyridazine, oxazolo[4,5-d]pyridazine, oxazolo[5,4-c]pyridazine, and oxazolo[3,4-b]pyridazine; pyrrolothiazole may be any of pyrrolo[2,1-b]thiazole, pyrrolo[1,2-c]thiazole, pyrrolo[3,2-d]thiazole, and pyrrolo[3,4-d] thiazole; and pyrrolooxazole may be any of pyrrolo[2,1-b] oxazole, pyrrolo[1,2-c]oxazole, pyrrolo[2,3-d]oxazole, pyrrolo[3,2-d]oxazole, and pyrrolo[3,4-d]oxazole. Other condensing forms than these may be allowed.

The above-described saturated or unsaturated, 5- or 6-membered divalent cyclic hydrocarbon groups, saturated or unsaturated, 5- to 7-membered divalent heterocyclic groups, saturated or unsaturated, divalent bicyclic or tricyclic condensed hydrocarbon groups and saturated or unsaturated, divalent bicyclic or tricyclic condensed heterocyclic groups may each have 1 to 3 substituents. Examples of the substituents may include a hydroxyl group, halogen atoms such as a fluorine, chlorine, bromine and iodine atoms, halogenoalkyl groups having 1 to 3 halogen atoms, an amino group, a cyano group, aminoalkyl groups, an amidino group, a hydroxyamidino group, linear, branched, or cyclic alkyl groups having 1 to 6 carbon atoms (for example, methyl group, ethyl group, etc.), linear, branched, or cyclic alkoxy groups having 1 to 6 carbon atoms (for example, methoxy group, ethoxy group, etc.), an amidino group substituted by a linear, branched, or cyclic alkoxycarbonyl groups having 2 to 7 carbon atoms (for example, methoxycarbonylamidino group, ethoxycarbonylamidino group, etc.), linear, branched, or cyclic alkenyl groups having 2 to 6 carbon atoms (for example, vinyl group, allyl group, etc.), linear or branched alkynyl groups having 2 to 6 carbon atoms (for example, ethynyl group, propynyl group, etc.), linear, branched, or cyclic alkoxycarbonyl group having 2 to 6 carbon atoms (for example, methoxycarbonyl group, ethoxycarbonyl group, etc.), and a carbamoyl group.

Preferable groups in $Q^2$ described above are a single bond, saturated or unsaturated, 5- or 6-membered divalent cyclic hydrocarbon groups which may be substituted, saturated or unsaturated, 5- to 7-membered divalent heterocyclic groups which may be substituted, and saturated or unsaturated, divalent bicyclic or tricyclic condensed heterocyclic groups which may be substituted. Of these, a single bond, saturated or unsaturated, divalent 5- or 6-membered cyclic hydrocarbon groups, saturated or unsaturated, 5- to 7-membered divalent heterocyclic groups are more preferred.

When $Q^1$ is a saturated or unsaturated, bicyclic or tricyclic condensed hydrocarbon group which may be substituted, or a saturated or unsaturated, bicyclic or tricyclic condensed heterocyclic group which may be substituted, the group $Q^2$ is preferably a single bond.

Specifically, more preferred are those in which the group $Q^1$ is a thienopyridyl group which may be substituted; a tetrahydrothienopyridyl group which may be substituted; a thiazolopyridyl group which may be substituted; a tetrahydrothiazolopyridyl group which may be substituted; a thiazolopyridazinyl group which may be substituted; a tetrahydrothiazolopyridazinyl group which may be substituted; a pyranothiazolyl group which may be substituted; a dihydropyranothiazolyl group which may be substituted; a furopyridyl group which may be substituted; a tetrahydrofuropyridyl group which may be substituted; an oxazolopyridyl group which may be substituted; a tetrahydroxazolopyridyl group which may be substituted; a pyrrolopyridyl group which may be substituted; a dihydropyrrolopyridyl group which may be substituted; a tetrahydropyrrolopyridyl group which may be substituted; a pyrrolopyrimidinyl group which may be substituted; a dihydropyrrolopyrimidinyl group which may be substituted; an oxazolopyridazinyl group which may be substituted; a tetrahydroxazolopyridazinyl group which may be substituted; a pyrrolothiazolyl group which may be substituted; a dihydropyrrolothiazolyl group which may be substituted; a pyrrolooxazolyl group which may be substituted; a dihydropyrrolooxazolyl group which may be substituted; a benzothiazolyl group which may be substituted; a tetrahydrobenzothiazolyl group which may be substituted; a thiazolopyrimidinyl which may be substituted; a dihydrothiazolopyrimidinyl which may be substituted; a benzazepinyl which may be substituted; a tetrahydrobenzazepinyl which may be substituted; a thiazoloazepinyl which may be substituted; a tetrahydrothiazoloazepinyl which may be substituted; a thienoazepinyl which may be substituted; a tetrahydrothienoazepinyl which may be substituted; a 4,5,6,7-tetrahydro-5,6-tetramethylenethiazolopyridazinyl group which may be substituted; or a 5,6-trimethylene-4,5,6,7-tetrahydrothiazolopyridazinyl group which may be substituted, and $Q^2$ is a single bond.

When $Q^1$ is a saturated or unsaturated, 5- or 6-membered cyclic hydrocarbon group which may be substituted, or a saturated or unsaturated, 5- to 7-membered heterocyclic group which may be substituted, the group $Q^2$ is preferably a saturated or unsaturated, 5- or 6-membered divalent cyclic hydrocarbon group which may be substituted, or a saturated or unsaturated, 5- to 7-membered divalent heterocyclic group which may be substituted. As preferable examples of the group $Q^1$-$Q^2$-, may be mentioned 4-(4-pyridyl)phenyl, 4-(2-pyridyl)phenyl, 5-(4-pyridyl)thiazolyl, 1-(4-pyridyl)piperidyl, 4-(4-pyridyl)piperidyl, 4-hydroxy-1-(4-pyridyl)piperidin-4-yl, biphenylyl, 4-(2-aminosulfonylphenyl)phenyl, 4-(2-amidinophenyl)phenyl, 4-(2-methylsulfonylphenyl)phenyl, 4-(2-aminomethylphenyl)phenyl, 4-(2-carbamoylphenyl)phenyl, 4-(2-imidazolyl)phenyl, 4-(1-methyl-2-imidazolyl)phenyl, 4-(2,3,4,5-tetrahydropyrimidin-2-yl)phenyl, 4-(1-methyl-2,3,4,5-tetrahydropyrimidin-2-yl)phenyl, 4-(5-tetrazolyl)phenyl, 1-(4-pyridyl)piperidin-4-yl, 3-(4-piperidyl)isoxazolin-5-yl, 3-(4-amidinophenyl)isoxazolin-5-yl, 3-(4-piperidyl)isoxazolidin-5-yl, 3-(4-amidinophenyl)isoxazolidin-5-yl, 2-(4-piperidyl)-1,3,4-thiadiazol-5-yl, 2-(4-aminophenyl)-1,3,4-oxadiazol-5-yl, 4-(4-piperidyl)piperidin-1-yl, 4-(4-piperidyl)piperazin-1-yl, 4-(4-piperazinyl)piperazin-1-yl, 1-(4-pyrimidinyl)piperidin-1-yl, 1-(2-methylpyrimidin-4-yl)piperidin-4-yl, 1-(4-pyrimidinyl)pyrrolidin-3-yl, 1-(4-methylpyrimidin-6-yl)piperazin-4-yl, 1-(2-methylpyrimidin-4-yl)pyrrolidin-4-yl, 1-(6-chloropyrimidin-4-yl)piperidin-4-yl, 5-(4-chlorophenyl)thiophen-2-yl, 2-(4-chlorophenyl)thiazol-4-yl, 3-(4-chlorophenyl)-1H-pyrrol-2-yl, 4-(4-pyrimidinyl)phenyl, 4-(4-imidazolyl)phenyl, 5-(pyridin-4-yl)pyrimidin-2-yl, 2'-[(dimethylamino)methyl][1,1'-biphenyl]-4-yl, 4-[2-(hydroxymethyl)pyridin-4-yl]phenyl, 4-[2-(aminomethyl)pyridin-4-yl]phenyl, 2'-(aminosulfonyl)[1,1'-biphenyl]-4-yl and 4-(3-oxomorpholin-4-yl)phenyl groups.

The group $T^1$ represents a carbonyl group, sulfonyl group, group —C(=O)—C(=O)—N(R')—, group —C(=S)—C(=O)—N(R')—, group —C(=O)—C(=S)—N(R')—, group —C(=S)—C(=S)—N(R')— (in which R' represents a hydrogen atom, hydroxyl group, alkyl group or alkoxy group), group —C(=O)-$A^1$-N(R")— (in which $A^1$ represents an alkylene group having 1 to 5 carbon atoms, which may be substituted, and R" represents a hydrogen atom, hydroxyl group, alkyl group or alkoxy group), group —C(=O)—NH—, group —C(=S)—NH—, group —C(=O)—NH—NH—, group —C(=O)-$A^2$-C(=O)— (in which $A^2$ represents a single bond or alkylene group having 1 to 5 carbon atoms), group —C(=O)-$A^3$-C(=O)—NH— (in which $A^3$ represents an alkylene group having 1 to 5 carbon atoms), group —C(=O)—C(=NOR$^a$)—N(R$^b$)—, group —C(=S)—C(=NOR$^a$)—N(R$^b$)— (in which R$^a$ represents a hydrogen atom, alkyl group or alkanoyl group, and R$^b$ represents a hydrogen atom, hydroxyl group, alkyl group or alkoxy group), group —C(=O)—N=N—, group —C(=S)—N=N—, group —C(=NOR$^c$)—C(=O)—N(R$^d$) (in which R$^c$ represents a hydrogen atom, alkyl group, alkanoyl group, aryl group or aralkyl group, and R$^d$ represents a hydrogen atom, hydroxyl group, alkyl group or alkoxy group), group —C(=N—N(R$^e$)(R$^f$))—C(=O)—N(R$^g$)— (in which R$^e$ and R$^f$ each independently represent a hydrogen atom, alkyl group, alkanoyl group or alkyl(thiocarbonyl) group, and R$^g$ represents a hydrogen atom, hydroxyl group, alkyl group or alkoxy group), group —C(=O)—NH—C(=O)—, group —C(=S)—NH—C(=O)—, group —C(=O)—NH—C(=S)—, group —C(=S)—NHC(=S)—, group —C(=O)—NH—SO$_2$—, group —SO$_2$—NH—, group —C(=NCN)—NH—C(=O)—, group —C(=S)—C(=O)—, or thiocarbonyl group.

In the above groups, the alkylene group having 1 to 5 carbon atoms in $A^1$, $A^2$ and $A^3$ represents a linear, branched, or cyclic alkylene group having 1 to 5 carbon atoms, and examples thereof include methylene, ethylene, propylene, cyclopropylene, 1,3-cyclopentylene groups and the like. The alkyl group in R', R", R$^a$, R$^b$, R$^c$, R$^d$, R$^e$, R$^f$ and R$^g$ represents a linear, branched, or cyclic alkyl group having 1 to 6 carbon atoms, and examples thereof include methyl, ethyl groups and the like. The alkoxy group means a linear, branched, or cyclic alkoxy group having 1 to 6 carbon atoms, and examples thereof include methoxy, ethoxy groups and the like.

In R$^a$, R$^c$, R$^e$ and R$^f$, the alkanoyl group means a group composed of a linear, branched, or cyclic alkyl group having 1 to 6 carbon atoms and a carbonyl group, and examples thereof include acetyl, propionyl groups and the like.

In R$^c$, the aryl group means an aryl group having 6 to 14 carbon atoms, and examples thereof include phenyl, naphthyl groups and the like. The aralkyl group means a linear, branched, or cyclic alkyl group having 1 to 6 carbon atoms substituted with the aryl group having 6 to 14 carbon atoms, and examples thereof include benzyl, phenethyl groups and the like.

As $T^1$, is preferred a carbonyl group, group —C(=O)—C(=O)—N(R')—, group —C(=S)—C(=O)—N(R')—, group —C(=O)—C(=S)—N(R')—, group —C(=S)—C(=S)—N(R')—, and group —C(=O)—CH$_2$—N(R")—, with a carbonyl group, group —C(=O)—C(=O)—N(R')—, group —C(=S)—C(=O)—N(R')—, group —C(=O)—C(=S)—N(R')— and group —C(=S)—C(=S)—N(R')— being particularly preferred.

In one preferred case, $T^1$ is a carbonyl group or a sulfonyl group, and $Q^3$ is, among the aforementioned twelve groups, any of (b), (f), (g), (h), (i), (j), (k), and (l) (note that N in (f) indicates that 2 carbon atoms of the ring substituted by $R^{19}$ have been substituted by a nitrogen atom).

In another preferred case, $T^1$ is group —C(=O)—C(=O)—N(R')—, group —C(=S)—C(=O)—N(R')—, group —C(=O)—C(=S)—N(R')—, or group —C(=S)—C(=S)—N(R')—, and $Q^3$ is, among the aforementioned twelve groups, any of (i), (j), and (k).

Steps (i) to (k) will next be described in detail.

<Step (i)>

In Step (i), Compound (X) is produced.

Compound (X) may be produced through reacting Compound (VI-I) with Compound (IX) or a salt thereof in the presence of an appropriate base in an inert solvent at −78° C. to 150° C. Examples of the salt of Compound (IX) include alkali metal salts and alkaline earth metal salts such as sodium salts, potassium salts, lithium salts, magnesium salts, and calcium salts.

Specific examples of the base employed in any one of the Steps include alkali metal or alkaline earth metal carbonates such as sodium carbonate and potassium carbonate; alkali metal alkoxides such as sodium ethoxide and potassium butoxide; alkali metal hydroxides such as sodium hydroxide and potassium hydroxide; alkali metal hydrides such as sodium hydride and potassium hydride; organometallic bases such as alkyl lithium (e.g., n-butyl lithium) and dialkylamino lithiums (e.g., lithium diisopropylamide); bis(silyl)amine organometallic bases such as lithium bis(trimethylsilyl)amide; and organic bases such as pyridine, 2,6-lutidine, collidine, 4-dimethylaminopyridine, triethylamine, N-methylmorpholine, diisopropylethylamine, and diazabicyclo[5.4.0]undec-7-ene (DBU).

Examples of the inert solvent used in this reaction include alkyl halide solvents such as dichloromethane, chloroform, and carbon tetrachloride; ether solvents such as tetrahydrofuran, 1,2-dimethoxyethane, and dioxane; aromatic solvents such as benzene and toluene; and amide solvents such as N,N-dimethylformamide, N,N-dimethylacetamide, and N-methylpyrrolidin-2-one. In addition to these solvents, a sulfoxide solvent such as dimethyl sulfoxide or sulfolane; a ketone solvent such as acetone or methyl ethyl ketone; acetonitrile; (C1-C4 alkyl)acetate esters; and acetone may also be used.

If required, Compound (IX) may be transformed into a mixed acid anhydride, an acid halide, an active ester, or the like, before being reacted. In this reaction, reagents and conditions generally used in peptide synthesis may be applied. The mixed acid anhydride may be prepared by, for example, reaction of a chloroformate such as ethyl chloroformate or isobutyl chloroformate with Compound (IX) in the presence of a base. The acid halide may be prepared by treating Compound (IX) with an acid halide such as thionyl chloride or oxalyl chloride. The activated ester includes various kinds of esters. Such an ester may be prepared by, for example, reacting a compound such as phenol (e.g., p-nitrophenol), N-hydroxybenzotriazole, or N-hydroxysuccinimide with Compound (IX) using a condensing agent such as N,N'-dicyclohexylcarbodiimide or 1-ethyl-3-(3-dimethylaminopropyl)carbodiimide hydrochloride. The activated ester can also be prepared by reaction of Compound (IX) with pentafluorophenyl trifluoroacetate or the like, reaction of Compound (IX) with 1-benzotriazolyloxytripyrrolidinophosphonium hexafluorophosphite, reaction of Compound (IX) with diethyl cyanophosphonate (Shioiri method), reaction of Compound (IX) with triphenylphosphine and 2,2'-dipyridyl disulfide (Mukaiyama method), or the like. The thus-obtained mixed acid anhydride, acid halide or activated ester of Compound (IX) may be reacted with Compound (VI-I) at −78° C. to 150° C. in the presence of an appropriate base in an inert solvent, to thereby produce Compound (A).

Specific examples of the base employed in any one of the Steps include alkali metal or alkaline earth metal carbonates such as sodium carbonate and potassium carbonate; alkali metal alkoxides such as sodium ethoxide and potassium butoxide; alkali metal hydroxides such as sodium hydroxide and potassium hydroxide; alkali metal hydrides such as sodium hydride and potassium hydride; organometallic bases such as alkyl lithium (e.g., n-butyl lithium) and dialkylamino lithiums (e.g., lithium diisopropylamide); bis(silyl)amine organometallic bases such as lithium bis(trimethylsilyl) amide; and organic bases such as pyridine, 2,6-lutidine, collidine, 4-dimethylaminopyridine, triethylamine, N-methylmorpholine, diisopropylethylamine, and diazabicyclo[5.4.0]undec-7-ene (DBU).

Examples of the inert solvent used in this reaction include alkyl halide solvents such as dichloromethane, chloroform, and carbon tetrachloride; ether solvents such as tetrahydrofuran, 1,2-dimethoxyethane, and dioxane; aromatic solvents such as benzene and toluene; and amide solvents such as N,N-dimethylformamide, N,N-dimethylacetamide, and N-methylpyrrolidin-2-one. In addition to these solvents, a sulfoxide solvent such as dimethyl sulfoxide or sulfolane; a ketone solvent such as acetone or methyl ethyl ketone; acetonitrile; (C1-C4 alkyl)acetate esters; and acetone may also be used.

<Step (j)>

In Step (j), Compound (XI) or a salt thereof is produced through removing the protective group ($R^1$) from Compound (X) or a salt thereof.

The deprotection conditions may be selected in accordance with the type of the protective group, and generally employed reagents and conditions may be employed. For example, when the protective group is a tert-butoxycarbonyl group, deprotection is performed at −20 to 70° C. by use of an acid such as trifluoroacetic acid, hydrochloric acid, sulfuric acid, p-toulenesulfonic acid, or methanesulfonic acid.

<Step (k)>

In Step (k), Compound (A) is produced. If required, Carboxylic acid (XII) or a salt thereof may be transformed into a mixed acid anhydride, an acid halide, an active ester, or the like, before being reacted. In this reaction, reagents and conditions generally used in peptide synthesis may be applied. The mixed acid anhydride may be prepared by, for example, reaction of a chloroformate such as ethyl chloroformate or isobutyl chloroformate with Carboxylic acid (XII) in the presence of a base. The acid halide may be prepared by treating Carboxylic acid (XII) with an acid halide such as thionyl chloride or oxalyl chloride. The activated ester includes various kinds of esters. Such an ester may be prepared by, for example, reacting a compound such as phenol (e.g., p-nitrophenol), N-hydroxybenzotriazole, or N-hydroxysuccinimide with Carboxylic acid (XII) using a condensing agent such as N,N'-dicyclohexylcarbodiimide or 1-ethyl-3-(3-dimethylaminopropyl)carbodiimide hydrochloride. The activated ester can also be prepared by reaction of Carboxylic acid (XII) with pentafluorophenyl trifluoroacetate or the like, reaction of Carboxylic acid (XII) with 1-benzotriazolyloxytripyrrolidinophosphonium hexafluorophosphite, reaction of Carboxylic acid (XII) with diethyl cyanophosphonate (Shioiri method), reaction of Carboxylic acid (XII) with triphenylphosphine and 2,2'-dipyridyl disulfide (Mukaiyama method), or the like. The thus-obtained mixed acid anhydride, acid halide or activated ester of Carboxylic acid (XII) may be reacted with Compound (X-I) at −78° C. to 150° C. in the presence of an appropriate base in an inert solvent, to thereby produce Compound (A).

Specific examples of the base employed in any one of the Steps include alkali metal or alkaline earth metal carbonates such as sodium carbonate and potassium carbonate; alkali metal alkoxides such as sodium ethoxide and potassium butoxide; alkali metal hydroxides such as sodium hydroxide and potassium hydroxide; alkali metal hydrides such as sodium hydride and potassium hydride; organometallic bases such as alkyl lithium (e.g., n-butyl lithium) and dialkylamino lithiums (e.g., lithium diisopropylamide); bis(silyl)amine organometallic bases such as lithium bis(trimethylsilyl) amide; and organic bases such as pyridine, 2,6-lutidine, collidine, 4-dimethylaminopyridine, triethylamine, N-methylmorpholine, diisopropylethylamine, and diazabicyclo[5.4.0]undec-7-ene (DBU).

Examples of the inert solvent used in this reaction include alkyl halide solvents such as dichloromethane, chloroform, and carbon tetrachloride; ether solvents such as tetrahydrofuran, 1,2-dimethoxyethane, and dioxane; aromatic solvents such as benzene and toluene; and amide solvents such as N,N-dimethylformamide, N,N-dimethylacetamide, and N-methylpyrrolidin-2-one. In addition to these solvents, a sulfoxide solvent such as dimethyl sulfoxide or sulfolane; a ketone solvent such as acetone or methyl ethyl ketone; acetonitrile; (C1-C4 alkyl)acetate esters; and acetone may also be used in some cases.

Examples of the salt of Carboxylic acid (XII) include alkali metal salts and alkaline earth metal salts thereof, for example, sodium salts, potassium salts, lithium salts, magnesium salts, and calcium salts.

Compound A may include stereoisomers or optical isomers attributed to an asymmetric carbon. However, these stereoisomers, optical isomers and mixtures thereof are all included in the present invention.

No particular limitation is imposed on the salt of Compound (A) so long as the salt is pharmaceutically acceptable. However, specific examples thereof include mineral acid salts such as hydrochlorides, hydrobromides, hydroiodides, phosphates, nitrates and sulfates; benzoates; organic sulfonates such as methanesulfonates, 2-hydroxyethanesulfonates and p-toluenesulfonates; and organic carboxylates such as acetates, propanoates, oxalates, malonates, succinates, glutarates, adipates, tartrates, maleates, malates, citrates, and mandelates.

In the case where Compound (A) has an acidic group, the salt may be formed with an alkali metal ion or an alkaline earth metal ion. Compound (A) or a salt thereof may be in the form of solvate, and no particular limitation is imposed on the solvate thereof so far as it is pharmaceutically acceptable. As specific examples thereof, however, may be mentioned hydrates and solvates with ethanol. When a nitrogen atom is present in Compound (A), such a compound may be converted to an N-oxide thereof.

As Compound (A), particularly preferred are the following compounds and salts, and solvates of any of these.

N-{(1R*,2S*,5S*)-2-{[(5-chloroindol-2-yl)carbonyl]amino}-5-[(dimethylamino)carbonyl]cyclohexyl}-5-methyl-4,5,6,7-tetrahydrothiazolo[5,4-c]pyridine-2-carboxamide hydrochloride, N-{(1R,2S,5S)-2-{[(5-chloroindol-2-yl)carbonyl]amino}-5-[(dimethylamino)carbonyl]cyclohexyl}-5-methyl-4,5,6,7-tetrahydrothiazolo[5,4-c]pyridine-2-carboxamide hydrochloride, N-{(1R*,2S*,4S*)-2-{[(5-chloroindol-2-yl)carbonyl]amino}-4-[(dimethylamino)carbonyl]cyclohexyl}-5-methyl-4,5,6,7-tetrahydrothiazolo[5,4-c]pyridine-2-carboxamide hydrochloride, 6-chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-2-quinolinecarboxamide hydrochloride, N-{(1R,2S,5S)-2-{[(5-chloro-4-fluoroindol-2-yl)carbonyl]amino}-5-[(dimethylamino)carbonyl]cyclohexyl}-5-methyl-4,5,6,7-tetrahydrothiazolo[5,4-c]pyridine-2-carboxamide hydrochloride, 7-chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)isoquinoline-3-carboxamide hydrochloride, $N^1$-(4-chlorophenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, $N^1$-(3-chlorophenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, $N^1$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-$N^2$-(4-fluorophenyl)ethanediamide hydrochloride, $N^1$-(4-bromophenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, $N^1$-(4-chloro-2-methylphenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, $N^1$-(4-chloro-3-methylphenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, $N^1$-(4-chloro-2-fluorophenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, $N^1$-(2,4-dichlorophenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, $N^1$-(3,4-dichlorophenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide, $N^1$-(2,4-difluorophenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide, $N^1$-(3,4-difluorophenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide, $N^1$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-$N^2$-(pyridin-4-yl)ethanediamide hydrochloride, $N^1$-(5-bromopyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, $N^1$-(6-chloropyridin-3-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, $N^1$-(6-chloropyridazin-3-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, $N^1$-(5-chlorothiazol-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, $N^1$-(5-chloropyridin-2-yl)-$N^2$-((1S,2R,4S)-4-[(dimethylamino)carbonyl]-2-{[(5-methyl-5,6-dihydro-4H-pyrrolo[3,4-d]thiazol-2-yl)carbonyl]amino}cyclohexyl)ethanediamide hydrochloride, N-{(1R,2S,5S)-2-{[2-(4-chloroanilino)acetyl]amino}-5-[(dimethylamino)carbonyl]cyclohexyl}-5-methyl-4,5,6,7-tetrahydrothiazolo[5,4-c]pyridine-2-carboxamide hydrochloride, N-{(1R,2S,5S)-2-{[2-(4-chloro-2-fluoroanilino)acetyl]amino}-5-[(dimethylamino)carbonyl]cyclohexyl}-5-methyl-4,5,6,7-tetrahydrothiazolo[5,4-c]pyridine-2-carboxamide hydrochloride, N-{(1R,2S,5S)-2-{[(5-chloroindol-2-yl)carbonyl]amino}-5-[(dimethylamino)carbonyl]cyclohexyl}-4,5,6,7-tetrahydrothiazolo[5,4-c]pyridine-2-carboxamide hydrochloride, N-{(1R,2S,5S)-2-{[(5-chloroindol-2-yl)carbonyl]amino}-5-[(dimethylamino)carbonyl]cyclohexyl}-5-(4,5-dihydrooxazol-2-yl)-4,5,6,7-tetrahydrothiazolo[5,4-c]pyridine-2-carboxamide, N-{(1R,2S,5S)-2-{[(5-chloro-4-fluoroindol-2-yl)carbonyl]amino}-5-[(dimethylamino)carbonyl]cyclohexyl}-5-methyl-4,5,6,7-tetrahydrothiazolo[5,4-c]pyridine-2-carboxamide hydrochloride, N-{(1R,2S,5S)-2-{[(5-chloro-3-fluoroindol-2-yl)carbonyl]amino}-5-[(dimethylamino)carbonyl]cyclohexyl}-5-methyl-4,5,6,7-tetrahydrothiazolo[5,4-c]pyridine-2-carboxamide hydrochloride, N-{(1R,2S,5S)-2-{[(3-bromo-5-chloroindol-2-yl)carbonyl]amino}-5-[(dimethylamino)carbonyl]cyclohexyl}-5-methyl-4,5,6,7-tetrahydrothiazolo[5,4-c]pyridine-2-carboxamide hydrochloride, N-{(1R,2S,5S)-2-{[(3-chloro-5-fluoroindol-2-yl)carbonyl]amino}-5-[(dimethylamino)carbonyl]cyclohexyl}-5-methyl-4,5,6,7-tetrahydrothiazolo[5,4-c]pyridine-2-carboxamide hydrochloride, N-{(1R,2S,5S)-2-{[(5-chloro-3-formylindol-2-yl)carbonyl]amino}-5-[(dimethylamino)carbonyl]cyclohexyl}-5-methyl-4,5,6,7-tetrahydrothiazolo[5,4-c]pyridine-2-carboxamide hydrochloride, 5-chloro-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-$N^3$,$N^3$-dimethylindole-2,3-dicarboxamide hydrochloride, N-{(1R,2S,5S)-2-[(6-chloro-2-naphthoyl)amino]-5-[(dimethylamino)carbonyl]cyclohexyl}-5-methyl-4,5,6,7-tetrahydrothiazolo[5,4-c]pyridine-2-carboxamide hydrochloride, 7-chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)cinnoline-3-carboxamide hydrochloride, N-{(1R,2S,5S)-2-{[(5-chlorobenzimidazol-2-yl)carbonyl]amino}-5-[(dimethylamino)carbonyl]cyclohexyl}-5-methyl-4,5,6,7-tetrahydrothiazolo[5,4-c]pyridine-2-carboxamide hydrochloride, N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-7-fluoroisoquinoline-3-carboxamide hydrochloride, N-{(1R,2S,5S)-2-{[(7-chloro-2H-chromen-3-yl)carbonyl]amino}-5-[(dimethylamino)carbonyl]cyclohexyl}-5-methyl-4,5,6,7-tetrahydrothiazolo[5,4-c]pyridine-2-carboxamide hydrochloride, N-{(1R,2S,5S)-2-{[(E)-3-(4-chlorophenyl)-2-propenoyl]amino}-5-[(dimethylamino)carbonyl]cyclohexyl}-5-methyl-4,5,6,7-tetrahydrothiazolo[5,4-c]pyridine-2-carboxamide hydrochloride, 6-chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-4-oxo-1,4-dihydroquinoline-2-carboxamide hydrochloride, tert-butyl 2-[({(1R,2S,5S)-2-{[(5-chloroindol-2-yl)carbonyl]amino}-5-[(dimethylamino)carbonyl]cyclohexyl}amino)carbonyl]-4,6-dihydro-5H-pyrrolo[3,4-d]thiazole-5-carboxylate, 5-chloro-N-{(1S,2R,4S)-2-[[(5,6-dihydro-4H-pyrrolo[3,4-d]thiazol-2-yl)carbonyl]amino]-4-[(dimethylamino)carbonyl]cyclohexyl}indole-2-carboxamide hydrochloride, 5-chloro-N-((1S,2R,4S)-4-[(dimethylamino)carbonyl]-2-{[(5-methyl-5,6-dihydro-4H-pyrrolo[3,4-d]thiazol-2-yl)carbonyl]amino}cyclohexyl)indole-2-carboxamide hydrochloride, tert-butyl 2-{[(((1R,2S,5S)-5-[(dimethylamino)carbonyl]-2-{[(5-fluoroindol-2-yl)carbonyl]amino}cyclohexyl)amino]carbonyl}-4,6-dihydro-5H-pyrrolo[3,4-d]thiazole-5-carboxylate, N-{(1S,2R,4S)-2-[[(5,6-dihydro-4H-pyrrolo[3,4-d]thiazol-2-yl)carbonyl]amino]-4-[(dimethylamino)carbonyl]cyclohexyl}-5-fluoroindole-2-carboxamide hydrochloride, N-((1S,2R,4S)-4-[(dimethylamino)carbonyl]-2-{[(5-methyl-5,6-dihydro-4H-pyrrolo[3,4-d]thiazol-2-yl)carbonyl]amino}cyclohexyl)-5-fluoroindole-2-carboxamide hydrochloride, N-{(1R,2S,5S)-2-[(6-chloro-2-naphthoyl)amino]-5-[(dimethylamino)carbonyl]cyclohexyl}-5-methyl-5,6-dihydro-4H-pyrrolo[3,4-d]thiazole-2-carboxamide hydrochloride, 7-chloro-N-((1S,2R,4S)-4-[(dimethylamino)carbonyl]-2-{[(5-methyl-5,6-dihydro-4H-pyrrolo[3,4-d]thiazol-2-yl)carbonyl]amino}cyclohexyl)cinnoline-3-carboxamide hydrochloride and 7-chloro-N-((1S,2R,4S)-4-[(dimethylamino)carbonyl]-2-{[(5-methyl-5H-pyrrolo[3,4-d]thiazol-2-yl)carbonyl]amino}cyclohexyl)cinnoline-3-carboxamide, 7-chloro-N-((1S,2R,4S)-4-[(dimethylamino)carbonyl]-2-{[(5-methyl-5,6-dihydro-4H-pyrrolo[3,4-d]thiazol-2-yl)carbonyl]amino}cyclohexyl)isoquinoline-3-carboxamide hydrochloride, tert-butyl 2-[({(1R,2S,5S)-2-{[(5-chloroindol-2-yl)carbonyl]amino}-5-[(dimethylamino)carbonyl]cyclohexyl}amino)carbonyl]-6,6-dimethyl-6,7-dihydrothiazolo[4,5-c]pyridine-5(4H)-carboxylate, N-{(1R,2S,5S)-2-{[(5-chloroindol-2-yl)carbonyl]amino}-5-[(dimethylamino)carbonyl]cyclohexyl}-6,6-dimethyl-4,5,6,7-tetrahydrothiazolo[4,5-c]pyridine-2-carboxamide hydrochloride, tert-butyl 2-[({(1R,2S,5S)-2-{[(5-chloroindol-2-yl)carbonyl]amino}-5-[(dimethylamino)carbonyl]cyclohexyl}amino)carbonyl]-5,7-dihydro-6H-pyrrolo[3,4-d]pyrimidine-6-carboxylate, N-{(1R,2S,5S)-2-{[(5-chloroindol-2-yl)carbonyl]amino}-5-[(dimethylamino)carbonyl]cyclohexyl}-6-methyl-6,7-dihydro-5H-pyrrolo[3,4-d]pyrimidine-2-carboxamide hydrochloride, 7-chloro-N-((1S,2R,4S)-4-[(dimethylamino)carbonyl]-2-{[(6-methyl-6,7-dihydrothiazolo[4,5-d]pyrimidin-2-yl)carbonyl]amino}cyclohexyl)isoquinoline-3-carboxamide hydrochloride, 7-chloro-N-((1S,2R,4S)-4-{[ethyl(methyl)amino]carbonyl}-2-{[(5-methyl-4,5,6,7-tetrahydrothiazolo[5,4-c]pyridin-2-yl)carbonyl]amino}cyclohexyl)isoquinoline-3-carboxamide hydrochloride, N-{(1R,2S,5S)-2-{[(2-chloro-6H-thieno[2,3-b]pyrrol-5-yl)carbonyl]amino}-5-[(dimethylamino)carbonyl]cyclohexyl}-5-methyl-4,5,6,7-tetrahydrothiazolo[5,4-c]pyridine-2-carboxamide, 6-chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-4-oxo-1,4-dihydroquinazoline-2-carboxamide hydrochloride, N-{(1R,2S,5S)-2-{[2-(4-chloroanilino)-2-oxoethanethioyl]amino}-5-[(dimethylamino)carbonyl]cyclohexyl}-5-methyl-4,5,6,7-tetrahydrothiazolo[5,4-c]pyridine-2-carboxamide, N-{(1R,2S,5S)-2-({2-[(5-chloropyridin-2-yl)amino]-2-oxoethanethioyl}amino)-5-[(dimethylamino)carbonyl]cyclohexyl}-5-methyl-4,5,6,7-tetrahydrothiazolo[5,4-c]pyridine-2-carboxamide, N-{(1R,2S,5S)-2-({2-[(5-chloropyridin-2-yl)amino]-2-thioxoacetyl}amino)-5-[(dimethylamino)carbonyl]cyclohexyl}-5-methyl-4,5,6,7-tetrahydrothiazolo[5,4-c]pyridine-2-carboxamide, $N^1$-(5-chloro-2-thienyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, N-{(1R,2S,5S)-2-{[(4-chloroanilino)carbonyl]amino}-5-[(dimethylamino)carbonyl]cyclohexyl}-5-methyl-4,5,6,7-tetrahydrothiazolo[5,4-c]pyridine-2-carboxamide hydrochloride, $N^1$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-$N^2$-(5-fluoropyridin-2-yl)ethanediamide hydrochloride, $N^1$-(4-chlorophenyl)-$N^2$-((1S,2R,4S)-4-[(dimethylamino)carbonyl]-2-{[(5-methyl-5,6-dihydro-4H-pyrrolo[3,4-d]thiazol-2-yl)carbonyl]amino}cyclohexyl)ethanediamide hydrochloride, $N^1$-[4-chloro-2-(trifluoromethyl)phenyl]-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, $N^1$-{4-chloro-2-[(dimethylamino)carbonyl]phenyl}-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, $N^1$-[4-chloro-2-(hydroxymethyl)phenyl]-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, $N^1$-(4-chloro-2-methoxyphenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, N-{(1R,2S,5S)-2-{[2-(4-chloroanilino)-2-(hydroxyimino)acetyl]amino}-5-[(dimethylamino)carbonyl]cyclohexyl}-5-methyl-4,5,6,7-tetrahydrothiazolo[5,4-c]pyridine-2-carboxamide hydrochloride, $N^1$-(4-chlorophenyl)-$N^3$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)malonamide hydrochloride, $N^1$-(3-chlorophenyl)-$N^3$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)malonamide hydrochloride, $N^1$-(5-chloropyridin-2-yl)-$N^2$-((1S,2R,4S)-4-{[ethyl(methyl)amino]carbonyl}-2-{[(5-methyl-4,5,6,7-tetrahydrothiazolo[5,4-c]pyridin-2-yl)carbonyl]amino}cyclohexyl)ethanediamide hydrochloride, $N^1$-(4-chlorophenyl)-$N^2$-((1S,2R,4S)-4-{[ethyl(methyl)amino]carbonyl}-2-{[(5-methyl-4,5,6,7-tetrahydrothiazolo[5,4-c]pyridin-2-yl)carbonyl]amino}cyclohexyl)ethanediamide hydrochloride, $N^1$-(5-bromopyridin-2-yl)-$N^2$-((1S,2R,4S)-4-{[ethyl(methyl)amino]carbonyl}-2-{[(5-methyl-4,5,6,7-tetrahydrothiazolo[5,4-c]pyridin-2-yl)carbonyl]amino}cyclohexyl)ethanediamide hydrochloride, $N^1$-(4-chloro-3-fluorophenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, N-{(1R,2S,5S)-2-{[3-(4-chlorophenyl)-3-oxopropanoyl]amino}-5-[(dimethylamino)carbonyl]cyclohexyl}-5-methyl-4,5,6,7-tetrahydrothiazolo[5,4-c]pyridine-2-carboxamide, $N^1$-(5-chloropyridin-2-yl)-$N^2$-((1R,2R,4S)-4-[(dimethylamino)carbonyl]-2-{[(5-methyl-5H-pyrrolo[3,4-d]thiazol-2-yl)carbonyl]amino}cyclohexyl)ethanediamide, $N^1$-[(5-chloropyridin-2-yl)amino]-$N^2$-((1R,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, $N^1$-(4-chlorophenyl)-$N^2$-((1R,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide, $N^1$-{(1R,2S,5S)-2-{[(5-chloroindol-2-yl)carbonyl]amino}-5-[(dimethylamino)carbonyl]cyclohexyl}-$N^2$-(pyridin-4-yl)ethanediamide hydrochloride, $N^1$-{(1R,2S,5S)-2-{[(5-chloroindol-2-yl)carbonyl]amino}-5-[(dimethylamino)carbonyl]cyclohexyl}-$N^2$-(pyridin-3-yl)ethanediamide hydrochloride, $N^1$-{(1R,2S,5S)-2-{[(5-chloroindol-2-yl)carbonyl]amino}-5-[(dimethylamino)carbonyl]cyclohexyl}-$N^2$-(piperidin-4-yl)ethanediamide hydrochloride, $N^1$-{(1R,2S,5S)-2-{[(5-chloroindol-2-yl)carbonyl]amino}-5-[(dimethylamino)carbonyl]cyclohexyl}-$N^2$-(1-methylpiperidin-4-yl)ethanediamide hydrochloride, $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-$N^1$-methylethanediamide hydrochloride, $N^1$-(5-chloropyrimidin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, $N^1$-(4-chlorophenyl)-$N^2$-((1S,2R,4S)-4-{[ethyl(methyl)amino]carbonyl}-2-{[(5-methyl-5,6-dihydro-4H-pyrrolo[3,4-d]thiazol-2-yl)carbonyl]amino}cyclohexyl)ethanediamide hydrochloride, $N^1$-(5-bromopyridin-2-yl)-$N^2$-((1S,2R,4S)-4-{[ethyl(methyl)amino]carbonyl}-2-{[(5-methyl-5,6-dihydro-4H-pyrrolo[3,4-d]thiazol-2-yl)carbonyl]amino}cyclohexyl)ethanediamide hydrochloride, $N^1$-(5-chloropyridin-2-yl)-$N^2$-((1S,2R,4S)-4-{[ethyl(methyl)amino]carbonyl}-2-{[(5-methyl-5,6-dihydro-4H-pyrrolo[3,4-d]thiazol-2-yl)carbonyl]amino}cyclohexyl)ethanediamide hydrochloride, $N^1$-(4-chloro-3-methoxyphenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, $N^1$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-$N^2$-(4-ethylphenyl)ethanediamide, $N^1$-(5-chloropyrazin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, $N^1$-(4-chloro-3-nitrophenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, $N^1$-(4-chloro-2-nitrophenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, $N^1$-(3-amino-4-chlorophenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, $N^1$-(2-amino-4-chlorophenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, $N^1$-(6-chloro-4-methylpyridin-3-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride, N-{(1R,2S,5S)-2-({[(E)-2-(4-chlorophenyl)diazenyl]carbonyl}amino)-5-[(dimethylamino)carbonyl]cyclohexyl}-5-methyl-4,5,6,7-tetrahydrothiazolo[5,4-c]pyridine-2-carboxamide hydrochloride, N-{(1R,2S,5S)-2-({[2-(4-chlorophenyl)hydrazino]carbonyl}amino)-5-[(dimethylamino)carbonyl]cyclohexyl}-5-methyl-4,5,6,7-tetrahydrothiazolo[5,4-c]pyridine-2-carboxamide hydrochloride, $N^1$-(5-chloropyridin-2-yl)-$N^2$-((1S,2R,4S)-4-[(dimethylamino)carbonyl]-2-{[(4,5,6,7-tetrahydrothiazolo[5,4-c]pyridin-2-yl)carbonyl]amino}cyclohexyl)ethanediamide hydrochloride, N-{(1R,2S,5S)-2-{[2-(4-chlorophenoxy)acetyl]amino}-5-[(dimethylamino)carbonyl]cyclohexyl}-5-methyl-4,5,6,7-tetrahydrothiazolo[5,4-c]pyridine-2-carboxamide hydrochloride, 7-chloro-N-((1S,2R,4S)-4-[(dimethylamino)carbonyl]-2-{[(5-methyl-5H-pyrrolo[3,4-d]thiazol-2-yl)carbonyl]amino}cyclohexyl)-3-isoquinolinecarboxamide hydrochloride, N-{(1R,2S,5S)-2-{[(6-chloro-4-oxo-4H-chromen-2-yl)carbonyl]amino}-5-[(dimethylamino)carbonyl]cyclohexyl}-5-methyl-4,5,6,7-tetrahydrothiazolo[5,4-c]pyridine-2-carboxamide hydrochloride, $N^1$-(5-chloropyridin-2-yl)-$N^2$-((1S,2R,4S)-4-[(dimethylamino)carbonyl]-2-{[(5-methyl-4,5,6,7-tetrahydrothieno[3,2-c]pyridin-2-yl)carbonyl]amino}cyclohexyl)ethanediamide hydrochloride, $N^1$-(5-chloropyridin-2-yl)-$N^2$-((1S,2R,4S)-4-[(dimethylamino)carbonyl]-2-{[(5-isopropyl-4,5,6,7-tetrahydrothiazolo[5,4-c]pyridin-2-yl)carbonyl]amino}cyclohexyl)ethanediamide hydrochloride, N-((1R,2S,5S)-5-[(dimethylamino)carbonyl]-2-{[2-(4-fluoroanilino)-2-oxoethanethioyl]amino}cyclohexyl)-5-methyl-4,5,6,7-tetrahydrothiazolo[5,4-c]pyridine-2-carboxamide hydrochloride, N-[(1R,2S,5S)-5-[(dimethylamino)carbonyl]-2-({2-[(5-fluoropyridin-2-yl)amino]-2-oxoethanethioyl}amino)cyclohexyl}-5-methyl-4,5,6,7-tetrahydrothiazolo[5,4-c]pyridine-2-carboxamide hydrochloride, N-{(1R,2S,5S)-2-({2-[(5-chloropyridin-2-yl)amino]-2-oxoethanethioyl}amino)-5-[(dimethylamino)carbonyl]cyclohexyl}-5-methyl-5H-pyrrolo[3,4-d]thiazole-2-carboxamide, N-{(1R,2S,5S)-2-({2-[(5-chloropyridin-2-yl)amino]-2-oxoethanethioyl}amino)-5-[(dimethylamino)carbonyl]cyclohexyl}-5-methyl-5,6-dihydro-4H-pyrrolo[3,4-d]thiazole-2-carboxamide hydrochloride, $N^1$-(5-chloropyridin-2-yl)-$N^2$-[(1S,2R,4S)-4-[(dimethylamino)carbonyl]-2-({[6-(dimethylamino)-4,5,6,7-tetrahydrobenzothiazol-2-yl]carbonyl}amino)cyclohexyl]ethanediamide, N-{(1R,2S,5S)-2-[({[(4-chlorophenyl)sulfonyl]amino}carbonyl)amino]-5-[(dimethylamino)carbonyl]cyclohexyl}-5-methyl-4,5,6,7-tetrahydrothiazolo[5,4-c]pyridine-2-carboxamide hydrochloride, $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide, $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonate monohydrate, N-{(1R,2S,5S)-5-[(dimethylamino)carbonyl]-2-({2-[(5-methylpyridin-2-yl)amino]-2-oxoethanethioyl}amino)cyclohexyl}-5-methyl-4,5,6,7-tetrahydrothiazolo[5,4-c]pyridine-2-carboxamide hydrochloride, N-{(1R,2S,5S)-2-{[2-(4-chloroanilino)-1-methoxyimino-2-oxoethyl]amino}-5-[(dimethylamino)carbonyl]cyclohexyl}-5-methyl-4,5,6,7-tetrahydrothiazolo[5,4-c]pyridine-2-carboxamide hydrochloride, $N^1$-(5-chloropyridin-2-yl)-$N^2$-[(1S,2R,4S)-4-[(dimethylamino)carbonyl]-2-({[1-(pyridin-4-yl)piperidin-4-yl]carbonyl}amino)cyclohexyl]ethanediamide hydrochloride, $N^1$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-$N^2$-(5-ethynylpyridin-2-yl)ethanediamide, $N^1$-(5-chloropyridin-2-yl)-$N^2$-((1S,2R,4S)-4-[(dimethylamino)carbonyl]-2-{[(5-methyl-5,6-dihydro-4H-thieno[2,3-c]pyrrol-2-yl)carbonyl]amino}cyclohexyl)ethanediamide, N-{(1R,2S,5S)-2-({2-[(6-chloropyridazin-3-yl)amino]-2-oxoethanethioyl}amino)-5-[(dimethylamino)carbonyl]cyclohexyl}-5-methyl-4,5,6,7-tetrahydrothiazolo[5,4-c]pyridine-2-carboxamide hydrochloride, N-{(1R,2S,5S)-2-({2-[(6-chloropyridin-3-yl)amino]-2-oxoethanethioyl}amino)-5-[(dimethylamino)carbonyl]cyclohexyl}-5-methyl-4,5,6,7-tetrahydrothiazolo[5,4-c]pyridine-2-carboxamide hydrochloride, $N^1$-(5-chloropyridin-2-yl)-$N^2$-{(1S,2R,4S)-4-[(dimethylamino)carbonyl]-2-[(thieno[3,2-b]pyridin-2-ylcarbonyl)amino]cyclohexyl}ethanediamide hydrochloride, $N^1$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-$N^2$-(5-methylpyridin-2-yl)ethanediamide hydrochloride, $N^1$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-$N^2$-(4-methylphenyl)ethanediamide hydrochloride, tert-butyl {4-chloro-5-[({(1R,2S,5S)-2-({2-[(5-chloropyridin-2-yl)amino]-2-oxoacetyl}amino)-5-[(dimethylamino)carbonyl]cyclohexyl}amino)carbonyl]-3-thienyl}methyl(methyl)carbamate, $N^1$-{(1S,2R,4S)-2-[({3-chloro-4-[(methylamino)methyl]-2-thienyl}carbonyl)amino]-4-[(dimethylamino)carbonyl]cyclohexyl}-$N^2$-(5-chloropyridin-2-yl)ethanediamide, $N^1$-{(1S,2R,4S)-2-{[(3-chloro-4-{[4,5-dihydro-1,3-oxazol-2-yl(methyl)amino]methyl}-2-thienyl)carbonyl]amino}-4-[(dimethylamino)carbonyl]cyclohexyl}-$N^2$-(5-chloropyridin-2-yl)ethanediamide hydrochloride, $N^1$-(5-chloropyridin-2-yl)-$N^2$-((1R,2R,4S)-4-[(dimethylamino)carbonyl]-2-{[(5-methyl-5,6,7,8-tetrahydro-4H-thiazolo[5,4-c]azepin-2-yl)carbonyl]amino}cyclohexyl)ethanediamide hydrochloride, $N^1$-(5-chloropyridin-2-yl)-$N^2$-((1S,2R,4S)-4-[(dimethylamino)carbonyl]-2-{[(4,4,5-trimethyl-5,6-dihydro-4H-pyrrolo[3,4-d]thiazol-2-yl)carbonyl]amino}cyclohexyl)ethanediamide hydrochloride, tert-butyl 6-[({(1R,2S,5S)-2-({2-[(5-chloropyridin-2-yl)amino]-2-oxoacetyl}amino)-5-[(dimethylamino)carbonyl]cyclohexyl}amino)carbonyl]-1,3-dihydro-2H-pyrrolo[3,4-c]pyridine-2-carboxylate, N$^1$-(5-chloro-2-pyridinyl)-N$^2$-{(1S,2R,4S)-2-[(2,3-dihydro-1H-pyrrolo[3,4-c]pyridin-6-ylcarbonyl)amino]-4-[(dimethylamino)carbonyl]cyclohexyl}ethanediamide hydrochloride, N$^1$-(5-chloro-2-pyridinyl)-N$^2$-((1S,2R,4S)-4-[(dimethylamino)carbonyl]-2-{[(2-methyl-2,3-dihydro-1H-pyrrolo[3,4-c]pyridin-6-yl)carbonyl]amino}cyclohexyl)ethanediamide hydrochloride, N$^1$-(5-chloropyridin-2-yl)-N$^2$-{(1S,2R,4S)-4-[(dimethylamino)carbonyl]-2-[(5,6,7,8-tetrahydro[1,6]naphthyridin-2-ylcarbonyl)amino]cyclohexyl}ethanediamide hydrochloride, N$^1$-(5-chloropyridin-2-yl)-N$^2$-((1S,2R,4S)-4-[(dimethylamino)carbonyl]-2-{[(6-methyl-5,6,7,8-tetrahydro[1,6]naphthyridin-2-yl)carbonyl]amino}cyclohexyl)ethanediamide hydrochloride, N$^1$-(5-chloropyridin-2-yl)-N$^2$-[(1S,2R,4S)-4-[(dimethylamino)carbonyl]-2-({[5-(pyridin-4-yl)pyrimidin-2-yl]carbonyl}amino)cyclohexyl]ethanediamide hydrochloride, N$^1$-(5-chloropyridin-2-yl)-N$^2$-{(1S,2R,4S)-4-[(dimethylamino)carbonyl]-2-[({2'-[(dimethylamino)methyl][1,1'-biphenyl]-4-yl}carbonyl)amino]cyclohexyl}ethanediamide hydrochloride, N$^1$-(5-chloropyridin-2-yl)-N$^2$-[(1S,2R,4S)-4-[(dimethylamino)carbonyl]-2-({4-[2-(hydroxymethyl)pyridin-4-yl]benzoyl}amino)cyclohexyl]ethanediamide hydrochloride, N$^1$-{(1S,2R,4S)-2-({4-[2-(aminomethyl)pyridin-4-yl]benzoyl}amino)-4-[(dimethylamino)carbonyl]cyclohexyl}-N$^2$-(5-chloropyridin-2-yl)ethanediamide hydrochloride, N$^1$-(5-chloropyridin-2-yl)-N$^2$-[(1S,2R,4S)-4-[(dimethylamino)carbonyl]-2-({[1-(phenylsulfonyl)piperidin-4-yl]carbonyl}amino)cyclohexyl]ethanediamide, N$^1$-(5-chloropyridin-2-yl)-N$^2$-[(1S,2R,4S)-4-[(dimethylamino)carbonyl]-2-({[1-(4-fluorobenzoyl)piperidin-4-yl]carbonyl}amino)cyclohexyl]ethanediamide D22-5792, N$^1$-(5-chloropyridin-2-yl)-N$^2$-((1S,2R,4S)-4-[(dimethylamino)carbonyl]-2-{[4-(pyrrolidin-1-ylcarbonyl)benzoyl]amino}cyclohexyl)ethanediamide, N$^1$-(5-chloropyridin-2-yl)-N$^2$-((1S,2R,4S)-4-[(dimethylamino)carbonyl]-2-{[4-(pyrrolidin-1-ylmethyl)benzoyl]amino}cyclohexyl)ethanediamide hydrochloride, N-{(1R,2S,5S)-2-{[(4-chloroanilino)sulfonyl]amino}-5-[(dimethylamino)carbonyl]cyclohexyl}-5-methyl-4,5,6,7-tetrahydrothiazolo[5,4-c]pyridine-2-carboxamide hydrochloride, N-{(1R,2S,5S)-2-({2-[(5-chloropyrimidin-2-yl)amino]-2-oxoethanethioyl}amino)-5-[(dimethylamino)carbonyl]cyclohexyl}-5-methyl-4,5,6,7-tetrahydrothiazolo[5,4-c]pyridine-2-carboxamide hydrochloride, N-{(1R,2S,5S)-2-{[2-(4-chloro-3-nitroanilino)-2-oxoethanethioyl]amino}-5-[(dimethylamino)carbonyl]cyclohexyl}-5-methyl-4,5,6,7-tetrahydrothiazolo[5,4-c]pyridine-2-carboxamide hydrochloride, N-{(1R,2S,5S)-2-{[2-(3-amino-4-chloroanilino)-2-oxoethanethioyl]amino}-5-[(dimethylamino)carbonyl]cyclohexyl}-5-methyl-4,5,6,7-tetrahydrothiazolo[5,4-c]pyridine-2-carboxamide hydrochloride, tert-butyl 6-[({(1R,2S,5S)-2-({2-[(5-chloropyridin-2-yl)amino]-2-oxoacetyl}amino)-5-[(dimethylamino)carbonyl]cyclohexyl}amino)carbonyl]-1,3-dihydro-2H-pyrrolo[3,4-c]pyridine-2-carboxylate, N-{(1R,2S,5S)-2-({2-[(5-chloropyridin-2-yl)amino]-2-oxoethanethioyl}amino)-5-[(dimethylamino)carbonyl]cyclohexyl}-2-methyl-2,3-dihydro-1H-pyrrolo[3,4-c]pyridine-6-carboxamide hydrochloride, N-{(1R,2S,5S)-2-({2-[(5-chloropyridin-2-yl)amino]-2-oxoethanethioyl}amino)-5-[(dimethylamino)carbonyl]cyclohexyl}-1-(pyridin-4-yl)-4-piperidinecarboxamide hydrochloride, N-{(1R,2S,5S)-2-{[(7-chlorocinnolin-3-yl)carbothioyl]amino}-5-[(dimethylamino)carbonyl]cyclohexyl}-5-methyl-4,5,6,7-tetrahydrothiazolo[5,4-c]pyridine-2-carboxamide hydrochloride, N-{(1R,2S,5S)-2-({[(4-chlorobenzoyl)amino]carbonyl}amino)-5-[(dimethylamino)carbonyl]cyclohexyl}-5-methyl-4,5,6,7-tetrahydrothiazolo[5,4-c]pyridine-2-carboxamide hydrochloride, N-{(1R,2S,5S)-2-{[(E)-3-(5-chloropyridin-2-yl)acryloyl]amino}-5-[(dimethylamino)carbonyl]cyclohexyl}-5-methyl-4,5,6,7-tetrahydrothiazolo[5,4-c]pyridine-2-carboxamide hydrochloride, N-{(1R,2S,5S)-2-{[(Z)-3-(4-chlorophenyl)-2-fluoroacryloyl]amino}-5-[(dimethylamino)carbonyl]cyclohexyl}-5-methyl-4,5,6,7-tetrahydrothiazolo[5,4-c]pyridine-2-carboxamide hydrochloride, N-[(1R,2S,5S)-5-[(dimethylamino)carbonyl]-2-({2-[(5-fluoropyridin-2-yl)amino]-2-oxoethanethioyl}amino)cyclohexyl]-5-methyl-5,6,7,8-tetrahydro-4H-thiazolo[5,4-c]azepine-2-carboxamide hydrochloride, tert-butyl (3-{[(((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)amino]carbonyl}phenyl)(imino)methylcarbamate, N-{(1R,2S,5S)-2-({3-[amino(imino)methyl]benzoyl}amino)-5-[(dimethylamino)carbonyl]cyclohexyl}-5-methyl-4,5,6,7-tetrahydrothiazolo[5,4-c]pyridine-2-carboxamide hydrochloride, N-{(1R,2S,5S)-2-[(3-cyanobenzoyl)amino]-5-[(dimethylamino)carbonyl]cyclohexyl}-5-methyl-4,5,6,7-tetrahydrothiazolo[5,4-c]pyridine-2-carboxamide, N-{(1R,2S,5S)-2-({3-[amino(hydroxyimino)methyl]benzoyl}amino)-5-[(dimethylamino)carbonyl]cyclohexyl}-5-methyl-4,5,6,7-tetrahydrothiazolo[5,4-c]pyridine-2-carboxamide hydrochloride, ethyl (3-{[(((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)amino]carbonyl}phenyl)(imino)methylcarbamate, N-[(1R,2S,5S)-5-[(dimethylamino)carbonyl]-2-({3-[imino(methylamino)methyl]benzoyl}amino)cyclohexyl]-5-methyl-4,5,6,7-tetrahydrothiazolo[5,4-c]pyridine-2-carboxamide formate D22-9226, N-{(1R,2S,5S)-2-({3-[amino(methoxyimino)methyl]benzoyl}amino)-5-[(dimethylamino)carbonyl]cyclohexyl}-5-methyl-4,5,6,7-tetrahydrothiazolo[5,4-c]pyridine-2-carboxamide hydrochloride, N$^1$-(5-chloropyridin-2-yl)-N$^2$-((1S,2R,4S)-4-[(dimethylamino)carbonyl]-2-{[4-(3-oxomorpholin-4-yl)benzoyl]amino}cyclohexyl)ethanediamide, N-{(1R,2S,5S)-2-{[(Z)-3-(5-chlorothien-2-yl)-2-fluoro-2-propenoyl]amino}-5-[(dimethylamino)carbonyl]cyclohexyl}-5-methyl-4,5,6,7-tetrahydrothiazolo[5,4-c]pyridine-2-carboxamide hydrochloride, N-{(1R,2S,5S)-2-({2-[(5-chloropyridin-2-yl)amino]-2-oxoethanethioyl}amino)-5-[(dimethylamino)carbonyl]cyclohexyl}-6-methyl-5,6,7,8-tetrahydro-4H-thiazolo[5,4-d]azepine-2-carboxamide hydrochloride, N$^1$-(5-chloropyridin-2-yl)-N$^2$-{(1S,2R,4S)-2-[(6,7-dihydro-4H-pyrano[4,3-d]thiazol-2-ylcarbonyl)amino]-4-[(dimethylamino)carbonyl]cyclohexyl}ethanediamide, N-{(1R,2S,5S)-2-({2-[(5-chloropyridin-2-yl)amino]-2-oxoethanethioyl}amino)-5-[(dimethylamino)carbonyl]cyclohexyl}-6-methyl-5,6,7,8-tetrahydro[1,6]naphthyridine-2-carboxamide, $N^1$-(5-chloropyridin-2-yl)-$N^2$-((1S,2R,4S)-4-[(dimethylamino)carbonyl]-2-{[(2-methyl-1,2,3,4-tetrahydroisoquinolin-6-yl)carbonyl]amino}cyclohexyl)ethanediamide hydrochloride, $N^1$-(5-chloropyridin-2-yl)-$N^2$-[(1S,2R,4S)-2-{[(5-methyl-4,5,6,7-tetrahydrothiazolo[5,4-c]pyridin-2-yl)carbonyl]amino}-4-(1,2,4-oxadiazol-3-yl)cyclohexyl]ethanediamide hydrochloride, $N^1$-(5-chloropyridin-2-yl)-$N^2$-[(1S,2R,4S)-2-{[(5-methyl-4,5,6,7-tetrahydrothiazolo[5,4-c]pyridin-2-yl)carbonyl]amino}-4-(1,3,4-oxadiazol-2-yl)cyclohexyl]ethanediamide, N-[(1R,2S,5S)-5-[(dimethylamino)carbonyl]-2-({2-[(5-fluoropyridin-2-yl)amino]-2-oxoethanethioyl}amino)cyclohexyl]-5-methyl-4,5,6,7-tetrahydrothiazolo[5,4-c]pyridine-2-carboxamide, N-[(1R,2S,5S)-5-[(dimethylamino)carbonyl]-2-({2-[(5-fluoropyridin-2-yl)amino]-2-oxoethanethioyl}amino)cyclohexyl]-5-methyl-4,5,6,7-tetrahydrothiazolo[5,4-c]pyridine-2-carboxamide citrate monohydrate, and $N^1$-(5-chloropyridin-2-yl)-$N^2$-[(1S,2R,4S)-2-{[(5-methyl-4,5,6,7-tetrahydrothiazolo[5,4-c]pyridin-2-yl)carbonyl]amino}-4-(1,2,4-oxadiazol-5-yl)cyclohexyl]ethanediamide hydrochloride.

EXAMPLES

The present invention will next be described in detail by way of examples, which should not be construed as limiting the invention thereto.

Example 1

Ethyl (1S,3R,4R)-3-[(t-butoxycarbonyl)amino]-4-hydroxycyclohexanecarboxylate

Ethyl (1S,3S,6S)-7-oxabicyclo[4.1.0]heptane-3-carboxylate (5 g) was dissolved in ethanol (25 mL), and 28% aqueous ammonia (50 mL) was added to the solution at room temperature, followed by stirring at 40° C. for 24 hours. The solvent was evaporated under reduced pressure, to thereby yield 5.25 g of crude ethyl (1S,3R,4R)-3-amino-4-hydroxycyclohexanecarboxylate. The crude product was dissolved in ethanol (10 mL), and a solution (5 mL) of di-tert-butyl dicarbonate (7.69 g) in ethanol was added under ice-cooling to the solution, followed by stirring at room temperature for 1 hour. The solvent was evaporated under reduced pressure, and the residue was subjected to silica gel column chromatography (n-hexane:ethyl acetate=1:1), to thereby yield 5.42 g of the title compound.

$^1$H-NMR (CDCl$_3$) δ: 1.28 (3H, t, J=7.2 Hz), 1.45 (9H, s), 1.38-1.57 (2H, m) 1.86-1.95 (1H, m), 2.05-2.17 (1H, m), 2.29-2.39 (2H, m), 2.61-2.68 (1H, m), 3.25-3.66 (3H, m), 4.17 (2H, q, J=7.2 Hz), 4.53 (1H, br.s)

$[α]_D^{25}$=+25° (c=1.0, chloroform)

Example 2

Ethyl (1S,3R,4R)-3-[(t-butoxycarbonyl)amino]-4-hydroxycyclohexanecarboxylate

2N Ammonia-ethanol solution (80 mL) was added at room temperature to ethyl (1S,3S,6S)-7-oxabicyclo[4.1.0]heptane-3-carboxylate (8 g), and the mixture was stirred in an autoclave at 75° C. for 72 hours. After completion of reaction, the solvent was evaporated under reduced pressure, to thereby yield 9.13 g of crude ethyl (1S,3R,4R)-3-amino-4-hydroxycyclohexanecarboxylate. The crude product was dissolved in ethanol (40 mL), and a solution (6 mL) of di-tert-butyl dicarbonate (11.28 g) in ethanol was added under ice-cooling to the solution. The mixture was stirred at room temperature for 15 hours, and the solvent was evaporated under reduced pressure. The residue was subjected to silica gel column chromatography (n-hexane:ethyl acetate=1:1), to thereby yield 9.95 g of the title compound. Spectral data of this compound were found to be identical with those of the compound of Example 1.

Example 3 ethyl (1S,3R,4R)-3-[(t-butoxycarbonyl)amino]-4-hydroxycyclohexanecarboxylate

Saturated ammonia-ethanol solution (20 mL) was added at room temperature to ethyl (1S,3S,6S)-7-oxabicyclo[4.1.0]heptane-3-carboxylate (1 g), and the mixture was stirred in an autoclave at 50° C. for 72 hours. Thereafter, the solvent was evaporated under reduced pressure, to thereby yield 1.21 g of crude ethyl (1S,3R,4R)-3-amino-4-hydroxycyclohexanecarboxylate. The crude product was dissolved in ethanol (5 mL), and a solution (2 mL) of di-tert-butyl dicarbonate (1.28 g) in ethanol was added under ice-cooling to the solution. The mixture was stirred at room temperature for 1 hour, and the solvent was evaporated under reduced pressure. The residue was subjected to silica gel column chromatography (n-hexane:ethyl acetate=1:1), to thereby yield 1.46 g of the title compound. Spectral data of this compound were found to be identical with those of the compound of Example 1.

Example 4

Ethyl (1S,3R,4R)-3-[(t-butoxycarbonyl)amino]-4-methanesulfonyloxycyclohexanecarboxylate Methanesulfonyl chloride (0.42 mL) was added at room temperature to a solution (16.4 mL) of ethyl (1S,3R,4R)-3-[(t-butoxycarbonyl)amino]-4-hydroxycyclohexanecarboxylate (1.09 g) in ethyl acetate. Triethylamine (0.90 mL) was added at room temperature to the reaction mixture, followed by stirring for 1 hour while the temperature was maintained. Water was added to the reaction mixture, and the organic layer was recovered and dried with magnesium sulfate. The solvent was evaporated under reduced pressure, and a solvent mixture (10.2 mL) of diisopropyl ether and isopropyl alcohol (2:1) was added to the residue, followed by stirring at room temperature for 3 hours. The formed crystals were recovered by filtration, to thereby yield 1.15 g of the title compound.

$^1$H-NMR (CDCl$_3$) δ: 1.24 (3H, t, J=7.3 Hz), 1.45 (9H, s), 1.65-1.80 (2H, m) 1.87-2.07 (3H, m), 2.25-2.32 (1H, m), 2.52-2.61 (1H, m), 3.06 (3H, s), 3.80-3.86 (1H, m), 4.16 (2H, q, J=7.3 Hz) 4.60-4.70 (1H, m), 4.72 (1H, br.s)

$[α]_D^{25}$=−10° (c=1.0, chloroform

Example 5

Ethyl (1S,3R,4S)-4-azido-3-[(t-butoxycarbonyl)amino]cyclohexanecarboxylate

Sodium azide (357.6 mg) and tetrabutylammonium chloride (229.3 mg) were added at room temperature to a solution (2 mL) of ethyl (1S,3R,4R)-3-[(t-butoxycarbonyl)amino]-4-methanesulfonyloxycyclohexanecarboxylate (1.01 g) in N-methyl-2-pyrrolidone, followed by stirring at 60° C. for 74 hours. Water and ethyl acetate were added to the reaction mixture, and the organic layer was washed with aqueous saturated sodium bicarbonate solution and water, followed by drying over magnesium sulfate anhydrate. The solvent was evaporated under reduced pressure, and the residue was subjected to silica gel column chromatography (n-hexane ethyl acetate=4:1), to thereby yield 734.7 mg of the title compound.

$^1$H-NMR (CDCl$_3$) δ: 1.26 (3H, t, J=7.1 Hz), 1.45 (9H, s), 1.38-2.33 (6H, m) 2.57-2.68 (1H, m), 3.77-4.20 (4H, m), 4.63 (1H, br.s).

$[α]_D^{25}$=+62° (c=1.0, chloroform)

Example 6

Ethyl (1S,3R,4S)-4-azido-3-[(t-butoxycarbonyl)amino]cyclohexanecarboxylate

Sodium azide (357.6 mg) was added at room temperature to a solution (2 mL) of ethyl (1S,3R,4R)-3-[(t-butoxycarbonyl)amino]-4-methanesulfonyloxycyclohexanecarboxylate (1.01 g) in N-methyl-2-pyrrolidone, followed by stirring at 60° C. for 74 hours. Water and ethyl acetate were added to the reaction mixture, and the organic layer was washed with aqueous saturated sodium bicarbonate solution and water, followed by drying over magnesium sulfate anhydrate. The solvent was evaporated under reduced pressure, and the residue was subjected to silica gel column chromatography (n-hexane:ethyl acetate=4:1), to thereby yield 601.7 mg of the title compound. Spectral data of this compound were found to be identical with those of the compound of Example 5.

Example 7

Ethyl (1S,3R,4S)-4-azido-3-[(t-butoxycarbonyl)amino]cyclohexanecarboxylate

Sodium azide (357.6 mg) and tetramethylammonium chloride (91.0 mg) were added at room temperature to a solution (2 mL) of ethyl (1S,3R,4R)-3-[(t-butoxycarbonyl)amino]-4-methanesulfonyloxycyclohexanecarboxylate (1.01 g) in N-methyl-2-pyrrolidone, followed by stirred at 60° C. for 74 hours. Water and ethyl acetate were added to the reaction mixture, and the organic layer was washed with aqueous saturated sodium bicarbonate solution and water, followed by drying over magnesium sulfate anhydrate. The solvent was evaporated under reduced pressure, and the residue was subjected to silica gel column chromatography (n-hexane:ethyl acetate=4:1), to thereby yield 648.3 mg of the title compound. Spectral data of this compound were found to be identical with those of the compound of Example 5.

Example 8

Ethyl (1S,3R,4S)-4-azido-3-[(t-butoxycarbonyl)amino]cyclohexanecarboxylate

Sodium azide (357.6 mg) and benzyltriethylammonium chloride (189.1 mg) were added at room temperature to a solution (2 mL) of ethyl (1S,3R,4R)-3-[(t-butoxycarbonyl)amino]-4-methanesulfonyloxycyclohexanecarboxylate (1.01 g) in N-methyl-2-pyrrolidone, followed by stirring at 60° C. for 74 hours. Water and ethyl acetate were added to the reaction mixture, and the organic layer was washed with aqueous saturated sodium bicarbonate solution and water, followed by drying over magnesium sulfate anhydrate. The solvent was evaporated under reduced pressure, and the residue was subjected to silica gel column chromatography (n-hexane:ethyl acetate=4:1), to thereby yield 655.2 mg of the title compound. Spectral data of this compound were found to be identical with those of the compound of Example 5.

Example 9

Ethyl (1S,3R,4S)-4-azido-3-[(t-butoxycarbonyl)amino]cyclohexanecarboxylate

Sodium azide (357.6 mg) and tetraethylammonium chloride (137.5 mg) were added at room temperature to a solution (2 mL) of ethyl (1S,3R,4R)-3-[(t-butoxycarbonyl)amino]-4-methanesulfonyloxycyclohexanecarboxylate (1.01 g) in N-methyl-2-pyrrolidone, followed by stirring at 60° C. for 74 hours. Water and ethyl acetate were added to the reaction mixture, and the organic layer was washed with aqueous saturated sodium bicarbonate solution and water, followed by drying over magnesium sulfate anhydrate. The solvent was evaporated under reduced pressure, and the residue was subjected to silica gel column chromatography (n-hexane ethyl acetate=4:1), to thereby yield 675.1 mg of the title compound. Spectral data of this compound were found to be identical with those of the compound of Example 5.

Example 10

Ethyl (1S,3R,4S)-4-azido-3-[(t-butoxycarbonyl)amino]cyclohexanecarboxylate

Sodium azide (357.6 mg) and trioctylmethylammonium chloride (335.5 mg) were added at room temperature to a solution (2 mL) of ethyl (1S,3R,4R)-3-[(t-butoxycarbonyl)amino]-4-methanesulfonyloxycyclohexanecarboxylate (1.01 g) in N-methyl-2-pyrrolidone, followed by stirring at 60° C. for 74 hours. Water and ethyl acetate were added to the reaction mixture, and the organic layer was washed with aqueous saturated sodium bicarbonate solution and water, followed by drying over magnesium sulfate anhydrate. The solvent was evaporated under reduced pressure, and the residue was subjected to silica gel column chromatography (n-hexane ethyl acetate=4:1), to thereby yield 706.2 mg of the title compound. Spectral data of this compound were found to be identical with those of the compound of Example 5.

Example 11

Ethyl (1S,3R,4S)-4-azido-3-[(t-butoxycarbonyl)amino]cyclohexanecarboxylate

Sodium azide (357.6 mg) and tetrahexylammonium chloride (323.8 mg) were added at room temperature to a solution (2 mL) of ethyl (1S,3R,4R)-3-[(t-butoxycarbonyl)amino]-4-methanesulfonyloxycyclohexanecarboxylate (1.01 g) in N-methyl-2-pyrrolidone, followed by stirring at 60° C. for 74 hours. Water and ethyl acetate were added to the reaction mixture, and the organic layer was washed with aqueous saturated sodium bicarbonate solution and water, followed by drying over magnesium sulfate anhydrate. The solvent was evaporated under reduced pressure, and the residue was subjected to silica gel column chromatography (n-hexane ethyl acetate=4:1), to thereby yield 712.2 mg of the title compound.

Spectral data of this compound were found to be identical with those of the compound of Example 5.

Example 12 t-Butyl{(1R,2R,5S)-5-[(dimethylamino)carbonyl]-2-hydroxycyclocarbonyl}carbamate

28% Aqueous ammonia (5 mL) was added to (1S,3S,6R)—N,N-dimethyl-7-oxabicyclo[4.1.0]heptane-3-carboxamide (1 g) at room temperature, followed by stirring at 40° C. for 5 hours. The solvent was evaporated under reduced pressure, to thereby yield 1.18 g of crude (1S,3R,4R)-3-amino-4-hydroxy-N,N-dimethylcyclohexanecarboxamide. The crude product was dissolved in water (5 mL), and di-tert-butyl dicarbonate (1.93 g) and 10N aqueous sodium hydroxide (1.5 mL) were added to the solution at room temperature. The mixture was stirred at 40° C. for 2 hours, and then extracted thrice with 4-methyl-2-pentanone (MIBK) (5 mL). The extraction solvent was evaporated under reduced pressure, and 4-methyl-2-pentanone (MIBK) (3 mL) was added to the residue, followed by stirring at room temperature. The formed crystals were recovered by filtration and dried, to thereby yield 1.26 g of the title compound.

$^1$H-NMR (CDCl$_3$) δ: 1.44 (9H, s), 1.48-1.59 (2H, m), 1.77-1.78 (2H, m) 1.86-1.97 (1H, m), 2.11-2.17 (1H, m), 2.78-2.83 (1H, m), 2.92 (3H, s), 3.02 (3H, s), 3.53-3.60 (1H, m), 3.94 (1H, br.s), 4.52-4.68 (1H, m)

Example 13

(1R,2R,4S)-2-[(t-butoxycarbonyl)amino]-4-[(dimethylamino)carbonyl]cyclohexylmethanesulfonate Methanesulfonyl chloride (159.07 g) was added at room temperature to a solution (1,875 mL) of t-butyl{(1R,2R,5S)-5-[(dimethylamino)carbonyl]-2-hydroxycyclohexylcarbamate (214.59 g) in 4-methyl-2-pentanone (MIBK). Triethylamine (170.62 g) was added to the reaction mixture at room temperature, followed by stirring for 1 hour while the temperature was maintained. Water was added to the reaction mixture, and the organic layer was recovered. The solvent was evaporated under reduced pressure, and MIBK (750 mL) was added to the residue, followed by stirring at room temperature for 3 hours. The formed crystals were recovered by filtration and dried, to thereby yield 242.57 g of the title compound.

$^1$H-NMR (CDCl$_3$) δ: 1.45 (9H, s), 1.58-1.66 (1H, m), 1.67-1.76 (1H, m), 1.84-1.96 (2H, m), 2.04-2.15 (1H, m), 2.17-2.26 (1H, m), 2.75-2.81 (1H, m), 2.94 (3H, s), 3.04 (3H, s), 3.07 (3H, s), 4.00-4.08 (1H, m), 4.69-4.82 (2H, m)

Example 14 t-Butyl{(1R,2R,5S)-2-azido-5-[(dimethylamino)carbonyl]cyclohexyl}carbamate

Sodium azide (7.14 g) and dodecylpyridinium chloride (7.80 g) were added at room temperature to a solution (40 mL) of (1R,2R,4S)-2-[(t-butoxycarbonyl)amino]-4-[(dimethylamino)carbonyl]cyclohexylmethanesulfonate (20.0 g) in N,N-dimethylacetamide (DMAC), followed by stirring at 60° C. for 72 hours. Water and ethyl acetate were added to the reaction mixture, and the organic layer was washed with aqueous saturated sodium bicarbonate solution and water. The solvent was evaporated under reduced pressure, and a solvent mixture (300 mL) of n-hexane and ethyl acetate (5:1) was added to the residue. The mixture was stirred at room temperature for 1 hour, and the formed crystals were recovered by filtration. A solvent mixture (300 mL) of n-hexane and ethyl acetate (5:1) was added to the recovered crystals, followed by stirring/recovering by filtration twice, to thereby yield 4.6 g of the title compound.

$^1$H-NMR (CDCl$_3$) δ: 1.46 (9H, s), 1.55-1.74 (3H, m), 1.75-1.82 (1H, m) 2.02-2.12 (2H, m), 2.74-2.83 (1H, m), 2.93 (3H, s), 3.02 (3H, s), 3.72-3.78 (1H, m), 4.07-4.13 (1H, m), 4.61-4.66 (1H, m)

Example 15 t-Butyl{(1R,2S,5S)-2-amino-5-[(dimethylamino)carbonyl]cyclohexyl}carbamate oxalate Sodium azide (7.14 g) and dodecylpyridinium chloride (7.80 g) were added at room temperature to a solution (100 mL) of (1R,2R,4S)-2-[(t-butoxycarbonyl)amino]-4-[(dimethylamino)carbonyl]cyclohexylmethanesulfonate (20.0 g) in toluene, followed by stirring at 60° C. for 72 hours. Water was added to the reaction mixture, and the organic layer was washed with aqueous saturated sodium bicarbonate solution and water. Methanol, 7.5% Pd—C, and ammonium formate were added to the washed organic layer, followed by stirring at 40° C. for 1 hour. Pd—C was removed by filtration, and The solvent was evaporated under reduced pressure. Hydrated acetonitrile (200 mL) and anhydrous oxalic acid (4.94 g) were added to the residue. The mixture was stirred at room temperature for 17 hours, and the formed crystals were recovered by filtration. Acetonitrile (200 mL) was added to the recovered crystals, followed by stirring at 40° C. for 24 hours. The formed crystals were recovered by filtration and dried, to thereby yield 12.7 g of the title compound.

$^1$H-NMR (D$_2$O) δ: 1.30 (9H, s), 1.37-1.49 (2H, m), 1.63 (1H, t, J=2.7 Hz), 1.72-1.83 (3H, m), 2.77 (3H, s), 2.80 (1H, t, J=12.4 Hz), 2.96 (3H, m), 3.32 (1H, d, J=12.2 Hz), 4.10 (1H, br)

Elemental analysis: Calc. C; 50.70%, H; 7.75%, N; 10.96%, Obsd: C; 51.19%, H; 7.79%, N; 11.19%.

Example 16

Ethyl (1S,3R,4S)-4-amino-3-t-butoxycarbonylaminocyclohexanecarboxylate oxalate 7.5% Pd—C (100 mg) and ammonium formate (444.1 mg) were added at room temperature to a solution (10 mL) of ethyl (1S,3R,4S)-4-azido-3-[(t-butoxycarbonyl)amino]cyclohexanecarboxylate (1.0 g) in ethanol, followed by stirring at 50° C. for 1 hour. The catalyst was removed by filtration, and the filtrate was concentrated, to thereby yield 911.0 mg of crude ethyl (1S,3R,4S)-4-amino-3-t-butoxycarbonylaminocyclohexanecarboxylate. The crude product was dissolved in ethyl acetate (20 mL), and anhydrous oxalic acid (286.4 mg) was added to the solution, followed by stirring at room temperature for 16 hours. The formed crystals were recovered by filtration and dried, to thereby yield 1.16 g of the title compound.

$^1$H-NMR (CD$_3$OD) δ: 1.24 (3H, t, J=7.1 Hz), 1.47 (9H, s), 1.53-1.90 (4H, m), 1.98-2.10 (2H, m), 2.58-2.72 (1H, m), 3.25-3.35 (1H, m), 4.12 (2H, q, J=7.1 Hz), 4.18 (1H, m).

Elemental analysis (as ⅓ hydrate): Calc. C; 50.25%, H; 7.56%, N; 7.33%, Obsd. C; 50.29%, H; 7.45%, N; 7.29%.

Example 17

Ethyl (1S,3R,4S)-4-{[(benzyloxy)carbonyl]amino}-3-[(t-butoxycarbonyl)amino]cyclohexanecarboxylate Ethyl (1S,3R,4S)-4-amino-3-t-butoxycarbonylaminocyclohexanecarboxylate oxalate (1.2 g) was dissolved in ethyl acetate (20 mL), and water (10 mL) and sodium hydrogencarbonate (1.48 g) were added to the solution. Benzyl chloroformate (737.3 mg) was added dropwise to the mixture under ice-cooling. The reaction mixture was stirred at room temperature for 3 hours. Water was added to the reaction mixture, and the resultant aqueous layer was extracted with ethyl acetate. The organic layers were combined and washed with water, followed by drying over magnesium sulfate anhydrate. The solvent was evaporated under reduced pressure, and diisopropyl ether (20 mL) was added to the residue. The mixture was stirred at room temperature, and the formed crystals were recovered by filtration and dried, to thereby yield 1.09 g of the title compound.
$^1$H-NMR (CDCl$_3$) δ: 1.24 (3H, t, J=7.1 Hz), 1.29-1.44 (1H, m), 1.44 (9H, s), 1.51-1.64 (1H, m), 1.72-2.10 (4H, m), 2.27-2.43 (1H, m), 3.60-3.73 (1H, m), 4.00-4.18 (3H, m), 4.62 (1H, br.s), 5.01-5.13 (2H, m), 5.26 (1H, br.s), 7.27-7.38 (5H, m).
$[\alpha]_D^{25}$=−22° (c=1.0, chloroform)

Example 18

Benzyl t-butyl{(1S,2R,4S)-4-[(dimethylamino)carbonyl]cyclohexan-1,2-diyl}biscarbamate Ethyl (1S,3R,4S)-4-{[(benzyloxy)carbonyl]amino}-3-[(t-butoxycarbonyl)amino]cyclohexanecarboxylate (3.2 g) was dissolved in ethanol (32 mL), and 2M aqueous lithium hydroxide solution (11.4 mL) was added to the solution at room temperature, followed by stirring for 3 hours. 6N Hydrochloric acid (2.6 mL) was added to the reaction mixture so that the pH thereof was adjusted to 7, and the reaction mixture as is was evaporated. DMF (32 mL), dimethylamine hydrochloride (2.48 g), 1-hydroxybenzotriazol (1.54 g) were added to the residue, followed by stirring for dissolution. 1-Ethyl-3-(3-dimethylaminopropyl)carbodiimide hydrochloride (2.19 g) was added to the solution, followed by stirring at room temperature for 16 hours. The reaction mixture was extracted with ethyl acetate and water, and the aqueous layer was extracted with ethyl acetate. The organic layers were combined and washed with water, followed by drying over magnesium sulfate anhydrate. The solvent was evaporated under reduced pressure, and the residue was subjected to silica gel column chromatography, to thereby yield 2.94 g of the title compound.
$^1$H-NMR (CDCl$_3$) δ: 1.20-1.50 (2H, m), 1.44 (9H, s), 1.50-2.10 (4H, m), 2.60 (1H, br.t, J=11.6 Hz), 2.93 (3H, s), 3.02 (3H, s), 3.70 (1H, br.s), 4.14 (1H, br.s), 4.65 (1H, br.s), 5.00-5.30 (3H, m), 7.26-7.40 (5H, m).

Example 19 t-Butyl{(1R,2S,5S)-2-amino-5-[(dimethylamino)carbonyl]cyclohexyl}carbamate oxalate 7.5% Pd—C (230 mg) was added to a solution (35 mL) of benzyl t-butyl{(1S,2R,4S)-4-[(dimethylamino)carbonyl]cyclohexan-1,2-diyl}biscarbamate (2.3 g) in ethanol, and the mixture was stirred in a hydrogen atmosphere for 16 hours. Pd—C was removed by filtration, and the filtrate was concentrated under reduced pressure. Ethyl acetate (20 mL) and anhydrous oxalic acid (493.6 mg) were added to the residue, followed by stirring at room temperature for 17 hours. The formed crystals were recovered by filtration, to thereby yield 1.93 g of the title compound. Spectral data of this compound were found to be identical with those of the compound of Example 15.

Referential Example 1 t-Butyl[(1R,2S,5S)-2-({[(5-chloropyridin-2-yl)amino](oxo)acetyl}amino)-5-(dimethylaminocarbonyl)cyclohexyl]carbamate Triethylamine (169 mL) was added at 60° C. to a suspension (550 mL) of t-butyl {(1R,2S,5S)-2-amino-5-[(dimethylamino)carbonyl]cyclohexyl}carbamate oxalate (100.1 g) in acetonitrile. At the same temperature, ethyl[5-chloropyridin-2-yl]amino](oxo)acetate hydrochloride (84.2 g) was added to the mixture, followed by stirring for 6 hours. Thereafter, the mixture was stirred at room temperature for 16 hours. Water was added to the reaction mixture, followed by stirring at 10° C. for 1.5 hours. The formed crystals were recovered by filtration, to thereby yield 106.6 g of the title compound.
$^1$H-NMR (CDCl$_3$) δ: 1.25-1.55 (2H, m), 1.45 (9H, s), 1.60-2.15 (5H, m), 2.56-2.74 (1H, br.s), 2.95 (3H, s), 3.06 (3H, s), 3.90-4.01 (1H, m), 4.18-4.27 (1H, m), 4.70-4.85 (0.7H, br), 5.70-6.00 (0.3H, br.s), 7.70 (1H, dd, J=8.8, 2.4 Hz), 7.75-8.00 (1H, br), 8.16 (1H, br.d, J=8.8 Hz), 8.30 (1H, d, J=2.4 Hz), 9.73 (1H, s).

Referential Example 2

N-(5-Chloropyridin-2-yl)-N'-[(1S,2R,4S)-4-(dimethylcarbamoyl)-2-{[(5-methyl-4,5,6,7-tetrahydro[1,3]thiazolo[5,4-c]pyridin-2-yl)carbonyl]amino}cyclohexyl]ethanediamide Methanesulfonic acid (66 mL) was added at room temperature to a suspension of t-butyl[(1R,2S,5S)-2-({[(5-chloropyridin-2-yl)amino](oxo)acetyl}amino)-5-(dimethylaminocarbonyl)cyclohexyl]carbamate (95.1 g) in acetonitrile (1,900 mL), and the mixture was stirred at the same temperature for 2 hours. Triethylamine (155 mL), 5-methyl-4,5,6,7-tetrahydro[1,3]thiazolo[5,4-c]pyridine-2-carboxylic acid hydrochloride (52.5 g), 1-hydroxybenzotriazole (33.0 g), and 1-ethyl-3-(3-dimethylaminopropyl)carbodiimide hydrochloride (46.8 g) were added to the reaction mixture under ice-cooling, and the mixture was stirred at room temperature for 16 hours. Triethylamine and water were added thereto, followed by stirring under ice-cooling for 1 hour. The formed crystals were recovered by filtration, to thereby yield 103.2 g of the title compound.
$^1$H-NMR (CDCl$_3$) δ: 1.60-1.98 (3H, m), 2.00-2.16 (3H, m), 2.52 (3H, s), 2.78-2.90 (3H, m), 2.92-2.98 (2H, m), 2.95 (3H, s), 3.06 (3H, s), 3.69 (1H, d, J=15.4 Hz), 3.75 (1H, d, J=15.4 Hz), 4.07-4.15 (1H, m), 4.66-4.72 (1H, m), 7.40 (1H, dd, J=8.8, 0.6 Hz), 7.68 (1H, dd, J=8.8, 2.4 Hz), 8.03 (1H, d, J=7.8 Hz), 8.16 (1H, dd, J=8.8, 0.6 Hz), 8.30 (1H, dd, J=2.4, 0.6 Hz), 9.72 (1H, s).

Referential Example 3

N-(5-Chloropyridin-2-yl)-N'-[(1S,2R,4S)-4-(dimethylcarbamoyl)-2-{[(5-methyl-4,5,6,7-tetrahydro[1,3]thiazolo[5,4-c]pyridin-2-yl)carbonyl]amino}cyclohexyl]ethanediamide p-toluenesulfonate monohydrate N-(5-Chloropyridin-2-yl)-N'-[(1S,2R,4S)-4-(dimethylcarbamoyl)-2-{[(5-methyl-4,5,6,7-tetrahydro[1,3]thiazolo

[5,4-c]pyridin-2-yl)carbonyl]amino}cyclohexyl]ethanediamide p-toluenesulfonic acid (86.8 g) was dissolved in 30% hydrous ethanol (418 mL) at 60° C., and a solution (167 mL) of p-toluenesulfonic acid monohydrate (29.0 g) in 30% hydrous ethanol was added to the solution. The mixture was stirred at 70° C. for 1 hour, and then gradually cooled. At room temperature, ethanol was added to the cooled mixture, followed by stirring for 16 hours. The reaction mixture was stirred under ice-cooling for 1 hour, and the formed crystals were recovered by filtration, to thereby yield 102.9 g of the title compound.

$^1$H-NMR (DMSO-$d_6$) δ: 1.45-1.54 (1H, m), 1.66-1.78 (3H, m), 2.03-2.10 (2H, m), 2.28 (3H, s), 2.79 (3H, s), 2.91-3.02 (1H, m), 2.93 (3H, s), 2.99 (3H, s), 3.13-3.24 (2H, m), 3.46-3.82 (2H, m), 3.98-4.04 (1H, m), 4.43-4.80 (3H, m), 7.11 (2H, d, J=7.8 Hz), 7.46 (2H, d, J=8.2 Hz), 8.01 (2H, d, J=1.8 Hz), 8.46 (1H, t, J=1.8 Hz), 8.75 (1H, d, J=6.9 Hz), 9.10-9.28 (1H, br.s), 10.18 (1H, br.s), 10.29 (1H, s).

Elemental analysis: Calc. C; 50.43%, H; 5.46%, N; 13.28%, Obsd. C; 50.25%, H; 5.36%, N; 13.32%.

Referential Example 4

Benzyl t-butyl[(1R,2S,4S)-4-(1,3,4-oxadiazol-2-yl)cyclohexan-1,2-diyl]biscarbamate Ethyl (1S,3R,4S)-4-{[(benzyloxy)carbonyl]amino}-3-[(t-butoxycarbonyl)amino]cyclohexanecarboxylate (5.0 g) was dissolved in isopropanol (50 mL), and 2M aqueous lithium hydroxide (11.4 mL) was added to the reaction mixture at room temperature, followed by stirring for 3 hours. 6N Hydrochloric acid was added under ice-cooling to the reaction mixture so as to the pH thereof was adjusted to 2.5, and the mixture was stirred for 2 hours while the temperature was maintained. The formed crystals were recovered by filtration, to thereby yield 4.3 g of crude (1S,3R,4S)-4-{[(benzyloxy)carbonyl]amino}-3-[(t-butoxycarbonyl)amino]cyclohexane carboxylic acid. The crude product (4.0 g) was dissolved in N,N-dimethylformamide (100 mL), and hydrazine monohydrate (765 mg), 1-hydroxybenzotriazole (33.0 g), and 1-ethyl-3-(3-dimethylaminopropyl)carbodiimide hydrochloride (46.8 g) were added to the solution, followed by stirring at room temperature for 16 hours. The reaction mixture was concentrated under reduced pressure, and methylene chloride and saturated aqueous sodium hydrogencarbonate were added to the residue. The organic layer was dried with magnesium sulfate anhydrate, and the desiccant was removed by filtration. Silica gel and methanol were added to the filtrate, and insoluble matter was removed by filtration. The filtrate was concentrated under reduced pressure, to thereby yield 3.71 g of crude benzyl t-butyl[(1S,2R,4S)-4-(hydrazinocarbonyl)cyclohexan-1,2-diyl]biscarbamate. Methyl orthoformate (10 mL) and trifluoroboron-diethyl ether complex (2 drops) were added to the crude product (1.73 g), and the mixture was stirred at 70° C. for 16 hours and cooled to room temperature, followed by concentration under reduced pressure. Methylene chloride and saturated aqueous sodium hydrogencarbonate were added to the residue, and the organic layer was dried over magnesium sulfate anhydrate. The solvent was evaporated under reduced pressure, and the residue was subjected to silica gel column chromatography (methanol:methylene chloride=1:19), to thereby yield 1.89 g of the title compound.

$^1$H-NMR (CDCl$_3$) δ: 1.45 (9H, s), 1.71-2.30 (6H, m), 3.04-3.15 (1H, m), 3.80 (1H, br.s), 4.17 (1H, br.s), 4.75 (1H, br.s), 5.05-5.15 (2H, m), 5.25 (1H, s), 7.30-7.38 (5H, m), 8.35 (1H, s).

Referential Example 5 t-Butyl[(1R,2S,5S)-2-({[(5-chloropyridin-2-yl)amino](oxo)acetyl}amino)-5-(1,3,4-oxadiazol-2-yl)cyclohexyl]carbamate 10% Pd—C (1.2 g) was added to a solution (200 mL) of benzyl t-butyl[(1R,2S,4S)-4-(1,3,4-oxadiazol-2-yl)cyclohexan-1,2-diyl]biscarbamate (4.11 g) in methanol, and the mixture was stirred in a hydrogen atmosphere at room temperature for 1 hour. Pd—C was removed by filtration, and the filtrate was concentrated under reduced pressure. The residue was dissolved in N,N-dimethylformamide (200 mL), and 2-[(5-chloropyridin-2-yl)amino]-2-oxoacetic acid lithium salt (2.45 g), 1-hydroxybenzotriazole (1.47 g), and 1-ethyl-3-(3-dimethylaminopropyl)carbodiimide hydrochloride (3.12 g) were added to the solution, followed by stirring at room temperature for 16 hours. The reaction mixture was concentrated under reduced pressure, and ethyl acetate and 10% aqueous citric acid were added to the residue. The organic layer was washed with saturated brine and saturated aqueous sodium hydrogencarbonate, followed by drying over magnesium sulfate anhydrate. The solvent was evaporated under reduced pressure, to thereby yield 3.35 g of the title compound.

$^1$H-NMR (CDCl$_3$) δ: 1.47 (9H, s), 1.59-1.92 (2H, m), 2.00-2.33 (4H, m) 3.02-3.22 (1H, m), 3.94-4.10 (1H, m), 4.27 (1H, br.s), 4.83 (1H, br.s), 7.71 (1H, dd, J=8.9, 2.6 Hz), 8.00 (1H, d, J=8.9 Hz), 8.32 (1H, d, J=2.6 Hz), 8.37 (1H, br.s), 9.72 (1H, s).

Referential Example 6

N-(5-Chloropyridin-2-yl)-N'-[(1S,2R,4S)-2-{[(5-methyl-4,5,6,7-tetrahydro[1,3]thiazolo[5,4-c]pyridin-2-yl)carbonyl]amino}-4-(1,3,4-oxazol-2-yl)cyclohexyl]ethanediamide 4N Hydrochloric acid-dioxane solution (1.3 mL) was added to a solution (60 mL) of t-butyl[(1R,2S,5S)-2-({[(5-chloropyridin-2-yl)amino](oxo)acetyl}amino)-5-(1,3,4-oxadiazol-2-yl)cyclohexyl]carbamate (241.7 mg) in methylene chloride, and the mixture was stirred at room temperature for 5.5 hours. Additional 4N hydrochloric acid-dioxane solution (0.65 mL) was added thereto, followed by stirring for 1 hour while the temperature was maintained. The solvent was evaporated under reduced pressure, and methylene chloride (10 mL) was added to the residue. The step of concentration under reduced pressure was repeated three times. The residue was dissolved in N,N-dimethylformamide (50 mL), and 5-methyl-4,5,6,7-tetrahydro[1,3]thiazolo[5,4-c]pyridine-2-carboxylic acid hydrochloride (160 mg), 1-hydroxybenzotriazole monohydrate (120 mg), and 1-ethyl-3-(3-dimethylaminopropyl)carbodiimide hydrochloride (150 mg) were added to the solution. The mixture was stirred at room temperature for 18 hours, and the solvent was evaporated under reduced pressure. Ethyl acetate and water were added to the residue, and the organic layer was washed with saturated brine, followed by drying over magnesium sulfate anhydrate. The solvent was evaporated under reduced pressure, and the residue was subjected to silica gel column chromatography (methanol:methylene chloride=2:23 to 1:9), to thereby yield 181.3 mg of the title compound.

$^1$H-NMR (CDCl$_3$) δ: 1.72-2.00 (2H, m), 2.13-2.23 (2H, m), 2.28-2.36 (1H, m), 2.39-2.46 (1H, m), 2.53 (3H, s), 2.80-2.91 (2H, m), 2.93-3.00 (2H, m), 3.28-3.38 (1H, m), 3.69-3.79 (2H, m), 4.14-4.24 (1H, m), 4.68-4.77 (1H, m), 4.68-4.77 (1H, m), 7.51 (1H, d, J=8.3 Hz), 7.70 (1H, dd, J=8.8, 2.5 Hz), 8.14 (1H, d, J=7.8 Hz), 8.18 (1H, d, J=8.8 Hz), 8.31 (1H, d, J=2.5 Hz), 9.72 (1H, s).

The invention claimed is:

1. A process for producing an acid adduct salt of a compound represented by formula (VI-I):

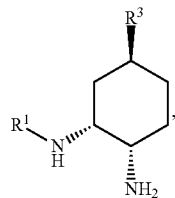
(VI-I)

wherein $R^1$ represents a C2-C5 alkoxycarbonyl group and $R^3$ represents a dimethylcarbamoyl group, said process comprising:

treating a compound represented by formula (A)

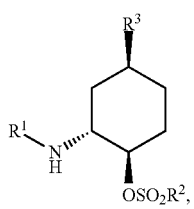
(A)

with an azide in the presence or absence of a phase-transfer catalyst to obtain a mixture comprising a compound represented by formula (V-I) and a compound represented by formula (B):

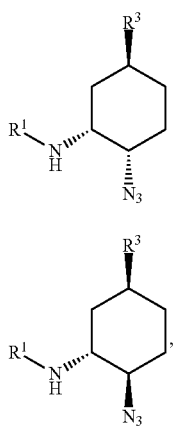
(V-I)

(B)

subjecting said mixture to hydrogenolysis in a C1-C4 alcoholic solvent in the presence of a metallic catalyst and a hydrogen source to obtain a mixture comprising the compound represented by formula (VI-I) and a compound represented by formula (C):

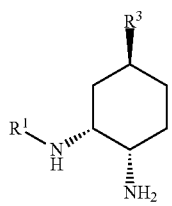
(VI-II)

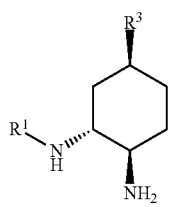
(C)

wherein $R^1$ and $R^3$ for each of formulas (A), (V-I), (B) and (C) have the same meanings as defined for formula (VI-I) and $R^2$ of formula (A) represents a C1-C6 alkyl group, a C1-C6 halogenoalkyl group, or a phenyl group which may have a halogen atom, a C1-C6 alkyl group, a C1-C6 halogenoalkyl group, a C1-C6 alkoxy group, a nitro group, a carbamoyl group, or a cyano group, followed by adding oxalic acid, to obtain an acid adduct salt of the compound represented by formula (VI-I).

2. The process according to claim 1, wherein $R^1$ is a tert-butoxycarbonyl group.

3. The process according to claim 1, wherein the hydrogen source is formic acid or a salt thereof.

4. The process according to claim 1, wherein the hydrogen source is ammonium formate.

5. The process according to claim 1, wherein the azide is selected from the group consisting of an alkali metal azide, an alkaline earth metal azide and a quaternary ammonium azide.

6. The process according to claim 1, wherein the phase-transfer catalyst is present and is selected from the group consisting of a quaternary ammonium salt, a quaternary phosphonium salt, a pyridinium compound and crown ether.

* * * * *

UNITED STATES PATENT AND TRADEMARK OFFICE
CERTIFICATE OF CORRECTION

PATENT NO. : 8,686,189 B2  
APPLICATION NO. : 12/066873  
DATED : April 1, 2014  
INVENTOR(S) : Koji Sato et al.

Page 1 of 1

It is certified that error appears in the above-identified patent and that said Letters Patent is hereby corrected as shown below:

In the Claims

Claim 1, Column 72, line 8, "(VI-II)" should read -- (VI-I) --

Signed and Sealed this
Eighth Day of July, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,686,189 B2 Page 1 of 1
APPLICATION NO. : 12/066873
DATED : April 1, 2014
INVENTOR(S) : Sato et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 871 days.

Signed and Sealed this
Thirtieth Day of May, 2017

Michelle K. Lee
*Director of the United States Patent and Trademark Office*